United States Patent [19]

Barvian et al.

[11] Patent Number: 6,150,359

[45] Date of Patent: Nov. 21, 2000

[54] NAPHTHYRIDINONES FOR INHIBITING PROTEIN TYROSINE KINASE AND CELL CYCLE KINASE MEDIATED CELLULAR PROLIFERATION

[75] Inventors: Mark Robert Barvian, Ann Arbor, Mich.; William Alexander Denny, Auckland, New Zealand; Ellen Myra Dobrusin, Ann Arbor, Mich.; James Marino Hamby, Ann Arbor, Mich.; Howard Daniel Hollis Showalter, Ann Arbor, Mich.; Andrew Mark Thompson, Auckland, New Zealand; Roy Thomas Winters, Ann Arbor; Zhipei Wu, Saline, both of Mich.

[73] Assignee: Warner-Lambert Company, Morris Plains, N.J.

[21] Appl. No.: 09/463,553

[22] PCT Filed: Aug. 13, 1998

[86] PCT No.: PCT/US98/16848

§ 371 Date: Jan. 26, 2000

§ 102(e) Date: Jan. 26, 2000

[87] PCT Pub. No.: WO99/09030

PCT Pub. Date: Feb. 25, 1999

Related U.S. Application Data

[60] Provisional application No. 60/056,746, Aug. 20, 1997.

[51] Int. Cl.$^7$ .......................... A61K 31/5377; A61P 9/10; C07D 471/04
[52] U.S. Cl. ........................ 514/234.5; 544/127; 544/362; 546/122
[58] Field of Search ........................... 544/127; 546/122; 514/234.5

[56] References Cited

U.S. PATENT DOCUMENTS

| | | | |
|---|---|---|---|
| 3,534,039 | 10/1970 | Davoll | 260/256.4 |
| 3,639,401 | 2/1972 | Meyer | 260/256.4 |
| 4,271,164 | 6/1981 | Blankley et al. | 424/251 |
| 5,364,860 | 11/1994 | Bru-Magniez et al. | 514/300 |
| 5,409,930 | 4/1995 | Spada et al. | 514/248 |
| 5,620,981 | 4/1997 | Blankley et al. | 514/258 |
| 5,733,914 | 3/1998 | Blankley et al. | 514/258 |

FOREIGN PATENT DOCUMENTS

WO 96/15128  5/1996  WIPO.

*Primary Examiner*—Robert W. Ramsuer
*Attorney, Agent, or Firm*—Charles W. Ashbrook

[57] ABSTRACT

This invention relates to the inhibition of protein tyrosine kinase (PTK) and cell cycle kinase mediated cellular proliferation. More specifically, this invention relates to naphthyridinones and their use in inhibiting cellular proliferation and PTK or cell cycle kinase enzymatic activity.

65 Claims, No Drawings

NAPHTHYRIDINONES FOR INHIBITING PROTEIN TYROSINE KINASE AND CELL CYCLE KINASE MEDIATED CELLULAR PROLIFERATION

This application is a 371 of PCT/US98/16848 filed Aug. 13, 1998 which claims the benefit of Provisional 60/056,746 filed Aug. 20, 1997.

FIELD OF THE INVENTION

This invention relates to the inhibition of protein tyrosine kinase (PTK) and cell cycle kinase mediated cellular proliferation. More specifically, this invention relates to naphthyridinones and their use in inhibiting cellular proliferation and PTK or cell cycle kinase enzymatic activity.

BACKGROUND OF THE INVENTION

Many disease states are characterized by the uncontrolled proliferation and differentiation of cells. These disease states encompass a variety of cell types and maladies such as cancer, atherosclerosis, restenosis, and psoriasis. Growth factor stimulation, autophosphorylation, and the phosphorylation of intracellular protein substrates are important biological events in the pathomechanisms of proliferative diseases.

In normal cells, the phosphorylation of tyrosine residues on protein substrates serves a critical function in intracellular growth signaling pathways initiated by stimulated extracellular growth factor receptors. For example, the association of growth factors such as Platelet-Derived Growth Factor (PDGF), Fibroblast Growth Factor (FGF), and Epidermal Growth Factor (EGF) with their respective extracellular receptors, PDGFr, FGFr, and EGFr, activates intracellular tyrosine kinase enzyme domains of these receptors, thereby catalyzing the phosphorylation of either intracellular substrates or the receptors themselves. The phosphorylation of growth factor receptors in response to ligand binding is known as autophosphorylation.

For example, the EGF receptor has as its two most important ligands EGF and Transforming Growth Factor α, (TGFα). The receptors appear to have only minor functions in normal adult humans, but are implicated in the disease processes of a large portion of all cancers, especially colon and breast cancer. The closely related Erb-B2 and Erb-B3 receptors have a family of Heregulins as their major ligands, and receptor overexpression and mutation have been unequivocally demonstrated as the major risk factor in poor prognosis breast cancer.

The proliferation and directed migration of vascular smooth muscle cells (VSMC) are important components in such processes as vascular remodeling, restenosis and atherosclerosis. Platelet-derived growth factor has been identified as one of the most potent endogenous VSMC mitogens and chemoattractants. Elevated vascular mRNA expression of PDGF-A and -B chains and PDGF receptors has been observed in balloon-injured rat carotid arteries (*J. Cell. Biol.,* 1990;111:2149–2158). In this injury model, infusion of PDGF also greatly increases intimal thickening and migration of VSMC (*J. Clin. Invest.,* 1992;89:507–511). Furthermore, PDGF-neutralizing antibodies significantly reduce intimal thickening following balloon injury (*Science,* 1991;253:1129–1132). Tyrphostin receptor tyrosine kinase inhibitors which block the PDGF signal transduction pathway have been shown to inhibit PDGF stimulated receptor tyrosine kinase phosphorylation in vivo in the rat cuff injury model (*Drug Develop. Res.,* 1993;29:158–166).

Both acidic fibroblast growth factor (aFGF) and basic fibroblast growth factor (bFGF) have many biological activities, including the ability to promote cellular proliferation and differentiation. Direct evidence in support of FGF involvement in VSMC has been reported by Lindner and Reidy (*Proc. Natl. Acad. Sci. USA,* 88:3739–3743 (1991)), who demonstrated that the systemic injection of a neutralizing antibody against bFGF prior to balloon angioplasty of rat carotid arteries inhibited injury-induced medial SMC proliferation by greater than 80% when measured 2 days after injury. It is likely that bFGF released from damaged cells is acting in a paracrine manner to induce VSMC growth. Recently, Lindner and Reidy (*Cir. Res.,* 1993;73:589–595) demonstrated an increased expression of both mRNA for bFGF and FGFR-1 in replicating VSMCs and endothelium in en face preparations of balloon-injured rat carotid arteries. The data provides evidence that in injured arteries the ligand/receptor system of bFGF and FGFR-1 may be involved in the continued proliferative response of VSMCs leading to neointima formation.

Buchdunger, et al., *Proc. Natl. Acad. Sci.,* 1995;92:2558–2562, reported the inhibition of the PDGF signal transduction pathway both in vitro and in vivo by a PDGF receptor tyrosine protein kinase inhibitor. The compound showed antitumor activity in tumor models using astrocytoma cell lines.

Thus, EGF, PDGF, FGF, and other growth factors play pivotal roles in the pathomechanisms of cellular proliferative diseases such as cancer, atherosclerosis, and restenosis. Upon association with their respective receptors, these growth factors stimulate tyrosine kinase activity as one of the initial biochemical events leading to DNA synthesis and cell division. It thereby follows that compounds which inhibit PTKs associated with intracellular growth factor signal transduction pathways are useful agents for the treatment of cellular proliferative diseases. We have now discovered that certain naphthyridinones inhibit PTKs, and are useful in treating and preventing atherosclerosis, restenosis, and cancer.

The Src family of protein kinases are involved in a number of cellular signaling pathways. For example, Src is involved in growth factor receptor signaling; integrin-mediated signaling; T- and B-cell activation and osteoclast activation. It is known that Src binds to several key receptor and nonreceptor tyrosine kinases such as tyrosine kinases containing receptors for PDGF, EGF, HER2/Neu (an oncogene form of EGF), Fibroblast growth factor, focal adhesion kinase, p130 protein, and p68 protein. In addition, pp60c-src has been shown to be involved in the regulation of DNA synthesis, mitosis, and other cellular activities.

Cell cycle kinases are naturally occurring enzymes involved in regulation of the cell cycle (Meijer L., "Chemical Inhibitors of Cyclin-Dependent Kinases", *Progress in Cell Cycle Research,* 1995;1:351–363). Typical enzymes include the cyclin-dependent kinases (cdk) cdk1, cdk2, cdk4, cdk5, cdk6, and wee-1 kinase. Increased activity or temporally abnormal activation of these kinases has been shown to result in development of human tumors and other proliferative disorders such as restenosis. Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated both preclinical and clinical anti-tumor activity. For example, flavopiridol is a flavonoid that has been shown to be a potent inhibitor of several types of breast and lung cancer cells (Kaur, et al., *J. Natl. Cancer Inst.,* 1992;84:1736–1740; *Int. J. Oncol,* 1996;9:1143–1168). The compound has been shown to inhibit cdk2 and cdk4. Olomoucine [2-(hydroxyethylamine)-6-benzylamine-9-methylpurine] is a potent inhibitor of cdk2 and cdk5 (Vesely, et al., *Eur. J. Biochem.,* 1994;224:771–786), and has been shown to inhibit proliferation of approximately 60 different human tumor cell lines used by the National Cancer Institute (NCI) to screen for new cancer therapies (Abraham, et al., *Biology of the Cell,* 1995;83:105–120).

Despite the progress that has been made, the search continues for small molecular weight compounds that are orally bioavailable and useful for treating a wide variety of human tumors and other proliferative disorders such as restenosis and atherosclerosis.

The present invention provides compounds that inhibit PTKs and cell cycle kinases.

SUMMARY OF THE INVENTION

The present invention provides compounds having the Formula I

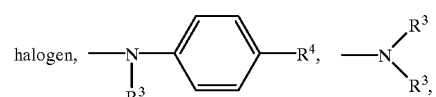

wherein

— — — is absent or a bond;

$R^1$ is

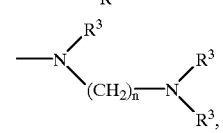 

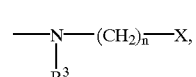 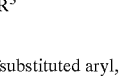

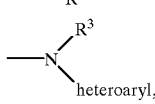 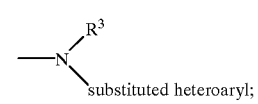

$R^2$ is $C_1$–$C_6$ alkyl, $C_3$–$C_8$ cycloalkyl, or $C_5$–$C_{12}$ bicycloalkyl;
each $R^3$ is independently hydrogen or $C_1$–$C_6$ alkyl;
each n is independently 0 to 7;

$R^4$ is

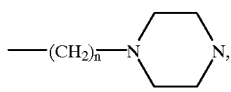

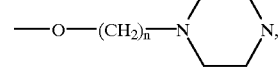

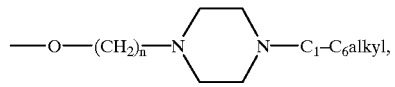

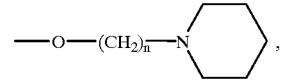

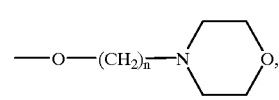

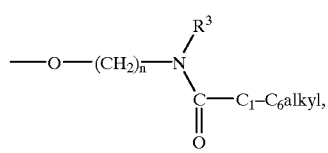

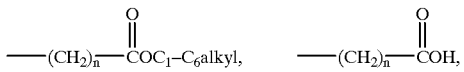

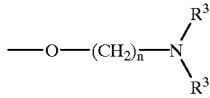

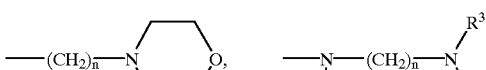

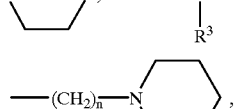

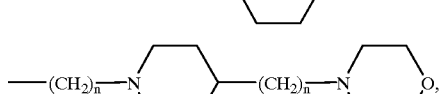

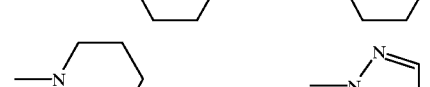

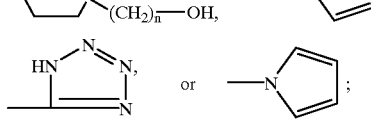

X is <image>piperazinyl-$R^3$</image>, morpholino, or imidazolyl; and $R^5$ is hydrogen, halogen, aryl, substituted aryl, heteroaryl, or substituted heteroaryl, and the pharmaceutically acceptable salts thereof.

In a preferred embodiment of the compounds of Formula I, $R^1$ is 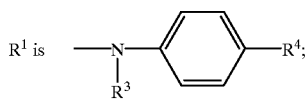

-continued and R⁴ is 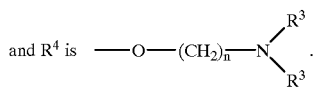

In another preferred embodiment,

R¹ is 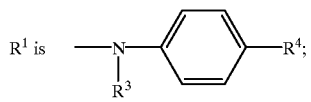

and R⁴ is —O(CH₂)ₙ—X.

In another preferred embodiment,

R¹ is 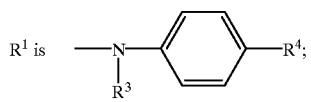

and R⁴ is 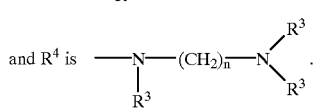

In another preferred embodiment,

R¹ is 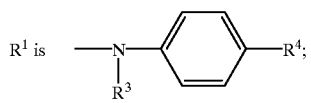

and R⁴ is 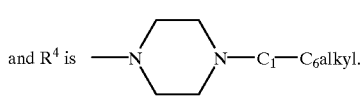

In another preferred embodiment,

R¹ is 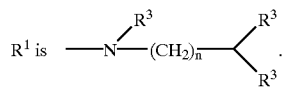

In another preferred embodiment, R¹ is —NH—(CH₂)ₙ—N(CH₂CH₃)₂.

In another preferred embodiment, R⁵ is phenyl or substituted phenyl.

In another preferred embodiment, R⁵ is 2,6-dichlorophenyl.

In another preferred embodiment, R² is methyl.

In another preferred embodiment, R⁵ is 2,6-dichlorophenyl and R² is methyl.

In another preferred embodiment, the present invention provides the compounds:

7-amino-3-(2,6-dichlorophenyl)-1-methyl-1H-[1,6]naphthyridin-2-one;

3-(2,6-dichlorophenyl)-1-methyl-7-methylamino-1H-[1,6]naphthyridin-2-one;

3-(2,6-dichlorophenyl)-7-dimethylamino-1-methyl-1H-[1,6]naphthyridin-2-one;

3-(2,6-dichlorophenyl)-7-[2-(diethylamino)ethylamino]-1-methyl- 1H-[1,6]naphthyridin-2-one;

3-(2,6-dichlorophenyl)-7-[3-(diethylamino)propylamino]-1-methyl-1H-[1,6]naphthyridin-2-one;

3-(2,6-dichlorophenyl)-7-[4-(diethylamino)butylamino]-1-methyl-1H-[1,6]naphthyridin-2-one;

3-(2,6-dichlorophenyl)-7-[5-(diethylamino)pentylamino]-1-methyl-1H-[1,6]naphthyridin-2-one;

3-(2,6-dichlorophenyl)- 1-methyl-7-[3-(4-methylpiperazin-1-yl)propylamino]-1H-[1,6]naphthyridin-2-one;

3-(2,6-dichlorophenyl)-1-methyl-7-[4-(4-methylpiperazin-1-yl)butylamino]-1H-[1,6]naphthyridin-2-one;

3-(2,6-dichlorophenyl)-1-methyl-7-[5-(4-methylpiperazin-1-yl)pentylamino]-1H-[1,6]naphthyridin-2-one;

3-(2,6-dichlorophenyl)-1-methyl-7-[3-(4-morpholino)propylamino]-1H-[1,6]naphthyridin-2-one;

3-(2,6-dichlorophenyl)-7-[3-(imidazol-1-yl)propylamino]-1-methyl-1H-[1,6]naphthyridin-2-one;

3-(2,6-dichlorophenyl)-1-methyl-7-(phenylamino)-1H-[1,6]naphthyridin-2-one;

3-(2,6-dichlorophenyl)-1-methyl-7-(4-pyridylamino)-1H-[1,6]naphthyridin-2-one;

3-(2,6-dichlorophenyl)-7-[(4-methoxyphenyl)amino]-1-methyl-1H-[1,6]naphthyridin-2-one;

3-(2,6-dichlorophenyl)-7-[(4-(2-(diethylamino)ethoxy)phenyl)amino]-1-methyl-1H-[1,6]naphthyridin-2-one;

3-(2,6-dichlorophenyl)-1-methyl-7-[4-(4-morpholino)butylamino]-1H-[1,6]naphthyridin-2-one;

3-(2,6-dichlorophenyl)-7-[(4-(3-(diethylamino)propoxy)phenyl)amino]-1-methyl-1H-[1,6]naphthyridin-2-one;

3-(2,6-dichlorophenyl)-1-methyl-7-[(4-(2-(4-methylpiperazin-1-yl)ethoxy)phenyl)amino]-1H-[1,6]naphthyridin-2-one;

3-(2,6-dichlorophenyl)-1-methyl-7-[(4-(3-(4-methylpiperazin-1-yl)propoxy)phenyl)amino]-1H-[1,6]naphthyridin-2-one;

3-(2,6-dichlorophenyl)-1-methyl-7-[(4-(4-methylpiperazin-1-yl)phenyl)amino]-1H-[1,6]naphthyridin-2-one;

7-Amino-1H-[1,6]naphthyridin-2-one;

7-Amino-1-ethyl-1H-[1,6]naphthyridin-2-one;

7-Fluoro-1-ethyl-1H-[1,6]naphthyridin-2-one;

1-Ethyl-7-phenylamino-1H-[1,6]naphthyridin-2-one;

1-Ethyl-7-(4-methoxyphenylamino)-1H-[1,6]naphthyridin-2-one;

1-Ethyl-7-[4-(4-methylpiperazin-1-yl)phenylamino]-1H-[1,6]naphthyridin-2-one;

1-Ethyl-7-(4-(morpholin-4-yl)phenylamino)-1H-[1,6]naphthyridin-2-one;

1-Ethyl-7-(4-(piperidin-1-yl)phenylamino)-1H-[1,6]naphthyridin-2-one;

1-Ethyl-7-phenylamino-3,4-dihydro-1H-[1,6]naphthyridin-2-one;

7-[4-(2-(Diethylamino)ethoxy)phenylamino]-1-ethyl-1H-[1,6]naphthyridin-2-one;

7-[4-(3-(Diethylamino)propoxy)phenylamino]-1-ethyl-1,6-naphthyridin-2-one;

1-Ethyl-7-[4-(2-(4-methylpiperazin-1-yl)ethoxy)phenylamino]-1,6-naphthyridin-2-one;

1-Ethyl-7-[4-(3-(4-methylpiperazin-1-yl)propoxy)phenylamino]-1,6-naphthyridin-2-one;

1-Ethyl-7-(4-pyridylamino)-1H-[1,6]naphthyridin-2-one;

1-Methyl-7-[4-(4-methylpiperazin-1-yl)phenylamino]-1H-[1,6]naphthyridin-2-one;

1-Isopropyl-7-[4-(4-methylpiperazin-1-yl)phenylamino]-1H-[1,6]naphthyridin-2-one;

1-Isopentyl-7-[4-(4-methylpiperazin-1-yl)phenylamino]-1H-[1,6]naphthyridin-2-one;

1-Cyclopentyl-7-[4-(4-methylpiperazin-1-yl)phenylamino]-1H-[1,6]naphthyridin-2-one;

1-Cyclohexyl-7-[4-(4-methylpiperazin-1-yl)phenylamino]-1H-[1,6]naphthyridin-2-one;

1-Cycloheptyl-7-[4-(4-methylpiperazin-1-yl)phenylamino]-1H-[1,6]naphthyridin-2-one;

1-Bicyclo[2.2.1]hept-2-yl-7-[4-(4-methylpiperazin-1-yl)phenylamino]-1H-[1,6]naphthyridin-2-one;

1-Methyl-7-{4-[4-(3-(morpholin-4-yl)propyl)piperidin-1-yl]phenylamino}-1H-[1,6]naphthyridin-2-one;

1-Ethyl-7-{4-[4-(3-(morpholin-4-yl)propyl)piperidin-1-yl]phenylamino}-1H-[1,6]naphthyridin-2-one;

1-Isopropyl-7-{4-[4-(3-(morpholin-4-yl)propyl)piperidin-1-yl]phenylamino}-1H-[1,6]naphthyridin-2-one;

1-Isopentyl-7-{4-[4-(3-(morpholin-4-yl)propyl)piperidin-1-yl]phenylamino}-1H-[1,6]naphthyridin-2-one;

1-Cyclopentyl-7-{4-[4-(3-(morpholin-4-yl)propyl)piperidin-1-yl]phenylamino}-1H-[1,6]naphthyridin-2-one;

1-Cyclohexyl-7-{4-[4-(3-(morpholin-4-yl)propyl)piperidin-1-yl]phenylamino}-1H-[1,6]naphthyridin-2-one;

1-Cycloheptyl-7-{4-[4-(3-(morpholin-4-yl)propyl)piperidin-1-yl]phenylamino }-1H-[1,6]naphthyridin-2one;

1-Bicyclo[2.2.1]hept-2-yl-7-{4-[4-(3-(morpholin-4-yl)propyl)piperidin-1-yl]phenylamino}-1H-[1,6]naphthyridin-2-one;

1-Methyl-7-{4-[4-(3-(hydroxy)propyl)piperidin-1-yl]phenylamino}-1H-[1,6]naphthyridin-2-one;

1-Ethyl-7-{4-[4-(3-(hydroxy)propyl)piperidin-1-yl]phenylamino}-1H-[1,6]naphthyridin-2-one;

7-{4-[4-(3-(Hydroxy)propyl)piperidin-1-yl]phenylamino}-1-isopropyl-1H-[1,6]naphthyridin-2-one;

7-{4-[4-(3-(Hydroxy)propyl)piperidin-1-yl]phenylamino}-1-isopentyl-1H-[1,6]naphthyridin-2-one;

1-Cyclopentyl-7-{4-[4-(3-(hydroxy)propyl)piperidin-1-yl]phenylamino}-1H-[1,6]naphthyridin-2-one;

1-Cyclohexyl-7-{4-[4-(3-(hydroxy)propyl)piperidin-1-yl]phenylamino}-1H-[1,6]naphthyridin-2-one;

1-Cycloheptyl-7-{4-[4-(3-(hydroxy)propyl)piperidin-1-yl]phenylamino}-1H-[1,6]naphthyridin-2-one;

1-Bicyclo[2.2.1]hept-2-yl-7-{4-[4-(3-(hydroxy)propyl)piperidin-1-yl]phenylamino}-1H-[1,6]naphthyridin-2-one;

1-Methyl-7-(4-(pyrazol-1-yl)phenylamino)-1H-[1,6]naphthyridin-2one;

1-Ethyl-7-(4-(pyrazol-1-yl)phenylamino)-1H-[1,6]naphthyridin-2-one;

1-Isopropyl-7-(4-(pyrazol-1-yl)phenylamino)-1H-[1,6]naphthyridin-2-one;

1-Isopentyl-7-(4-(pyrazol-1-yl)phenylamino)-1H-[1,6]naphthyridin-2-one;

1-Cyclopentyl-7-(4-(pyrazol-1-yl)phenylamino)-1H-[1,6]naphthyridin-2-one;

1-Cyclohexyl-7-(4-(pyrazol-1-yl)phenylamino)-1H-[1,6]naphthyridin-2-one;

1-Cycloheptyl-7-(4-(pyrazol-1-yl)phenylamino)-1H-[1,6]naphthyridin-2-one;

1-Bicyclo[2.2.1]hept-2-yl-7-(4-(pyrazol-1-yl)phenylamino)-1H-[1,6]naphthyridin-2-one;

7-(4-Fluorophenylamino)-1-methyl-1H-[1,6]naphthyridin-2-one;

1-Ethyl-7-(4-fluorophenylamino)-1H-[1,6]naphthyridin-2-one;

7-(4-Fluorophenylamino)-1-isopropyl-1H-[1,6]naphthyridin-2-one;

7-(4-Fluorophenylamino)-1-isopentyl-1H-[1,6]naphthyridin-2-one;

1-Cyclopentyl-7-(4-fluorophenylamino)-1H-[1,6]naphthyridin-2-one;

1-Cyclohexyl-7-(4-fluorophenylamino)-1H-[1,6]naphthyridin-2-one;

1-Cycloheptyl-7-(4-fluorophenylamino)-1H-[1,6]naphthyridin-2-one;

1-Bicyclo[2.2.1]hept-2-yl-7-(4-fluorophenylamino)-1H-[1,6]naphthyridin-2-one;

7-[4-(4-(Hydroxy)piperidin-1-yl)phenylamino]-1-methyl-1H-[1,6]naphthyridin-2-one;

1-Ethyl-7-[4-(4-(hydroxy)piperidin-1-yl)phenylamino]-1H-[1,6]naphthyridin-2-one;

7-[4-(4-(Hydroxy)piperidin-1-yl)phenylamino]-1-isopropyl-1H-[1,6]naphthyridin-2-one;

7-[4-(4-(Hydroxy)piperidin-1-yl)phenylamino]-1-isopentyl-1H-[1,6]naphthyridin-2-one;

1-Cyclopentyl-7-[4-(4-(hydroxy)piperidin-1-yl)phenylamino]-1H-[1,6]naphthyridin-2-one;

1-Cyclohexyl-7-[4-(4-(hydroxy)piperidin-1-yl)phenylamino]-1H-[1,6]naphthyridin-2-one;

1-Cycloheptyl-7-[4-(4-(hydroxy)piperidin-1-yl)phenylamino]-1H-[1,6]naphthyridin-2-one;

1-Bicyclo[2.2.1]hept-2-yl-7-[4-(4-(hydroxy)piperidin-1-yl)phenylamino]-1H-[1,6]naphthyridin-2-one;

7-[4-(3-(Hydroxymethyl)piperidin-1-yl)phenylamino]-1-methyl-1H-[1,6]naphthyridin-2-one;

1-Ethyl-7-[4-(3-(hydroxymethyl)piperidin-1-yl)phenylamino]-1H-[1,6]naphthyridin-2-one;

7-[4-(3-(Hydroxymethyl)piperidin-1-yl)phenylamino]-1-isopropyl-1H-[1,6]naphthyridin-2-one;

7-[4-(3-(Hydroxymethyl)piperidin-1-yl)phenylamino]-1-isopentyl-1H-[1,6]naphthyridin-2-one;

1-Cyclopentyl-7-[4-(3-(hydroxymethyl)piperidin-1-yl)phenylamino]-1H-[1,6]naphthyridin-2-one;

1-Cyclohexyl-7-[4-(3-(hydroxymethyl)piperidin-1-yl)phenylamino]-1H-[1,6]naphthyridin-2-one;

1-Cycloheptyl-7-[4-(3-(hydroxymethyl)piperidin-1-yl)phenylamino]-1H-[1,6]naphthyridin-2-one;

1-Bicyclo[2.2.1]hept-2-yl-7-[4-(3-(hydroxymethyl)piperidin-1-yl)phenylamino]-1H-[1,6]naphthyridin-2-one;

1-Methyl-7-[4-(2H-tetrazol-5-yl)phenylamino]-1H-[1,6]naphthyridin-2-one;

1-Ethyl-7-[4-(2H-tetrazol-5-yl)phenylamino]-1H-[1,6]naphthyridin-2-one;

1-Isopropyl-7-[4-(2H-tetrazol-5-yl)phenylamino]-1H-[1,6]naphthyridin-2-one;

1-Isopentyl-7-[4-(2H-tetrazol-5-yl)phenylamino]-1H-[I,6]naphthyridin-2-one;

1-Cyclopentyl-7-[4-(2H-tetrazol-5-yl)phenylamino]-1H-[1,6]naphthyridin-2-one;

1-Cyclohexyl-7-[4-(2H-tetrazol-5-yl)phenylamino]-1H-[1,6]naphthyridin-2-one;

1-Cycloheptyl-7-[4-(2H-tetrazol-5-yl)phenylamino]-1H-[1,6]naphthyridin-2-one;

1-Bicyclo[2.2.1]hept-2-yl-7-[4-(2H-tetrazol-5-yl)phenylamino]-1H-[1,6]naphthyridin-2-one;

1-Methyl-7-(4-(piperidin-1-yl)phenylamino)-1H-[1,6]naphthyridin-2-one;

1-Isopropyl-7-(4-(piperidin-1-yl)phenylamino)-1H-[1,6]naphthyridin-2-one;

1-Isopentyl-7-(4-(piperidin-1-yl)phenylamino)-1H-[1,6]naphthyridin-2-one;

1-Cyclopentyl-7-(4-(piperidin-1-yl)phenylamino)-1H-[1,6]naphthyridin-2-one;

1-Cyclohexyl-7-(4-(piperidin-1-yl)phenylamino)-1H-[1,6]naphthyridin-2-one;

1-Cycloheptyl-7-(4-(piperidin-1-yl)phenylamino)-1H-[1,6]naphthyridin-2-one;

1-Bicyclo[2.2.1]hept-2-yl-7-(4-(piperidin-1-yl)phenylamino)-1H-[1,6]naphthyridin-2-one;

1-Methyl-7-(4-(pyrrolidin-1-yl)phenylamino)-1H-[1,6]naphthyridin-2-one;

1-Ethyl-7-(4-(pyrrolidin-1-yl)phenylamino)-1H-[1,6]naphthyridin-2-one;

1-Isopropyl-7-(4-(pyrrolidin-1-yl)phenylamino)-1H-[1,6]naphthyridin-2-one;

1-Isopentyl-7-(4-(pyrrolidin-1-yl)phenylamino)-1H-[1,6]naphthyridin-2-one;

1-Cyclopentyl-7-(4-(pyrrolidin-1-yl)phenylamino)-1H-[1,6]naphthyridin-2-one;

1-Cyclohexyl-7-(4-(pyrrolidin-1-yl)phenylamino)-1H-[1,6]naphthyridin-2-one;

1-Cycloheptyl-7-(4-(pyrrolidin-1-yl)phenylamino)-1H-[1,6]naphthyridin-2-one;

1-Bicyclo[2.2.1]hept-2-yl-7-(4-(pyrrolidin-1-yl)phenylamino)-1H-[1,6]naphthyridin-2-one;

1-Methyl-7-[4-(4-methylpiperazin-1-yl)phenylamino]-3,4-dihydro-1H-[1,6]naphthyridin-2-one;

1-Ethyl-7-[4-(4-methylpiperazin-1-yl)phenylamino]-3,4-dihydro-1H-[1,6]naphthyridin-2-one;

1-Isopropyl-7-[4-(4-methylpiperazin-1-yl)phenylamino]-3,4-dihydro-1H-[1,6]naphthyridin-2-one;

1-Isopentyl-7-[4-(4-methylpiperazin-1-yl)phenylamino]-3,4-dihydro-1H-[1,6]naphthyridin-2-one;

1-Cyclopentyl-7-[4-(4-methylpiperazin-1-yl)phenylamino]-3,4-dihydro-1H-[1,6]naphthyridin-2-one;

1-Cyclohexyl-7-[4-(4-methylpiperazin-1-yl)phenylamino]-3,4-dihydro-1H-[1,6]naphthyridin-2-one;

1-Cycloheptyl-7-[4-(4-methylpiperazin-1-yl)phenylamino]-3,4-dihydro-1H-[1,6]naphthyridin-2-one;

1-Bicyclo[2.2.1]hept-2-yl-7-[4-(4-methylpiperazin-1-yl)phenylamino]-3,4-dihydro-1H-[1,6]naphthyridin-2-one;

1-Methyl-7-{4-[4-(3-(morpholin-4-yl)propyl)piperidin-1-yl]-phenylamino}-3,4-dihydro-1H-[1,6]naphthyridin-2-one;

1-Ethyl-7-{4-[4-(3-(morpholin-4-yl)propyl)piperidin-1-yl]phenylamino}-3,4-dihydro-1H-[1,6]naphthyridin-2-one;

1-Isopropyl-7-{4-[4-(3-(morpholin-4-yl)propyl)piperidin-1-yl]phenylamino}-3,4-dihydro-1H-[1,6]naphthyridin-2-one;

1-Isopentyl-7-{4-[4-(3-(morpholin-4-yl)propyl)piperidin-1-yl]phenylamino}-3,4-dihydro-1H-[1,6]naphthyridin-2-one;

1-Cyclopentyl-7-{4-[4-(3-(morpholin-4-yl)propyl)piperidin-1-yl]phenylamino}-3,4-dihydro-1H-[1,6]naphthyridin-2-one;

1-Cyclohexyl-7-{4-[4-(3-(morpholin-4-yl)propyl)piperidin-1-yl]phenylamino}-3,4-dihydro-1H-[1,6]naphthyridin-2-one;

1-Cycloheptyl-7-{4-[4-(3-(morpholin-4-yl)propyl)piperidin-1-yl]phenylamino}-3,4-dihydro-1H-[1,6]naphthyridin-2-one;

1-Bicyclo[2.2.1]hept-2-yl-7-{4-[4-(3-(morpholin-4-yl)propyl)piperidin-1-yl]phenylamino}-3,4-dihydro-1H-[1,6]naphthyridin-2-one;

1-Methyl-7-{4-[4-(3-(hydroxy)propyl)piperidin-1-yl]phenylamino}-3,4-dihydro-1H-[1,6]naphthyridin-2-one;

1-Ethyl-7-{4-[4-(3-(hydroxy)propyl)piperidin-1-yl]phenylamino}-3,4-dihydro-1H-[1,6]naphthyridin-2-one;

7-{4-[4-(3-(Hydroxy)propyl)piperidin-1-yl]phenylamino}-1-isopropyl-3,4-dihydro-1H-[1,6]naphthyridin-2-one;

7-{4-[4-(3-(Hydroxy)propyl)piperidin-1-yl]phenylamino}-1-isopentyl-3,4-dihydro-1H-[1,6]naphthyridin-2-one;

1-Cyclopentyl-7-{4-[4-(3-(hydroxy)propyl)piperidin-1-yl]phenylamino}-3,4-dihydro-1H-[1,6]naphthyridin-2-one;

1-Cyclohexyl-7-{4-[4-(3-(hydroxy)propyl)piperidin-1-yl]phenylamino}-3,4-dihydro-1H-[1,6]naphthyridin-2-one;

1-Cycloheptyl-7-{4-[4-(3-hydroxy)propyl)piperidin-1-yl]phenylamino}-3,4-dihydro-1H-[1,6]naphthyridin-2-one;

1-Bicyclo[2.2.1]hept-2-yl-7-{4-[4-(3-(hydroxy)propyl)piperidin-1-yl]phenylamino}-3,4-dihydro-1H-[1,6]naphthyridin-2-one;

1-Methyl-7-(4-(pyrazol-1-yl)phenylamino)-3,4-dihydro-1H-[1,6]naphthyridin-2-one;

1-Ethyl-7-(4-(pyrazol-1-yl)phenylamino)-3,4-dihydro-1H-[1,6]naphthyridin-2-one;

1-Isopropyl-7-(4-(pyrazol-1-yl)phenylamino)-3,4-dihydro-1H-[1,6]naphthyridin-2-one;

1-Isopentyl-7-(4-(pyrazol-1-yl)phenylamino)-3,4-dihydro-1H-[1,6]naphthyridin-2-one;

1-Cyclopentyl-7-(4-(pyrazol-1-yl)phenylamino)-3,4-dihydro-1H-[1,6]naphthyridin-2-one;

1-Cyclohexyl-7-(4-(pyrazol-1-yl)phenylamino)-3,4-dihydro-1H-[1,6]naphthyridin-2-one;

1-Cycloheptyl-7-(4-(pyrazol-1-yl)phenylamino)-3,4-dihydro-1H-[1,6]naphthyridin-2-one;

1-Bicyclo[2.2.1]hept-2-yl-7-(4-(pyrazol-1-yl)phenylamino)-3,4-dihydro-1H-[1,6]naphthyridin-2-one;

7-(4-Fluorophenylamino)-1-methyl-3,4-dihydro-1H-[1,6]naphthyridin-2-one;

1-Ethyl-7-(4-fluorophenylamino)-3,4-dihydro-1H-[1,6]naphthyridin-2-one;

7-(4-Fluorophenylamino)-1-isopropyl-3,4-dihydro-1H-[1,6]naphthyridin-2-one;

7-(4-Fluorophenylamino)-1-isopentyl-3,4-dihydro-1H-[1,6]naphthyridin-2-one;

1-Cyclopentyl-7-(4-fluorophenylamino)-3,4-dihydro-1H-[1,6]naphthyridin-2-one;

1-Cyclohexyl-7-(4-fluorophenylamino)-3,4-dihydro-1H-[1,6]naphthyridin-2-one;

1-Cycloheptyl-7-(4-fluorophenylamino)-3,4-dihydro-1H-[1,6]naphthyridin-2-one;

1-Bicyclo[2.2.1]hept-2-yl-7-(4-fluorophenylamino)-3,4-dihydro-1H-[1,6]naphthyridin-2-one;

7-[4-(4-(Hydroxy)piperidin-1-yl)phenylamino]-1-methyl-3,4-dihydro-1H-[1,6]naphthyridin-2-one;

1-Ethyl-7-[4-(4-(hydroxy)piperidin-1-yl)phenylamino]-3,4-dihydro-1H-[1,6]naphthyridin-2-one;

7-[4-(4-(Hydroxy)piperidin-1-yl)phenylamino]-1-isopropyl-3,4-dihydro-1H-[1,6]naphthyridin-2-one;

7-[4-(4-(Hydroxy)piperidin-1-yl)phenyl amino]-1-isopentyl-3,4-dihydro-1H-[1,6]naphthyridin-2-one;

1-Cyclopentyl-7-[4-(4-(hydroxy)piperidin-1-yl)phenylamino]-3,4-dihydro-1H-[1,6]naphthyridin-2-one;

1-Cyclohexyl-7-[4-(4-(hydroxy)piperidin-1-yl)phenylamino]-3,4-dihydro-1H-[1,6]naphthyridin-2-one;

1-Cycloheptyl-7-[4-(4-(hydroxy)piperidin-1-yl)phenylamino]-3,4-dihydro-1H-[1,6]naphthyridin-2-one;

1-Bicyclo[2.2.1]hept-2-yl-7-[4-(4-(hydroxy)piperidin-1-yl)phenylamino]-3,4-dihydro-1H-[1,6]naphthyridin-2-one;

7-[4-(3-(Hydroxymethyl)piperidin-1-yl)phenylamino]-1-methyl-3,4-dihydro-1H-[1,6]naphthyridin-2-one;

1-Ethyl-7-[4-(3-(hydroxymethyl)piperidin-1-yl)phenylamino]-3,4-dihydro-1H-[1,6]naphthyridin-2-one;

7-[4-(3-(Hydroxymethyl)piperidin-1-yl)phenylamino]-1-isopropyl-3,4-dihydro-1H-[1,6]naphthyridin-2-one;

7-[4-(3-(Hydroxymethyl)piperidin-1-yl)phenylamino]-1-isopentyl-3,4-dihydro-1H-[1,6]naphthyridin-2-one;

1-Cyclopentyl-7-[4-(3-(hydroxymethyl)piperidin-1-yl)phenylamino]-3,4-dihydro-1H-[1,6]naphthyridin-2-one;

1-Cyclohexyl-7-[4-(3-(hydroxymethyl)piperidin-1-yl)phenylamino]-3,4-dihydro-1H-[1,6]naphthyridin-2-one;

1-Cycloheptyl-7-[4-(3-(hydroxymethyl)piperidin-1-yl)phenylamino]-3,4-dihydro-1H-[1,6]naphthyridin-2-one;

1-Bicyclo[2.2.1]hept-2-yl-7-[4-(3-(hydroxymethyl)piperidin-1-yl)phenylamino]-3,4-dihydro-1H-[1,6]naphthyridin-2-one;

1-Methyl-7-[4-(2H-tetrazol-5-yl)phenylamino]-3,4-dihydro-1H-[1,6]naphthyridin-2-one;

1-Ethyl-7-[4-(2H-tetrazol-5-yl)phenylamino]-3,4-dihydro-1H-[1,6]naphthyridin-2-one;

1-Isopropyl-7-[4-(2H-tetrazol-5-yl)phenylamino]-3,4-dihydro-1H-[1,6]naphthyridin-2-one;

1-Isopentyl-7-[4-(2H-tetrazol-5-yl)phenylamino]-3,4-dihydro-1H-[1,6]naphthyridin-2-one;

1-Cyclopentyl-7-[4-(2H-tetrazol-5-yl)phenylamino]-3,4-dihydro-1H-[1,6]naphthyridin-2-one;

1-Cyclohexyl-7-[4-(2H-tetrazol-5-yl)phenylamino]-3,4-dihydro-1H-[1,6]naphthyridin-2-one;

1-Cycloheptyl-7-[4-(2H-tetrazol-5-yl)phenylamino]-3,4-dihydro-1H-[1,6]naphthyridin-2-one;

1-Bicyclo[2.2.1]hept-2-yl-7-[4-(2H-tetrazol-5-yl)phenylamino]-3,4-dihydro-1H-[1,6]naphthyridin-2-one;

1-Methyl-7-(4-(piperidin-1-yl)phenylamino)-3,4-dihydro-1H-[1,6]naphthyridin-2-one;

1-Ethyl-7-(4-(piperidin-1-yl)phenylamino)-3,4-dihydro-1H-[1,6]naphthyridin-2-one;

1-Isopropyl-7-(4-(piperidin-1-yl)phenylamino)-3,4-dihydro-1H-[1,6]naphthyridin-2-one;

1-Isopentyl-7-(4-(piperidin-1-yl)phenylamino)-3,4-dihydro-1H-[1,6]naphthyridin-2-one;

1-Cyclopentyl-7-(4-(piperidin-1-yl)phenylamino)-3,4-dihydro-1H-[1,6]naphthyridin-2-one;

1-Cyclohexyl-7-(4-(piperidin-1-yl)phenylamino)-3,4-dihydro-1H-[1,6]naphthyridin-2-one;

1-Cycloheptyl-7-(4-(piperidin-1-yl)phenylamino)-3,4-dihydro-1H-[1,6]naphthyridin-2-one;

1-Bicyclo[2.2.1]hept-2-yl-7-(4-(piperidin-1-yl)phenylamino)-3,4-dihydro-1H-[1,6]naphthyridin-2-one;

1-Methyl-7-(4-(pyrrolidin-1-yl)phenylamino)-3,4-dihydro-1H-[1,6]naphthyridin-2-one;

1-Ethyl-7-(4-(pyrrolidin-1-yl)phenylamino)-3,4-dihydro-1H-[1,6]naphthyridin-2-one;

1-Isopropyl-7-(4-(pyrrolidin-1-yl)phenylamino)-3,4-dihydro-1H-[1,6]naphthyridin-2-one;

1-Isopentyl-7-(4-(pyrrolidin-1-yl)phenylamino)-3,4-dihydro-1H-[1,6]naphthyridin-2-one;

1-Cyclopentyl-7-(4-(pyrrolidin-1-yl)phenylamino)-3,4-dihydro-1H-[1,6]naphthyridin-2-one;

1-Cyclohexyl-7-(4-(pyrrolidin-1-yl)phenylamino)-3,4-dihydro-1H-[1,6]naphthyridin-2-one;

1-Cycloheptyl-7-(4-(pyrrolidin-1-yl)phenylamino)-3,4-dihydro-1H-[1,6]naphthyridin-2-one;

1-Bicyclo[2.2.1]hept-2-yl-7-(4-(pyrrolidin-1-yl)phenylamino)-3,4-dihydro-1H-[1,6]naphthyridin-2-one;

3-Fluoro-1-methyl-7-[4-(4-methylpiperazin-1-yl)phenylamino]-1H-[1,6]naphthyridin-2-one;

1-Ethyl-3-fluoro-7-[4-(4-methylpiperazin-1-yl)phenylamino]-1H-[1,6]naphthyridin-2-one;

3-Fluoro-1-isopropyl-7-[4-(4-methylpiperazin-1-yl)phenylamino]-1H-[1,6]naphthyridin-2-one;

3-Fluoro-1-isopentyl-7-[4-(4-methylpiperazin-1-yl)phenylamino]-1H-[1,6]naphthyridin-2-one;

1-Cyclopentyl-3-fluoro-7-[4-(4-methylpiperazin-1-yl)phenylamino]-1H-[1,6]naphthyridin-2-one;

1-Cyclohexyl-3-fluoro-7-[4-(4-methylpiperazin-1-yl)phenylamino]-1H-[1,6]naphthyridin-2-one; p1
1-Cycloheptyl-3-fluoro-7-[4-(4-methylpiperazin-1-yl)phenylamino]-1H-[1,6]naphthyridin-2-one;

1-Bicyclo[2.2.1]hept-2-yl-3-fluoro-7-[4-(4-methylpiperazin-1-yl)phenylamino]-1H-[1,6]naphthyridin-2-one;

3-Fluoro-1-methyl-7-{4-[4-(3-(morpholin-4-yl)propyl)piperidin-1-yl]phenylamino}-1H-[1,6]naphthyridin-2-one;

1-Ethyl-3-fluoro-7-{4-[4-(3-(morpholin-4-yl)propyl)piperidin-1-yl]phenylamino}-1H-[1,6]naphthyridin-2-one;

3-Fluoro-1-isopropyl-7-{4-[4-(3-(morpholin-4-yl)propyl)piperidin-1-yl]phenylamino}-1H-[1,6]naphthyridin-2-one;

3-Fluoro-1-isopentyl-7-{4-[4-(3-(morpholin-4-yl)propyl)piperidin-1-yl]phenylamino}-1H-[1,6]naphthyridin-2-one;

1-Cyclopentyl-3-fluoro-7-{4-[4-(3-(morpholin-4-yl)propyl)piperidin-1-yl]phenylamino}-1H-[1,6]naphthyridin-2-one;

1-Cyclohexyl-3-fluoro-7-{4-[4-(3-(morpholin-4-yl)propyl)piperidin-1-yl]phenylamino}-1H-[1,6]naphthyridin-2-one;

1-Cycloheptyl-3-fluoro-7-{4-[4-(3-(morpholin-4-yl)propyl)piperidin-1-yl]phenylamino}-1H-[1,6]naphthyridin-2-one;

1-Bicyclo[2.2.1]hept-2-yl-3-fluoro-7-{4-[4-(3-(morpholin-4-yl)propyl)piperidin-1-yl]phenylamino}-1H-[1,6]naphthyridin-2-one;

3-Fluoro-1-methyl-7-{4-[4-(3-(hydroxy)propyl)piperidin-1-yl]phenylamino}-1H-[1,6]naphthyridin-2-one;

1-Ethyl-3-fluoro-7-{4-[4-(3-(hydroxy)propyl)piperidin-1-yl]phenylamino}-1H-[1,6]naphthyridin-2-one;

3-Fluoro-7-{4-[4-(3-(hydroxy)propyl)piperidin-1-yl]phenylamino}-1-isopropyl-1H-[1,6]naphthyridin-2-one;

3-Fluoro-7-{4-[4-(3-(hydroxy)propyl)piperidin-1-yl]phenylamino}-1-isopentyl-1H-[1,6]naphthyridin-2-one;

1-Cyclopentyl-3-fluoro-7-{4-[4-(3-(hydroxy)propyl)piperidin-1-yl]phenylamino}-1H-[1,6]naphthyridin-2-one;

1-Cyclohexyl-3-fluoro-7-{4-[4-(3-(hydroxy)propyl)piperidin-1-yl]phenylamino}-1H-[1,6]naphthyridin-2-one;

1-Cycloheptyl-3-fluoro-7-{4-[4-(3-(hydroxy)propyl)piperidin-1-yl]phenylamino}-1H-[1,6]naphthyridin-2-one;

1-Bicyclo[2.2.1]hept-2-yl-3-fluoro-7-{4-[4-(3-(hydroxy)propyl)piperidin-1-yl]phenylamino}-1H-[1,6]naphthyridin-2-one;

3-Fluoro-1-methyl-7-(4-(pyrazol-1-yl)phenylamino)-1H-[1,6]naphthyridin-2-one;

1-Ethyl-3-fluoro-7-(4-(pyrazol-1-yl)phenylamino)-1H-[1,6]naphthyridin-2-one;

3-Fluoro-1-isopropyl-7-(4-(pyrazol-1-yl)phenylamino)-1H-[1,6]naphthyridin-2-one;

3-Fluoro-1-isopentyl-7-(4-(pyrazol-1-yl)phenylamino)-1H-[1,6]naphthyridin-2-one;

1-Cyclopentyl-3-fluoro-7-(4-(pyrazol-1-yl)phenylamino)-1H-[1,6]naphthyridin-2-one;

1-Cyclohexyl-3-fluoro-7-(4-(pyrazol-1-yl)phenylamino)-1H-[1,6]naphthyridin-2-one;

1-Cycloheptyl-3-fluoro-7-(4-(pyrazol-1-yl)phenylamino)-1H-[1,6]naphthyridin-2-one;

1-Bicyclo[2.2.1]hept-2-yl-3-fluoro-7-(4-(pyrazol-1-yl)phenylamino)-1H-[1,6]naphthyridin-2-one;

3-Fluoro-7-(4-fluorophenylamino)-1-methyl-1H-[1,6]naphthyridin-2-one;

1-Ethyl-3-fluoro-7-(4-fluorophenylamino)-1H-[1,6]naphthyridin-2-one;

3-Fluoro-7-(4-fluorophenylamino)-1-isopropyl-1H-[1,6]naphthyridin-2-one;

3-Fluoro-7-(4-fluorophenylamino)-1-isopentyl-1H-[1,6]naphthyridin-2-one;

1-Cyclopentyl-3-fluoro-7-(4-fluorophenylamino)-1H-[1,6]naphthyridin-2-one;

1-Cyclohexyl-3-fluoro-7-(4-fluorophenylamino)-1H-[1,6]naphthyridin-2-one;

1-Cycloheptyl-3-fluoro-7-(4-fluorophenylamino)-1H-[1,6]naphthyridin-2-one;

1-Bicyclo[2.2.1]hept-2-yl-3-fluoro-7-(4-fluorophenylamino)-1H-[1,6]naphthyridin-2-one;

3-Fluoro-7-[4-(4-(hydroxy)piperidin-1-yl)phenylamino]-1-methyl-1H-[1,6]naphthyridin-2-one;

1-Ethyl-3-fluoro-7-[4-(4-(hydroxy)piperidin-1-yl)phenylamino]-1H-[1,6]naphthyridin-2-one;

3-Fluoro-7-[4-(4-(hydroxy)piperidin-1-yl)phenylamino]-1-isopropyl-1H-[1,6]naphthyridin-2-one;

3-Fluoro-7-[4-(4-(hydroxy)piperidin-1-yl)phenylamino]-1-isopentyl-1H-[1,6]naphthyridin-2-one;

1-Cyclopentyl-3-fluoro-7-[4-(4-(hydroxy)piperidin-1-yl)phenylamino]-1H-[1,6]naphthyridin-2-one;

1-Cyclohexyl-3-fluoro-7-[4-(4-(hydroxy)piperidin-1-yl)phenylamino]-1H-[1,6]naphthyridin-2-one;

1-Cycloheptyl-3-fluoro-7-[4-(4-(hydroxy)piperidin-1-yl)phenylamino]-1H-[1,6]naphthyridin-2-one;

1-Bicyclo[2.2.1]hept-2-yl-3-fluoro-7-[4-(4-(hydroxy)piperidin-1-yl)phenylamino]-1H-[1,6]naphthyridin-2-one;

3-Fluoro-7-[4-(3-(hydroxymethyl)piperidin-1-yl)phenylamino]-1-methyl-1H-[1,6]naphthyridin-2-one;

1-Ethyl-3-fluoro-7-[4-(3-(hydroxymethyl)piperidin-1-yl)phenylamino]-1H-[1,6]naphthyridin-2-one;

3-Fluoro-7-[4-(3-(hydroxymethyl)piperidin-1-yl)phenylamino]-1-isopropyl-1H-[1,6]naphthyridin-2-one;

3-Fluoro-7-[4-(3-(hydroxymethyl)piperidin-1-yl)phenylamino]-1-isopentyl-1H-[1,6]naphthyridin-2-one;

1-Cyclopentyl-3-fluoro-7-[4-(3-(hydroxymethyl)piperidin-1-yl)phenylamino]-1H-[1,6]naphthyridin-2-one;

1-Cyclohexyl-3-fluoro-7-[4-(3-(hydroxymethyl)piperidin-1-yl)phenylamino]-1H-[1,6]naphthyridin-2-one;

1-Cycloheptyl-3-fluoro-7-[4-(3-(hydroxymethyl)piperidin-1-yl)phenylamino]-1H-[1,6]naphthyridin-2-one;

1-Bicyclo[2.2.1]hept-2-yl-3-fluoro-7-[4-(3-(hydroxymethyl)piperidin-1-yl)phenylamino]-1H-[1,6]naphthyridin-2-one;

3-Fluoro-1-methyl-7-[4-(2H-tetrazol-5-yl)phenylamino]-1H-[1,6]naphthyridin-2-one;

1-Ethyl-3-fluoro-7-[4-(2H-tetrazol-5-yl)phenylamino]-1H-[1,6]naphthyridin-2-one;

3-Fluoro-1-isopropyl-7-[4-(2H-tetrazol-5-yl)phenylamino]-1H-[1,6]naphthyridin-2-one;

3-Fluoro-1-isopentyl-7-[4-(2H-tetrazol-5-yl)phenylamino]-1H-[1,6]naphthyridin-2-one;

1-Cyclopentyl-3-fluoro-7-[4-(2H-tetrazol-5-yl)phenylamino]-1H-[1,6]naphthyridin-2-one;

1-Cyclohexyl-3-fluoro-7-[4-(2H-tetrazol-5-yl)phenylamino]-1H-[1,6]naphthyridin-2-one;

1-Cycloheptyl-3-fluoro-7-[4-(2H-tetrazol-5-yl)phenylamino]-1H-[1,6]naphthyridin-2-one;

1-Bicyclo[2.2.1]hept-2-yl-3-fluoro-7-[4-(2H-tetrazol-5-yl)phenylamino]-1H-[1,6]naphthyridin-2-one;

3-Fluoro-1-methyl-7-(4-(piperidin-1-yl)phenylamino)-1H-[1,6]naphthyridin-2-one;

1-Ethyl-3-fluoro-7-(4-(piperidin-1-yl)phenylamino)-1H-[1,6]naphthyridin-2-one;

3-Fluoro-1-isopropyl-7-(4-(piperidin-1-yl)phenylamino)-1H-[1,6]naphthyridin-2-one;

3-Fluoro-1-isopentyl-7-(4-(piperidin-1-yl)phenylamino)-1H-[1,6]naphthyridin-2-one;

1-Cyclopentyl-3-fluoro-7-(4-(piperidin-1-yl)phenylamino)-1H-[1,6]naphthyridin-2-one;

1-Cyclohexyl-3-fluoro-7-(4-(piperidin-1-yl)phenylamino)-1H-[1,6]naphthyridin-2-one;

1-Cycloheptyl-3-fluoro-7-(4-(piperidin-1-yl)phenylamino)-1H-[1,6]naphthyridin-2-one;

1-Bicyclo[2.2.1]hept-2-yl-3-fluoro-7-(4-(piperidin-1-yl)phenylamino)-1H-[1,6]naphthyridin-2-one;

3-Fluoro-1-methyl-7-(4-(pyrrolidin-1-yl)phenylamino)-1H-[1,6]naphthyridin-2-one;

1-Ethyl-3-fluoro-7-(4-(pyrrolidin-1-yl)phenylamino)-1H-[1,6]naphthyridin-2-one;

3-Fluoro-1-isopropyl-7-(4-(pyrrolidin-1-yl)phenylamino)-1H-[1,6]naphthyridin-2-one;

3-Fluoro-1-isopentyl-7-(4-(pyrrolidin-1-yl)phenylamino)-1H-[1,6]naphthyridin-2-one;

1-Cyclopentyl-3-fluoro-7-(4-(pyrrolidin-1-yl)phenylamino)-1H-[1,6]naphthyridin-2-one;

1-Cyclohexyl-3-fluoro-7-(4-(pyrrolidin-1-yl)phenylamino)-1H-[1,6]naphthyridin-2-one;

1-Cycloheptyl-3-fluoro-7-(4-(pyrrolidin-1-yl)phenylamino)-1H-[1,6]naphthyridin-2-one;

1-Bicyclo [2.2.1]hept-2-yl-3-fluoro-7-(4-(pyrrolidin-1-yl)phenylamino)-1H-[1,6]naphthyridin-2-one;

3-(2,6-Dichlorophenyl)-7-(4-fluoro-3-methylphenylamino)-1-methyl-1H-[1,6]naphthyridin-2-one;

3-(2,6-Dichlorophenyl)-7-(4-ethoxyphenylamino)-1-methyl-1H-[1,6]naphthyridin-2-one;

3-(2,6-Dichlorophenyl)-7-(3-(hydroxymethyl)phenylamino)-1-methyl-1H-[1,6]naphthyridin-2-one;

3-(2,6-Dichlorophenyl)-1-methyl-7-(4-(morpholin-4-yl)phenylamino)-1H-[1,6]naphthyridin-2-one;

3-(2,6-Dichlorophenyl)-1-methyl-7-[4-(2-(morpholin-4-yl)ethoxy)phenylamino]-1H-[1,6]naphthyridin-2-one;

3-(2,6-Dichlorophenyl)-1-methyl-7-[4-(2-(piperidin-1-yl)ethoxy)phenylamino]-1H-[1,6]naphthyridin-2-one;

3-(2,6-Dichlorophenyl)-1-methyl-7-[4-(4-(methylpiperazin-1-yl)methyl)phenylamino]-1H-[1,6]naphthyridin-2-one;

3-(2,6-Dichlorophenyl)-7-[4-(2-(dimethylamino)ethoxy)phenylamino]-1-methyl-1H-[1,6]naphthyridin-2-one;

3-[3-(2,6-Dichlorophenyl)-1-methyl-2-oxo-1,2-dihydro-[1,6]naphthyridin-7-ylamino]-benzoic acid;

3-(2,6-Dichlorophenyl)-7-[3-(2-(diethylamino)ethoxy)phenylamino]-1-methyl-1H-[1,6]naphthyridin-2-one;

N-(2-{4-[3-(2,6-Dichlorophenyl)-1-methyl-2-oxo-1,2-dihydro-[1,6]naphthyridin-7-ylamino]phenoxy}ethyl)-N-ethyl-acetamide;

{4-[3-(2,6-Dichlorophenyl)-1-methyl-2-oxo-1,2-dihydro-[1,6]naphthyridin-7-ylamino]phenyl}-acetic acid;

3-(2,6-Dichlorophenyl)-1-ethyl-7-(4-fluoro-3-methylphenylamino)-1H-[1,6]naphthyridin-2-one;

3-(2,6-Dichlorophenyl)-7-(4-ethoxyphenylamino)-1-ethyl-1H-[1,6]naphthyridin-2-one;

3-(2,6-Dichlorophenyl)-1-ethyl-7-(3-(hydroxymethyl)phenylamino)-1H-[1,6]naphthyridin-2-one;

3-(2,6-Dichlorophenyl)-1-ethyl-7-(4-(morpholin-4-yl)phenylamino)-1H-[1,6]naphthyridin-2-one;

3-(2,6-Dichlorophenyl)-7-[4-(2-(diethylamino)ethoxy)phenylamino]-1-ethyl-1H-[1,6]naphthyridin-2-one;

3-(2,6-Dichlorophenyl)-1-ethyl-7-[4-(2-(morpholin-4-yl)ethoxy)phenylamino]-1H-[1,6]naphthyridin-2-one;

3-(2,6-Dichlorophenyl)-1-ethyl-7-[4-(2-(piperidin-1-yl)ethoxy)phenylamino]-1H-[1,6]naphthyridin-2-one;

3-(2,6-Dichlorophenyl)-1-ethyl-7-[4-(4-(methylpiperazin-1-yl)methyl)phenylamino]-1H-[1,6]naphthyridin-2-one;

3-(2,6-Dichlorophenyl)-7-[4-(2-(dimethylamino)ethoxy)phenylamino]-1-ethyl-1H-[1,6]naphthyridin-2-one;

3-[3-(2,6-Dichlorophenyl)-1-ethyl-2-oxo-1,2-dihydro-[1,6]naphthyridin-7-ylamino]-benzoic acid;

3-(2,6-Dichlorophenyl)-7-[3-(2-(diethylamino)ethoxy)phenylamino]-1-ethyl-1H-[1,6]naphthyridin-2-one;

N-(2-{4-[3-(2,6-Dichlorophenyl)-1-ethyl-2-oxo-1,2-dihydro-[1,6]naphthyridin-7-ylamino]phenoxy}ethyl)-N-ethyl-acetamide;

3-(2,6-Dichlorophenyl)-1-ethyl-7-(4-pyridylamino)-1H-[1,6]naphthyridin-2-one;

3-(2,6-Dichlorophenyl)-1-ethyl-7-[4-(4-methylpiperazin-1-yl)phenylamino]-1H-[1,6]naphthyridin-2-one;

{4-[3-(2,6-Dichlorophenyl)-1-ethyl-2-oxo-1,2-dihydro-[1,6]naphthyridin-7-ylamino]phenyl}-acetic acid;

3-(3,5-Dimethoxyphenyl)-1-methyl-7-[3-(4-methylpiperazin-1-yl)propylamino]-1H-[1,6]naphthyridin-2-one;

3-(3,5-Dimethoxyphenyl)-1-ethyl-7-[3-(4-methylpiperazin-1-yl)propylamino]-1H-[1,6]naphthyridin-2-one;

7-(4-(Diethylamino)butylamino)-3-(3,5-dimethoxyphenyl)-1-methyl-1H-[1,6]naphthyridin-2-one;

7-(4-(Diethylamino)butylamino)-3-(3,5-dimethoxyphenyl)-1-ethyl-1H-[1,6]naphthyridin-2-one;

7-[4-(2-(Diethylamino)ethoxy)phenylamino]-3-(3,5-dimethoxyphenyl)-1-ethyl-1H-[1,6]naphthyridin-2-one;

7-[4-(2-(Diethylamino)ethoxy)phenylamino]-3-(3,5-dimethoxyphenyl)-1-methyl-1H-[1,6]naphthyridin-2-one;

3-(3,5-Dimethoxyphenyl)-1-ethyl-7-(4-pyridylamino)-1H-[1,6]naphthyridin-2-one;

3-(3,5-Dimethoxyphenyl)-1-methyl-7-(4-pyridylamino)-1H-[1,6]naphthyridin-2-one;

3-(2,6-Dichloro-3,5-dimethoxyphenyl)-1-methyl-7-[3-(4-methylpiperazin-1-yl)propylamino]-1H-[1,6]naphthyridin-2-one;

3-(2-Chloro-3,5-dimethoxyphenyl)-1-methyl-7-[3-(4-methylpiperazin-1-yl)propylamino]-1H-[1,6]naphthyridin-2-one;

3-(2,6-Dimethyl-3,5-dimethoxyphenyl)-1-methyl-7-[3-(4-methylpiperazin-1-yl)propylamino]-1H-[1,6]naphthyridin-2-one;

1-Methyl-3-(2-methyl-3,5-dimethoxyphenyl)-7-[3-(4-methylpiperazin-1-yl)propylamino]-1H-[1,6]naphthyridin-2-one;

3-(2,6-Dichloro-3,5-dimethoxyphenyl)-1-ethyl-7-[3-(4-methylpiperazin-1-yl)propylamino]-1H-[1,6]naphthyridin-2-one;

3-(2-Chloro-3,5-dimethoxyphenyl)-1-ethyl-7-[3-(4-methylpiperazin-1-yl)propylamino]-1H-[1,6]naphthyridin-2-one;

3-(2,6-Dimethyl-3,5-dimethoxyphenyl)-1-ethyl-7-[3-(4-methylpiperazin-1-yl)propylamino]-1H-[1,6]naphthyridin-2-one;

1-Ethyl-3-(2-methyl-3,5-dimethoxyphenyl)-7-[3-(4-methylpiperazin-1-yl)propylamino]-1H-[1,6]naphthyridin-2-one;

3-(2,6-Dichloro-3,5-dimethoxyphenyl)-7-(4-(diethylamino)butylamino)-1-methyl-1H-[1,6]naphthyridin-2-one;

3-(2-Chloro-3,5-dimethoxyphenyl)-7-(4-(diethylamino)butylamino)-1-methyl-1H-[1,6]naphthyridin-2-one;

7-(4-(Diethylamino)butylamino)-1-methyl-3-(2-methyl-3,5-dimethoxyphenyl)-1H-[1,6]naphthyridin-2-one;

3-(2,6-Dimethyl-3,5-dimethoxyphenyl)-7-(4-(diethylamino)butylamino)-1-methyl-1H-[1,6]naphthyridin-2-one;

3-(2,6-Dichloro-3,5-dimethoxyphenyl)-7-(4-(diethylamino)butylamino)-1-ethyl-1H-[1,6]naphthyridin-2-one;

3-(2-Chloro-3,5-dimethoxyphenyl)-7-(4-(diethylamino)butylamino)-1-ethyl-1H-[1,6]naphthyridin-2-one;

7-(4-(Diethylamino)butylamino)-1-ethyl-3-(2-methyl-3,5-dimethoxyphenyl)-1H-[1,6]naphthyridin-2-one;

7-(4-(Diethylamino)butylamino)-3-(2,6-dimethyl-3,5-dimethoxyphenyl)-1-ethyl-1H-[1,6]naphthyridin-2-one;

3-(2,6-Dichloro-3,5-dimethoxyphenyl)-7-[4-(2-(diethylamino)ethoxy)phenylamino]-1-methyl-1H-[1,6]naphthyridin-2-one;

3-(2-Chloro-3,5-dimethoxyphenyl)-7-[4-(2-(diethylamino)ethoxy)phenylamino]-1-methyl-1H-[1,6]naphthyridin-2-one;

7-[4-(2-(Diethylamino)ethoxy)phenylamino]-1-methyl-3-(2-methyl-3,5-dimethoxyphenyl)-1H-[1,6]naphthyridin-2-one;

3-(2,6-Dimethyl-3,5-dimethoxyphenyl)-7-[4-(2-(diethylamino)ethoxy)phenylamino]-1-methyl-1H-[1,6]naphthyridin-2-one;

3-(2,6-Dichloro-3,5-dimethoxyphenyl)-7-[4-(2-(diethylamino)ethoxy)phenylamino]-1-ethyl-1H-[1,6]naphthyridin-2-one;

3-(2-Chloro-3,5-dimethoxyphenyl)-7-[4-(2-(diethylamino)ethoxy)phenylamino]-1-ethyl-1H-[1,6]naphthyridin-2-one;

7-[4-(2-(Diethylamino)ethoxy)phenylamino]-1-ethyl-3-(2-methyl-3,5-dimethoxyphenyl)-1H-[1,6]naphthyridin-2-one;

7-[4-(2-(Diethylamino)ethoxy)phenylamino]-3-(2,6-dimethyl-3,5-dimethoxyphenyl)-1-ethyl-1H-[1,6]naphthyridin-2-one;

1-Methyl-7-[3-(4-methylpiperazin-1-yl)propylamino]-3-(2,3,5,6-tetramethylphenyl)-1H-[1,6]naphthyridin-2-one;

1-Ethyl-7-[3-(4-methylpiperazin-1-yl)propylamino]-3-(2,3,5,6-tetramethylphenyl)-1H-[1,6]naphthyridin-2-one;

7-(4-(Diethylamino)butylamino)-1-methyl-3-(2,3,5,6-tetramethylphenyl)-1H-[1,6]naphthyridin-2-one;

7-(4-(Diethylamino)butylamino)-1-ethyl-3-(2,3,5,6-tetramethylphenyl)-1H-[1,6]naphthyridin-2-one;

7-[4-(2-(Diethylamino)ethoxy)phenylamino]-1-ethyl-3-(2,3,5,6-tetramethylphenyl)-1H-[1,6]naphthyridin-2-one;

7-[4-(2-(Diethylamino)ethoxy)phenylamino]-1-methyl-3-(2,3,5,6-tetramethylphenyl)-1H-[1,6]naphthyridin-2-one;

1-Methyl-7-[3-(4-methylpiperazin-1-yl)propylamino]-3-phenyl-1H-[1,6]naphthyridin-2-one;

1-Ethyl-7-[3-(4-methylpiperazin-1-yl)propylamino]-3-phenyl-1H-[1,6]naphthyridin-2-one;

7-(4-(Diethylamino)butylamino)-1-methyl-3-phenyl-1H-[1,6]naphthyridin-2-one;

7-(4-(Diethylamino)butylamino)-1-ethyl-3-phenyl-1H-[1,6]naphthyridin-2-one;

7-[4-(2-(Diethylamino)ethoxy)phenylamino]-1-ethyl-3-phenyl-1H-[1,6]naphthyridin-2-one;

7-[4-(2-(Diethylamino)ethoxy)phenylamino]-1-methyl-3-phenyl-1H-[1,6]naphthyridin-2-one;

7-[4-(2-(Diethylamino)ethoxy)phenylamino]-1-methyl-3-(thiophen-3-yl)-1H-[1,6]naphthyridin-2-one;

7-[4-(2-(Diethylamino)ethoxy)phenylamino]-1-ethyl-3-(thiophen-3-yl)-1H-[1,6]naphthyridin-2-one;

7-[4-(2-(Diethylamino)ethoxy)phenylamino]-1-methyl-3-(thiophen-2-yl)-1H-[1,6]naphthyridin-2-one; and 7-[4-(2-(Diethylamino)ethoxy)phenylamino]-1-ethyl-3-(thiophen-2-yl)-1H-[1,6]naphthyridin-2-one.

In one preferred embodiment of the compounds of Formula I, — — is absent.

In another preferred embodiment, — — — is a bond.

In another preferred embodiment, $R^2$ is —CH$_2$CH$_3$.

In another preferred embodiment,

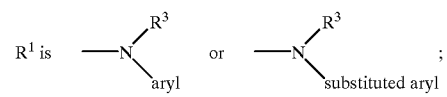

wherein aryl is phenyl and substituted aryl is substituted phenyl.

In another preferred embodiment,

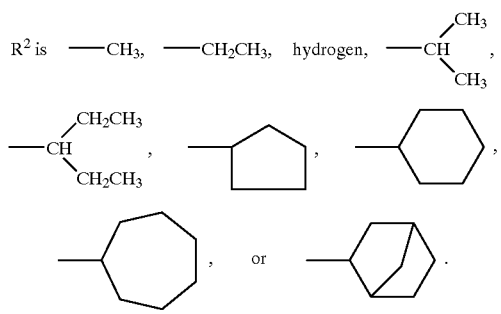

In another preferred embodiment,
R⁵ is hydrogen,
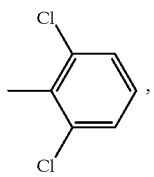
fluorine,
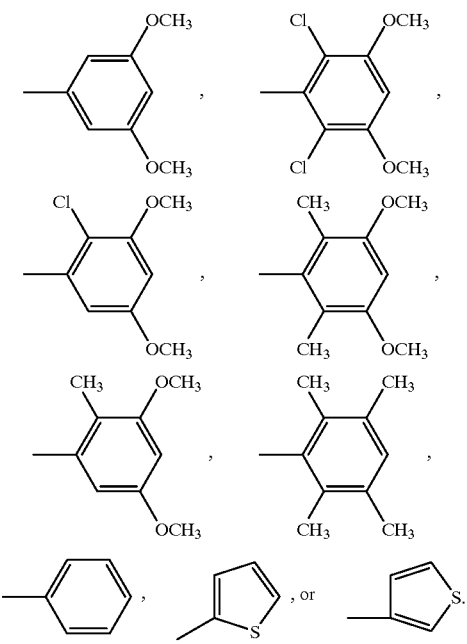
In still another preferred embodiment,
R¹ is
—NH₂,
—F,
—NH-phenyl,
—NH-substituted phenyl,
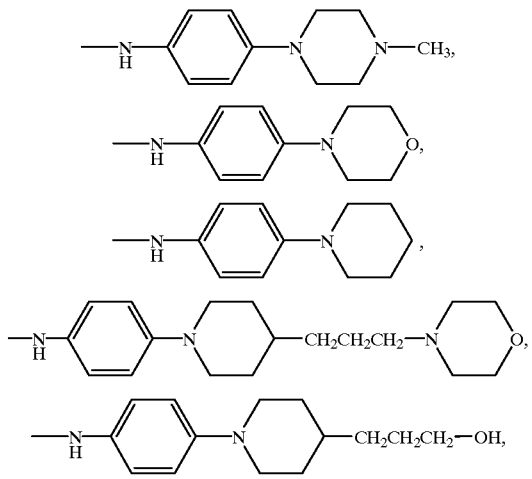
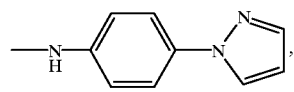
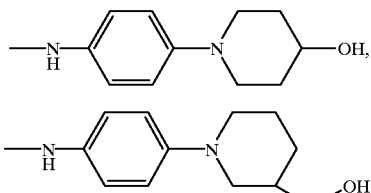
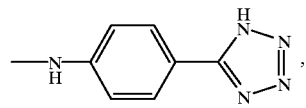
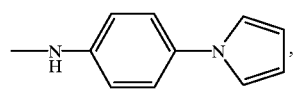
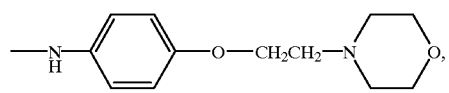
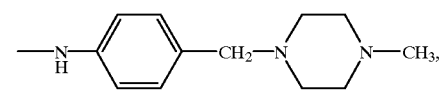
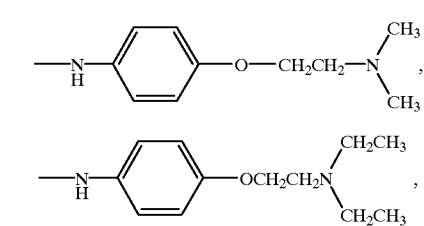
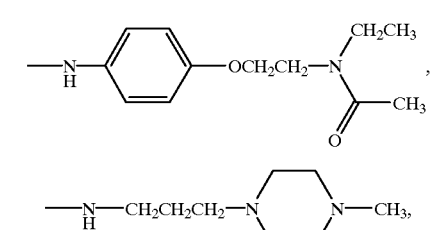
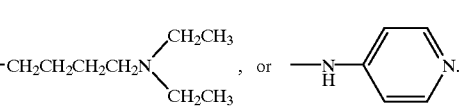
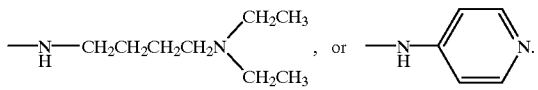
In a more preferred embodiment, the present invention provides compounds of Formula I
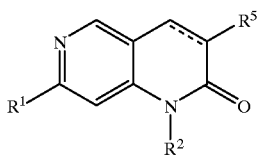
wherein
— — — is a bond or absent;

$R^1$ is
—$NH_2$,
—F,
—NH-phenyl,
—NH-substituted phenyl,

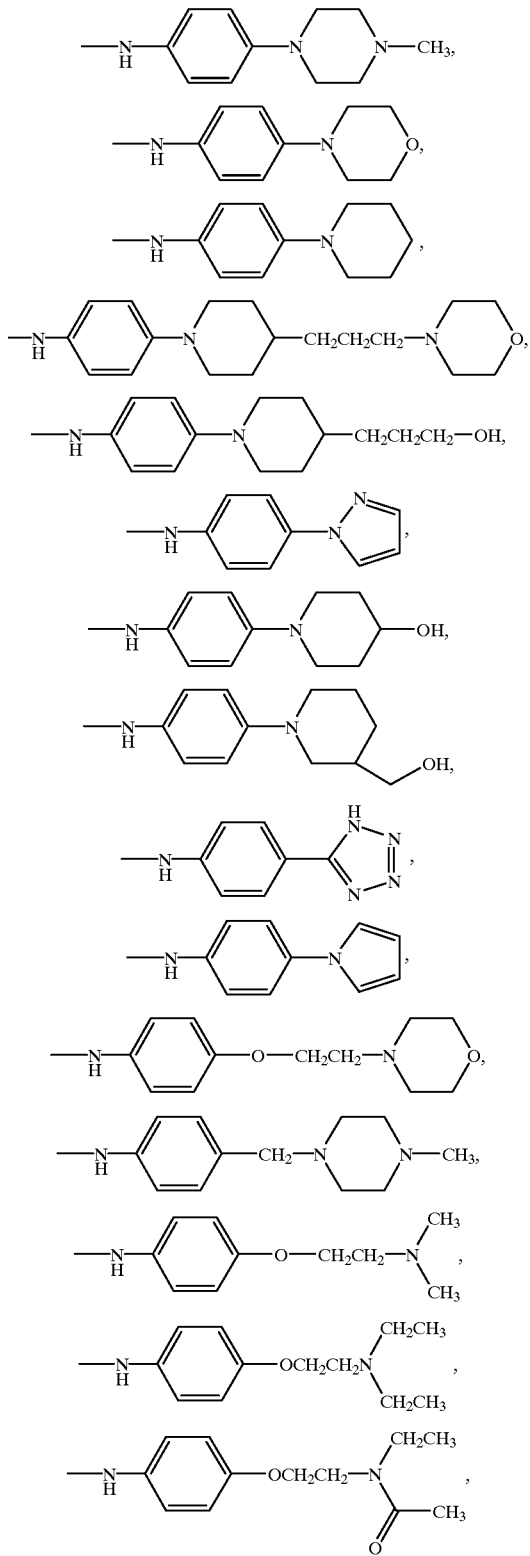

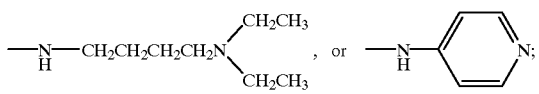

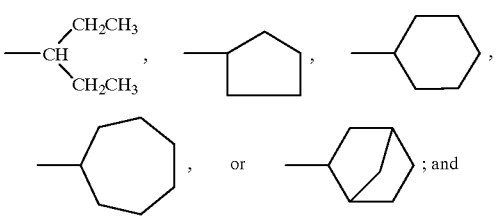

$R^2$ is —$CH_3$, —$CH_2CH_3$, hydrogen,

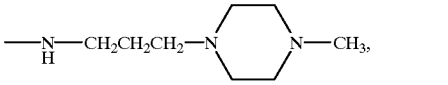

$R^5$ is
hydrogen,

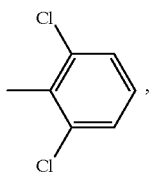

fluorine

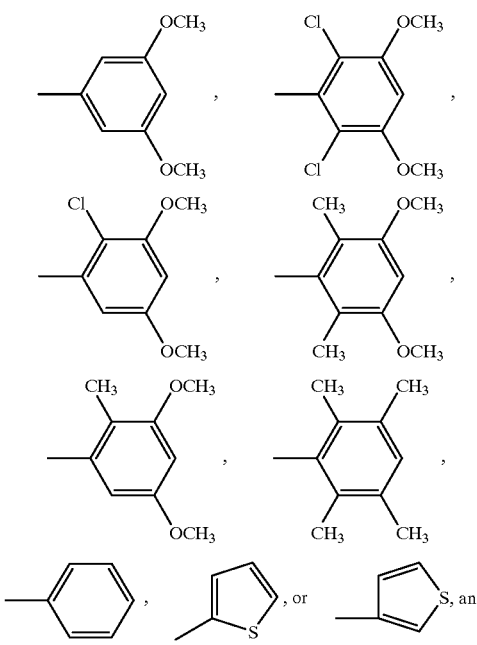

the pharmaceutically acceptable salts thereof.

Also provided by the present invention is a method of treating cancer, the method comprising administering to a patient having cancer a therapeutically effective amount of a compound of Formula I.

Also provided is a method of treating or preventing atherosclerosis, the method comprising administering to a patient having atherosclerosis or at risk of having atherosclerosis a therapeutically effective amount of a compound of Formula I.

Also provided is a method of treating or preventing restenosis, the method comprising administering to a patient having restenosis or at risk of having restenosis a therapeutically effective amount of a compound of Formula I.

Also provided is a method of treating psoriasis, the method comprising administering to a patient having psoriasis a therapeutically effective amount of a compound of Formula I.

Also provided is a method of inhibiting protein tyrosine kinases, the method comprising administering to a patient in need of protein tyrosine kinase inhibition a protein tyrosine kinase inhibiting amount of a compound of Formula I.

In a preferred embodiment of the method of inhibiting protein tyrosine kinases, the protein tyrosine kinase is c-Src.

In another preferred embodiment, the protein tyrosine kinase in PDGFr.

In another preferred embodiment, the protein tyrosine kinase is FGFr.

Also provided is a method of inhibiting cell cycle kinases, the method comprising administering to a patient in need of cell cycle kinase inhibition a cell cycle kinase inhibiting amount of a compound of Formula I.

In a preferred embodiment of the method of inhibiting cell cycle kinases, the cell cycle kinase is CDK4, CDK2, or CDK1.

Also provided by the present invention is a pharmaceutical composition that comprises a compound of Formula I.

DETAILED DESCRIPTION OF THE INVENTION

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "halogen" includes chlorine, fluorine, bromine, and iodine.

The term "alkenyl" means a branched or straight chain hydrocarbon having one; or more carbon—carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The symbol "—" means a bond.

The term "patient" means all animals including humans. Examples of patients include humans, cows, dogs, cats, goats, sheep, and pigs.

The term "substituted" means that the base organic radical has one or more substituents. For example, substituted aryl means an aryl radical such as benzene that has one or more substituents. Substituents include, but are not limited to, halogen, $C_1$–$C_8$alkyl, —CN, $CF_3$, —$NO_2$, —$NH_2$, —$NHC_1$–$C_8$alkyl, —$N(C_1$–$C_8$alkyl$)_2$, —$OC_1$–$C_8$alkyl, —OH,

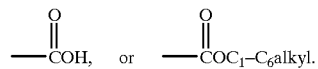

The term "heterocycle" means a cycloalkyl group wherein one, or more carbon atom is replaced with a heteroatom. Examples of heterocycles include, but are not limited to, pyrrolidinyl, piperidyl, and piperazinyl.

The term "bicycloalkyl" means a cyclic hydrocarbon having the formula

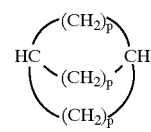

wherein each p is independently 1 to 4.

Those skilled in the art are easily able to identify patients having cancer, atherosclerosis, psoriasis, restenosis, or at risk of having atherosclerosis or restenosis. For example, patients who are at risk of having restenosis include, but are not limited to, patients having undergone balloon angioplasty or other surgical vascular procedures.

A therapeutically effective amount is an amount of a compound of Formula I, that when administered to a patient, ameliorates a symptom of the disease.

The term "cancer" includes, but is not limited to, the following cancers:

breast;
ovary;
cervix;
prostate;
testis;
esophagus;
glioblastoma;
neuroblastoma;
stomach;
skin, keratoacanthoma;
lung, epidermoid carcinoma, large cell carcinoma, adenocarcinoma;
bone;
colon, adenocarcinoma, adenoma;
pancreas, adenocarcinoma;
thyroid, follicular carcinoma, undifferentiated carcinoma, papillary carcinoma;
seminoma;
melanoma;
sarcoma;
bladder carcinoma;
liver carcinoma and biliary passages;
kidney carcinoma;
myeloid disorders;
lymphoid disorders, Hodgkin's disease, hairy cells;

buccal cavity and pharynx (oral), lip, tongue, mouth, pharynx;

small intestine;

colon-rectum, large intestine, rectum;

brain and central nervous system; and leukemia.

The compounds of the present invention can be administered to a patient either alone; or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$alkyl esters wherein the alkyl group is a straight or branched chain. Acceptable esters also include $C_5$–$C_7$cycloalkyl esters as well as arylalkyl esters such as, but not limited to benzyl. $C_1$–$C_4$alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$alkyl primary amines, and $C_1$–$C_2$dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

EXAMPLES

The compounds of Formula I can be prepared by the process described in Scheme 1 below.

General Synthesis

The dimerisation of malononitrile in the presence of HBr gives 2-bromo-3-cyano-4,6-diaminopyridine (II) as reported [W. J. Middleton, U.S. Patent, *Chem. Abstracts*, 1957;2,790, 806(51):P14829;Carboni R. A., Coffman D. D., Howard E. G., *J. Am. Chem. Soc.*, 1958;80, 2838] but in slightly better yield (typically 79%–86% for a 0.5 mole scale reaction). Hydrogenolysis of this intermediate affords 3-cyano-4,6-diaminopyridine (III) [Metzger R., Oberdorfer J., Schwager C., Thielecke W., Boldt P., *Liebigs Ann. Chem.*, 1980;946–953] in good yield (typically 80%–91%). Subsequent hydrogenation of the cyanopyridine, for example in a mixture of formic acid and water, employing Raney nickel catalyst provides the key 4,6-diamino-3-pyridylcarboxaldehyde intermediate (IV) as previously described in U.S. Pat. No. 5,620,981, issued Apr. 15, 1997, which is hereby incorporated by reference. Depending on the grade of catalyst used, it may be preferable to employ small, multiple additions of fresh catalyst over several days of reaction. The product can be isolated and purified in good yield (typically 70%) by performing multiple extractions of the (filtered and neutralised) aqueous solution with an organic solvent, for example ethyl acetate.

The aldehyde may then be condensed directly with an aryl acetonitrile to provide a 3-aryl-2,7-diamino-1,6-naphthyridine (VI), also described in U.S. Pat. No. 5,620, 981, after the manner reported by Hawes et al. [Hawes E. M., Gorecki D. K. J., *J. Heterocycl. Chem.*, 1972;9,703]. This reaction is accomplished typically in a boiling alcohol (preferably 2-ethoxyethanol) and in the presence of an alkoxide base (preferably sodium 2-ethoxyethoxide), which can be generated in situ by the addition of sodium metal or sodium hydride to the alcohol solvent. Although the use of just over one equivalent of the aryl acetonitrile and a catalytic amount of base (preferably 0.4 equivalents) in a minimal amount of solvent is sufficient for complete reaction, better yields (74%–81%) may be obtained with two equivalents of both the nitrile and the base. The desired product is separated by chromatography on a solid support (preferably silica gel) from reagent derived material and a minor by-product. This byproduct is a 7-amino-2-(arylmethyl)pyrido[4,3d]pyrimidine (V), resulting from a condensation reaction involving the nitrile itself.

The 3-aryl-2,7-diamino-1,6-naphthyridine can be converted into a 3-aryl-7-fluoro-1H-[1,6]naphthyridin-2-one; (VII) in reasonable yield (typically 50%–60%) by a diazotization reaction in 50% aqueous fluoboric acid, using a large excess (up to 8 equivalents) of solid sodium nitrite at low temperature (at or below −5° C.) for several days, after the manner previously described [Rewcastle G. W., Palmer B. D., Thompson A. M., Bridges A. J., Cody D. R., Zhou H., Fry D. J., McMichael A., Denny W. A. *J. Med. Chem.*, 1996;39,1823]. The product from this reaction is obtained by extraction into an organic solvent (preferably ethyl acetate), following careful low temperature neutralisation with an inorganic base (preferably sodium carbonate), then separation from the dione byproduct (VIII) by chromatography. This naphthyridin-2-one intermediate may be N-alkylated in high yield by treatment with an alkyl iodide in the presence of a base (preferably sodium hydride) in a suitable dry, unreactive solvent (preferably dimethylformamide) at 0 to 20° C. A small amount of the product (X) from competing O-alkylation may also be obtained and can be removed by chromatography. The resulting 1-alkyl-3-aryl-7-fluoro-1H-[1,6]naphthyridin-2-one (IX) is a versatile, reactive intermediate which can be reacted directly with either aliphatic amines in a suitable solvent (preferably 2-pentanol, or in the case of gaseous amines in 2-propanol using a suitable pressure vessel) or with certain neat aryl amines at temperatures of 90 to 175° C. for between 30 minutes to 3 days to provide the compounds of Formula I where $R^5$ is an aryl group and the dotted line is a bond. Alternatively, the same fluoro intermediate can be treated with the lithium anion of aryl amines in a suitable dry, unreactive solvent (preferably tetrahydrofuran) at −78 to 20° C. for up to 3 days to give further compounds of Formula I. These compounds are typically purified by chromatography on silica gel and/or alumina and crystallisation from suitable solvents.

The compounds of Formula I can also be prepared by the process described in Scheme 2 below.

The key 4,6-diamino-3-pyridylcarboxaldehyde intermediate (IV) can be reacted with either a stabilized phosphorane, or a phosphonate ester in the presence of a base, or any alternative Wittig or Horner-Emmons reagent to provide the corresponding unsaturated ester. The resulting double bond can be trans, cis, or a mixture of both. For example, reaction of a 4,6-diamino-3-pyridylcarboxaldehyde with an excess amount of the stabilized phosphorane (carbethoxymethylene) triphenylphosphorane in 1,4-dioxane at reflux temperature gives mainly, or in some cases exclusively, the trans unsaturated ethyl ester (XI). Upon treatment with base, ring closure occurs to give the desired 7-amino-1,6-naphthyridin-2-one (XII). This reaction can be carried out using a tertiary amine such as triethylamine or, preferably, N,N-diisopropylethylamine as the solvent, with 1 to 10 equiva-

SCHEME 1

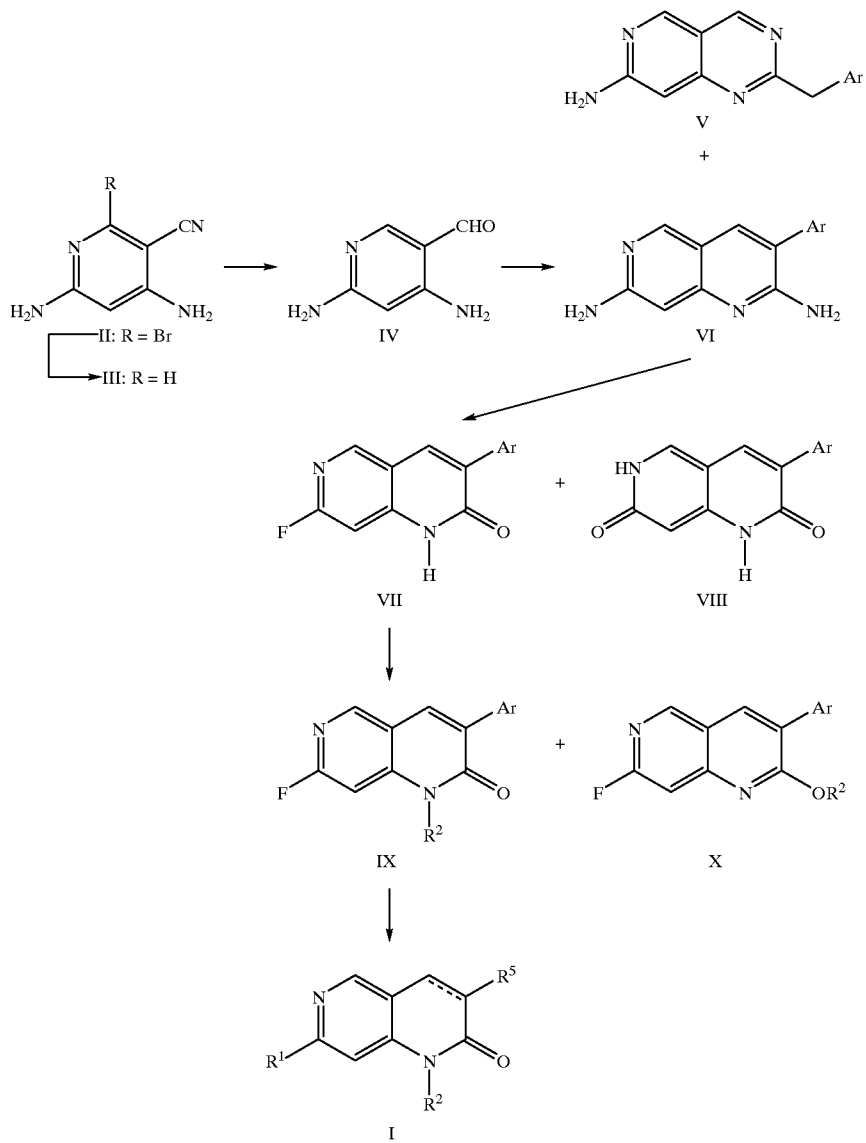

lents of 1,8-diazabicyclo[5.4.0]undec-7-ene present. The reaction is carried out at elevated temperature, and is usually complete in 2 to 24 hours. Alternatively, the 4,6-diamino-3-pyridylcarboxaldehyde can be reacted with a phosphonate ester such as bis(2,2,2-trifluoroethyl) (methoxycarbonylmethyl)-phosphonate using a strongly dissociated base (*Tetrahedron Lett.,* 1983:4405) to give predominately, if not exclusively, the cis unsaturated ester. Upon treatment with base under the conditions discussed previously, ring closure occurs.

The naphthyridin-2-one intermediate (XII) may be N-alkylated in good yield by treatment with an alkyl iodide in the presence of a base (preferably sodium hydride) in a suitable dry, unreactive solvent (preferably N,N-dimethylformamide) at 0 to 20° C. A small amount of the product (XIV) from competing O-alkylation may also be obtained and can be removed by chromatography. The resulting 1-alkyl-7-amino-1,6-naphthyridin-2-one (XIII) can be converted into a 1-alkyl-7-fluoro-1,6-naphthyridin-2-one (XV) in reasonable yield (typically 50%–60%) by a diazotization reaction in 50% aqueous fluoboric acid, using an excess of solid sodium nitrite at low temperature (at or below −5° C.) for several hours. The product from this reaction is obtained by extraction into an organic solvent (preferably ethyl acetate), following careful low temperature neutralisation with an inorganic base (preferably sodium carbonate), then purification by chromatography. The 1-alkyl-7-fluoro-1,6-naphthyridin-2-one (XV) can be reacted directly with either aliphatic amines in a suitable solvent (preferably 2-pentanol, or in the case of gaseous amines in 2-propanol using a suitable pressure vessel) or with certain neat aryl amines at temperatures of 90 to 175° C. for between 30 minutes to 3 days to provide the compounds of Formula I where $R^5$ is hydrogen and the dotted line is a bond. Alternatively, intermediate XV can be treated with the lithium anion of aryl amines in a suitable dry, non-reactive solvent (preferably tetrahydrofuran) at −78 to 20° C. for up to 3 days to give further compounds of Formula I. These compounds are typically purified by chromatography on silica gel and/or alumina and followed by crystallization from suitable solvents. Compounds of Formula I can then be transformed to the dihydro congener of Formula I, where R5 is hydrogen and the dotted line is absent, by standard methods of reduction. The preferred method is to use catalytic hydrogenation with a standard catalyst such as palladium on charcoal or Raney nickel. A range of solvents is possible for this transformation including lower alcohols, ethers, and lower alkyl amides. This transformation can also be carried out over a range of temperature and pressure.

SCHEME II

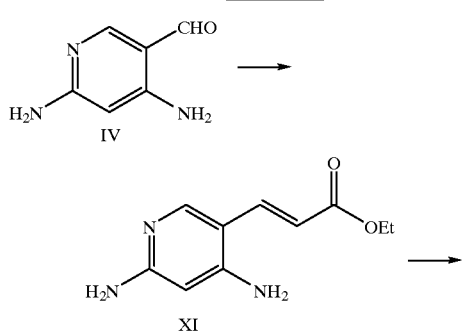

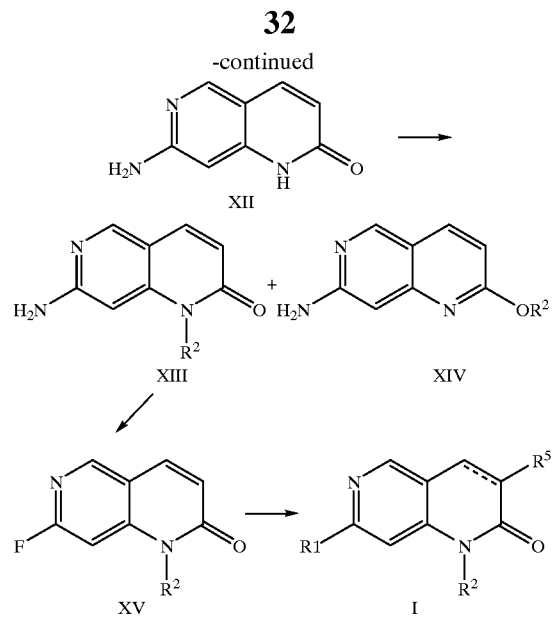

Example A

Preparation of 7-amino-3-(2,6-dichlorophenyl)-1-methyl-1H-[1,6]naphthyridin-2-one Trial 1

Anhydrous HBr (49 g, 0.60 mol) was added to a stirred mixture of malononitrile (37.5 g, 0.57 mol) and toluene (800 mL) at 0° C., then the resulting mixture was stirred at 20° C. for 16 hours, then at reflux for 2hours. The resulting solution was cooled (to 0° C.), then the solid was collected by filtration and oven dried. This material was then dissolved in water (1 L) and the solution neutralised with 40% NaOH to give (crude) 2-bromo-3-cyano-4,6-diaminopyridine (II) (51.8 g, 86%): mp (water) 215.5–218.5° C. [W. J. Middleton, U.S. Patent, *Chem. Abstracts,* 1957;2,790,806 (51):P14829 records mp (EtOH) 255° C.; Carboni R. A., Coffman D. D., Howard E. G., *J. Am. Chem. Soc.,* 1958;80:2838 record mp 260–265° C. dec.].

$^1$H NMR [(CD$_3$)$_2$SO] δ 6.66, 6.54 (2 br s, 2×2H, 2 NH$_2$), 5.60 (s, 1H, H-5).

$^{13}$C NMR δ 160.66, 157.46 (2 s, C-4,6), 143.73 (s, C-2), 117.00 (s, CN), 86.37 (d, C-5), 85.31 (s, C-3).

Trial 2

Anhydrous HBr (90 g, 1.11 mol) was condensed into a Parr reactor containing 1,2-dichloroethane (500 mL) at 0° C. Malononitrile (40.0 g, 0.605 mol) was added, the reactor sealed, and the resulting mixture was shaken at 100° C. for 16 hours. The solution was cooled (to 0° C.), and the solid was collected by filtration, then suspended in water (150 mL). The aqueous suspension was adjusted to pH 9 with concentrated aqueous ammonia hydroxide, stirred for 2 hours, then filtered. The collected solid was washed well with water, and dried to give 2-bromo-3-cyano-4,6-diaminopyridine (II) (42.4 g, 66%): mp (water) 215.5–218.5° C. [W. J. Middleton, U.S. Patent, *Chem. Abstracts,* 1957;2,790,806(51):P14829 records mp (EtOH) 255° C.; Carboni R. A., Coffman D. D., Howard E. G., *J. Am. Chem. Soc.,* 1958;80:2838 record mp 260–265° C. dec.]. The spectral data were the same as observed in Trial 1.

A solution of (II) (15.1 g, 0.071 mol), KOAc (7.0 g, 0.071 mol) and 5% Pd/C (4 g) in THF (tetrahydrofuran) (130 mL) and MeOH (methanol) (70 mL) was hydrogenated (55 psi/20° C.) for 7 days. The resulting solution was filtered over Celite, washing with THF/MeOH, then the solvents were removed under reduced pressure. The residue was dissolved in dilute HCl, then the solution neutralised with 40% NaOH and excess $Na_2CO_3$ to give 3-cyano-4,6-diaminopyridine (III) (6.58 g, 69%): mp (water) 197–198° C. [Metzger R., Oberdorfer J., Schwager C., Thielecke W., Boldt P., *Liebigs Ann. Chem.*, 1980;946–953 record mp (benzene) 205° C.].

$^1$H NMR [$(CD_3)_2SO$] δ 7.91 (s, 1H, H-2), 6.26, 6.24 (2 br s, 2×2H, 2NH$_2$), 5.63 (s, 1H, H-5).

$^{13}$C NMR δ 161.98, 155.48 (2 s, C-4,6), 153.86 (d, C-2), 118.10 (s, CN), 87.71 (d, C-5), 83.34 (s, C-3). Extraction of the remaining liquor with EtOAc (4×200 mL) gave additional (III) (2.12 g, 22%).

A solution of (III) (5.00 g, 37.3 mmol) and freshly prepared W-7 Raney nickel (120 mg wet catalyst, in absolute EtOH [ethanol]) in 99% formic acid (150 mL) and water (40 mL) was hydrogenated (60 psi/20° C.) for 2 days. Fresh catalyst was added (130 mg) and the reaction continued for 5 days, then further catalyst added (207 mg) and the reaction continued for 2 days. The resulting solution was filtered over Celite, washing with formic acid, then the solvents were removed under reduced pressure. The residue was diluted with water (150 mL), then excess $Na_2CO_3$ was added, and the solution extracted with EtOAc (ethyl acetate) (15×100 mL). Removal of the solvent gave a solid (3.65 g, 71%) which was used directly. Chromatography of a sample on neutral alumina, eluting with 1–3% MeOH/CHCl$_3$, gave 4,6-diamino-3-pyridylcarboxaldehyde (IV): mp (MeOH/CHCl$_3$/light petroleum) 343° C.

$^1$H NMR [$(CD_3)_2SO$] δ 9.48 (s, 1H, CHO), 8.04 (s, 1H, H-2), 7.12, 6.46 (2 br s, 2×2H, 2NH$_2$), 5.55 (s, 1H, H-5).

$^{13}$C NMR δ 190.27 (d, CHO), 162.34 (s, C-4 or 6), 159.77 (d, C-2), 155.14 (s, C-4 or 6), 110.45 (s, C-3), 86.98 (d, C-5).

Analysis calculated for $C_6H_7N_3O$·HCl requires:
C, 41.5; H, 4.7; N, 24.2%.
Found: C, 41.5; H, 4.6; N, 24.1%.

To a solution of sodium (31.5 mg, 1.37 mmol) dissolved in 2-ethoxyethanol (1.3 mL) was added 2,6-dichlorophenylacetonitrile (0.70 g, 3.76 mmol) and (IV) (467 mg, 3.41 mmol), and the mixture was then stirred at reflux for 2 hours. The solvent was removed under reduced pressure, then the residue was diluted with aqueous NaHCO$_3$ (50 mL) and extracted with EtOAc (5×50 mL). The solvent was removed, then chromatography of the residue on silica gel, eluting with 0–0.5% MeOH/CHCl$_3$, gave firstly 7-amino-2-[(2,6-dichlorophenyl)methyl]pyrido-[4,3-d]pyrimidine (V) (61 mg, 6%): mp (MeOH/CHCl$_3$/light petroleum) 205–206° C.

$^1$H NMR [$(CD_3)_2SO$] δ 9.12, 8.93 (2 s, 2H, H-4,5), 7.50 (d, J=8.1 Hz, 2H H-3',5'), 7.35 (dd, J=8.5, 7.7 Hz, 1H, H-4'), 6.91 (br s, 2H, NH$_2$), 6.36 (s, 1H, H-8), 4.55 (s, 2H, CH$_2$).

$^{13}$C NMR δ 166.88 (s, C-2), 162.45 (s, C-7), 160.45 (d, C-4), 154.27 (d, C-5), 153.96 (s, C-8a), 135.64 (s, 2C, C-2',6'), 134.12 (s, C-1'), 129.23 (d, C-4'), 128.22 (d, 2 C, C-3',5'), 112.88 (s, C-4a), 95.01 (d, C-8), 40.86 (t, CH$_2$).

Analysis calculated for $C_{14}H_{10}Cl_2N_4$ requires:
C, 55.1; H, 3.3; N, 18.4%.
Found: C, 55.2; H, 3.0; N, 18.6%.

Further elution with 0.5–3% MeOH/CHCl$_3$ gave 2,7-diamino-3-(2,6-dichlorophenyl)-[1,6]naphthyridine (VI) (708 mg, 68%): mp (CH$_2$Cl$_2$/light petroleum) 218–219° C.

$^1$H NMR [$(CD_3)_2SO$] δ 8.40 (s, 1H, H-5), 7.59 (d, J=7.8 Hz, 2H, H-3'5'), 7.59 (s, 1H, H-4), 7.46 (dd, J=8.7, 7.4 Hz, 1H, H-4'), 6.29 (s, 1H, H-8), 6.26, 5.94 (2 br s, 2×2H, 2NH$_2$).

$^{13}$C NMR δ 159.84, 157.68 (2 s, C-2,7), 153.27 (s, C-8a), 150.40 (d, C-5), 136.91 (d, C-4), 135.26 (s, 2 C, C-2',6'), 134.52 (s, C-1'), 130.61 (d, C-4'), 128.48 (d, 2 C, C-3',5'), 116.30, 112.72 (2 s, C-3,4a), 95.43 (d, C-8).

Analysis calculated for $C_{14}H_{10}Cl_2N_4$ requires:
C, 55.1; H, 3.3; N, 18.4%.
Found: C, 55.3; H, 3.5; N, 18.0%.

Alternative Conditions. To a solution of sodium (169 mg, 7.35 mmol) dissolved in 2-ethoxyethanol (7.0 mL) was added 2,6-dichlorophenylacetonitrile (1.40 g, 7.53 mmol) and (IV) (502 mg, 3.66 mmol), and the mixture was then stirred at reflux for 30 minutes. The resulting solution was diluted with aqueous NaHCO$_3$ (50 mL) and extracted with EtOAc (3×50 mL). The solvents were removed under reduced pressure, then chromatography of the residue on silica gel, eluting with 2–3% MeOH/CH$_2$Cl$_2$, gave firstly a mixed fraction, which on crystallisation from CHCl$_3$/light petroleum gave 2,6-dichlorophenylacetamide (165 mg): mp (MeOH/CH$_2$Cl$_2$) 211.5–213° C.

$^1$H NMR [$(CD_3)_2SO$] δ 7.53 (br s, 1H, NH), 7.44 (d, J=8.1 Hz, 2H, H-3,5), 7.30 (dd, J=8.5, 7.6 Hz, 1H, H-4), 7.02 (br s, 1H, NH), 3.77 (s, 2H, CH$_2$).

$^{13}$C NMR δ 169.60 (s, CONH$_2$), 135.56 (s, 2 C, C-2,6), 132.67 (s, C-1), 129.22 (d, C-4), 128.09 (d, 2 C, C-3,5), 37.31 (t, CH$_2$).

Analysis calculated for $C_8H_7Cl_2NO$ requires:
C, 47.1; H, 3.4; N, 6.9%
Found: C, 47.3; H, 3.5; N, 7.1%.

Further crystallisation of the liquors gave (V) (42 mg, 4%). Further elution of the column with 4–4.5% MeOH/CH$_2$Cl$_2$ gave (VI) (920 mg, 82%).

A suspension of (VI) (1.55 g, 5.08 mmol) in 50% HBF$_4$ (75 mL) at −5° C. was treated with solid NaNO$_2$ (3.0 g, 43.5 mmol, added in small portions over 5 hours), then kept at −20° C. for 5 days. The resulting mixture was neutralised with solid Na$_2$CO$_3$/ice, keeping the temperature below −10° C., and extracted with EtOAc (4×150 mL). The solvent was removed, then chromatography of the residue on silica gel, eluting with 1–2% MeOH/CH$_2$Cl$_2$, gave 3-(2,6-dichlorophenyl)-7-fluoro-1H-[1,6]naphthyridin-2-one; (VII) (0.91 g, 58%): mp (CH$_2$Cl$_2$/light petroleum) 254.5–255.5° C.

$^1$H NMR [$(CD_3)_2SO$] δ 12.54 (br s, 1H, NH), 8.66 (s, 1H, H-5), 8.13 (s, 1H, H-4), 7.61 (d, J=8.2 Hz, 2H, H-3',5'), 7.49 (dd, J=8.8, 7.4 Hz, 1H, H-4'), 6.89 (s, 1H, H-8).

$^{13}$C NMR δ 163.55 (d, $J_{C-F}$=234 Hz, C-7), 159.77 (s, C-2), 148.95 (dd, $J_{C-F}$=19 Hz, C-5), 147.69 (d, $J_{C-F}$=12 Hz, C-8a), 138.13 (d, C-4), 134.51 (s, 2 C C-2',6'), 133.51 (s, C-1'), 130.85 (d, C4'), 129.61 (d, $J_{C-F}$=2.5 Hz, C-3), 128.08 (d, 2 C, C-3',5'), 114.34 (d, $J_{C-F}$=2.5 Hz, C-4a), 92.95 (dd, $J_{C-F}$=42 Hz, C-8).

Analysis calculated for $C_{14}H_7Cl_2FN_2O$ requires:
C, 54.4; H, 2.3; N, 9.1; F, 6.2%.
Found: C, 54.0; H, 2.0; N, 9.2; F, 6.1%.

Further elution with 10–12% MeOH/CH$_2$Cl$_2$ gave 3-(2, 6-dichlorophenyl)-1H,6H-[1,6]naphthyridine-2,7-dione; (VIII) (0.45 g, 29%): mp (MeOH/CHCl$_3$) 363–369° C. dec.

$^1$H NMR [$(CD_3)_2SO$] δ 12.07, 11.55 (2 br s, 2H, 2NH), 8.10 (s, 1H, H-5), 7.67 (s, 1H, H-4), 7.56 (d, J=8.1 Hz, 2H, H-3',5'), 7.44 (dd, J=8.8,7.5 Hz, 1H, H-4'), 5.90 (s, 1H, H-8).

$^{13}$C NMR δ 161.84, 160.38 (2 s, C-2,7), 147.87 (s, C-8a), 139.65 (br d, C-5), 138.60 (d, C-4), 134.90 (s, 2 C, C-2',6'), 133.90 (s, C-1'), 130.50 (d, C4'), 127.97 (d, 2 C, C-3',5'), 124.18 (s, C-3), 105.09 (s, C-4a), 95.50 (d, C-8).

Analysis calculated for $C_{14}H_8Cl_2N_2O_2$ requires:
C, 54.7; H, 2.6; N, 9.1%.
Found: C, 54.6; H, 2.5; N, 9.0%.

To a stirred solution of (VII) (2.00 g, 6.47 mmol) in dry DMF (50 mL) at 0° C. was added 60% NaH (0.31 g, 7.75 mmol), followed by MeI (0.48 mL, 8.03 mmol) and the mixture stirred at 0° C. for 2 hours. The solvent was removed under reduced pressure, then the residue was diluted with aqueous NaHCO$_3$ (100 mL) and extracted with EtOAc (3×150 mL). The solvent was removed, then chromatography of the residue on silica gel, eluting with 33% light petroleum/CH$_2$Cl$_2$, gave firstly 3-(2,6-dichlorophenyl)-7-fluoro-2-methoxy-[1,6]naphthyridine (X, where R$^2$ is methyl) (39 mg, 2%): mp (CH$_2$Cl$_2$/light petroleum) 165–165.5° C.

$^1$H NMR [(CD$_3$)$_2$SO] δ 9.05 (s, 1H, H-5), 8.51 (s, 1H, H-4), 7.66 (d, J=8.2 Hz, 2H, H-3',5'), 7.53 (dd, J=8.6, 7.6 Hz, 1H, H-4'), 7.49 (s, 1H, H-8), 4.02 (s, 3H, OCH$_3$).

$^{13}$C NMR δ 163.68 (d, J$_{C-F}$=234 Hz, C-7), 162.59 (s, C-2), 152.93 (d, J$_{C-F}$=13 Hz, C-8a), 150.80 (dd, J$_{C-F}$=18 Hz, C-5), 139.53 (d, C-4), 134.33 (s, 2 C, C-2',6'), 133.02 (s, C-1), 131.11 (d, C-4'), 128.27 (d, 2 C, C-3',5'), 122.19 (d, J$_{C-F}$=2.4 Hz, C-3), 119.46 (d, J$_{C-F}$=3.0 Hz, C-4a), 102.52 (dd, J$_{C-F}$=37 Hz, C-8), 54.58 (q, OCH$_3$).

Analysis calculated for C$_{15}$H$_9$Cl$_2$FN$_2$O requires:

C, 55.8; H, 2.8; N, 8.7%.

Found: C, 55.8; H, 3.0; N, 8.5%.

Further elution with CH$_2$Cl$_2$ gave 3-(2,6-dichlorophenyl)-7-fluoro-1-methyl-1H-[1,6]naphthyridin-2-one; (IX; where R$^2$ is methyl) (1.88 g, 90%): mp (CH$_2$Cl$_2$/light petroleum) 201–203° C.

$^1$H NMR [(CD$_3$)$_2$SO] δ 8.70 (s, 1H, H-5), 8.16 (s, 1H, H-4), 7.61 (d, J=8.0 Hz, 2H, H-3',5'), 7.50 (dd, J=8.7, 7.3 Hz, 1H, H-4'), 7.38 (s, 1H, H-8), 3.66 NCH$_3$).

$^{13}$C NMR δ 164.21 (d, J$_{C-F}$=234 Hz, C-7), 159.23 (s, C-2), 149.16 (dd, J$_{C-F}$=19 Hz, C-5), 148.57 (d, J$_{C-F}$=12 Hz, C-8a), 137.48 (d, C-4), 134.47 (s, 2 C, C-2',6'), 133.85 (s, C-1), 130.88 (d, C-4'), 128.51 (d, J$_{C-F}$=2.7 Hz, C-3), 128.11 (d, 2 C, C-3',5'), 114.64 (d, J$_{C-F}$=3.0 Hz, C-4a), 93.91 (dd, J$_{C-F}$=43 Hz, C-8), 29.90 (q, NCH$_3$).

Analysis calculated for C$_{15}$H$_9$Cl$_2$FN$_2$O requires:

C, 55.8; H, 2.8; N, 8.7; F, 5.9%.

Found: C, 55.8; H, 2.5; N, 8.5; F, 5.9%.

A solution of (IX, where R$^2$ is methyl) (80 mg, 0.25 mmol) and 25% ammonium hydroxide (5.0 mL, 66 mmol) in 2-propanol (30 mL) was saturated with ammonia (gas) and stirred at 170° C. in a pressure vessel for 3 days. The solvent was removed, then the residue was diluted with aqueous Na$_2$CO$_3$ (50 mL) and extracted with CH$_2$Cl$_2$(3×50 mL). The solvent was removed, then chromatography of the residue on silica gel, eluting with 1–2% MeOH/CH$_2$Cl$_2$, gave 7-amino-3-(2,6-dichlorophenyl)-1-methyl-1H-[1,6] naphthyridin-2-one; (70 mg, 88%): mp 239–240° C.

$^1$H NMR [(CD$_3$)$_2$SO] δ 8.37 (s, 1H, H-5), 7.76 (s, 1H, H-4), 7.56 (d, J=8.2 Hz, 2H, H-3',5'), 7.43 (dd, J=8.7, 7.4 Hz, 1H, H-4'), 6.65 (br s, 2H, NH$_2$), 6.30 (s, 1H, H-8), 3.49 (s, 3H, NCH$_3$).

$^{13}$C NMR δ 161.24, 159.76 (2 s, C-2,7), 150.91 (d, C-5), 146.26 (s, C-8a), 138.32 (d, C-4), 135.07 (s, 2C, C-2',6'), 135.03 (s, C-1'), 130.23 (d, C-4'), 127.96 (d, 2 C, C-3',5'), 122.19 (s, C-3), 108.18 (s, C-4a), 88.28 (d, C-8), 28.76 (q, NCH$_3$).

Analysis calculated for C$_{15}$H$_{11}$Cl$_2$N$_3$O requires:

C, 56.3; H, 3.5; N, 13.1%.

Found: C, 56.1; H, 3.3; N, 13.1%.

Example B

Preparation of 3-(2,6-dichlorophenyl)-1-methyl-7-methylamino-1H-[1,6]naphthyridin-2-one A solution of (IX, where R$^2$ is methyl) (103 mg, 0.32 mmol) and 40% aqueous methylamine (5.0 mL, 58 mmol) in 2-propanol (30 mL) was stirred at 100° C. in a pressure vessel for 5 hours. The solvent was removed, then the residue was diluted with aqueous Na$_2$CO$_3$ (50 mL) and extracted with CH$_2$Cl$_2$ (3×50 mL). Removal of the solvent gave 3-(2,6-dichlorophenyl)-1-methyl-7-methylamino-1H-[1,6]naphthyridin-2-one; (103 mg, 97%): mp (CH$_2$Cl$_2$/light petroleum) 252–253.5° C.

$^1$H NMR [(CD$_3$)$_2$SO] δ 8.42 (s, 1H, H-5), 7.76 (s, 1H, H-4), 7.56 (d, J=8.0 Hz, 2H, H-3',5'), 7.43 (dd, J=8.7, 7.3 Hz, 1H, H-4'), 7.15 (br q, J=4.8 Hz, 1H, NHCH$_3$), 6.20 (s, 1H, H-8), 3.53 (s, 3H, NCH$_3$), 2.88 (d, J=4.9 Hz, 3H, NHCH$_3$).

$^{13}$C NMR δ 160.76, 159.77 (2 s, C-2,7),150.71 (d, C-5), 146.15 (s, C-8a), 138.32 (d, C-4), 135.05 (s, 2 C, C-2',6'), 135.04 (s, C-1'), 130.19 (d, C-4'), 127.93 (d, 2C, C-3',5'), 122.03 (s, C-3), 108.03 (s, C-4a), 86.98 (br d, C-8), 28.82, 28.23 (2NCH$_3$).

Analysis calculated for C$_{16}$H$_{13}$Cl$_2$N$_3$O requires:

C, 57.5; H, 3.9; N, 12.6%.

Found: C, 57.5; H, 4.0; N, 12.6%.

Example C

Preparation of 3-(2,6-dichlorophenyl)-7-dimethylamino-1-methyl-1H -[1,6]naphthyridin-2-one A solution of (IX, where R$^2$ is methyl) (102 mg, 0.32 mmol) and 40% aqueous dimethylamine (5.0 mL, 40 mmol) in 2-propanol (50 mL) was stirred at 90° C. in a pressure vessel for 30 minutes. The solvent was removed, then the residue was diluted with aqueous Na$_2$CO$_3$ (50 mL) and extracted with EtOAc (4×50 mL). Removal of the solvent gave 3-(2,6-dichlorophenyl)-7-dimethylamino-1-methyl-1H-[1,6]naphthyridin-2-one; (107 mg, 97%): mp (CH$_2$Cl$_2$/ light petroleum) 265–266° C.

$^1$H NMR (CDCl$_3$) δ 8.40 (s, 1H, H-5), 7.54 (s, 1H, H-4), 7.39 (d, J=8.2 Hz, 2H, H-3',5'), 7.24 (dd, J=8.6, 7.7 Hz, 1H, H-4'), 6.09 (s, 1H, H-8), 3.67 (s, 3H, NCH$_3$), 3.22 (s, 6H, N(CH$_3$)$_2$).

$^{13}$C NMR δ 160.90, 160.02 (2 s, C-2,7), 150.15 (d, C-5), 146.95 (s, C-8a), 138.29 (d, C-4), 135.88 (s, 2C, C-2',6'), 135.01 (s, C-1'), 129.48 (d, C-4'), 127.91 (d, 2 C, C-3',5'), 123.80 (s, C-3), 108.33 (s, C-4a), 86.64 (d, C-8), 38.40 (q, 2 C, N(CH$_3$)$_2$), 29.27 (q, NCH$_3$).

Analysis calculated for C$_{17}$H$_{15}$Cl$_2$N$_3$O requires:

C, 58.6; H, 4.3; N, 12.1%.

Found: C, 58.9; H, 4.2; N, 12.4%.

Example D

Preparation of 3-(2,6-dichlorophenyl)-7-[2-(diethylamino)ethylamino]-1-methyl-1H-[1,6] naphthyridin-2-one A solution of (IX, where R$^2$ is methyl) (101 mg, 0.31 mmol) and N,N-diethylethylenediamine (0.45 mL, 3.21 mmol) in 2-pentanol (10 mL) was stirred at 115° C. for 15 hours. The solvent was removed under reduced pressure, then the residue was diluted with aqueous Na$_2$CO$_3$ (50 mL) and extracted with EtOAc (3×50 mL). The solvent was removed, then chromatography of the residue on silica gel, eluting with 2% MeOH/CH$_2$Cl$_2$ containing 0.3% Et$_3$N, gave a crude product, which was treated with aqueous Na$_2$CO$_3$ and extracted with CH$_2$Cl$_2$ (4×50 mL). The solvent was removed, then chromatography of the residue on alumina, eluting with 0.25–0.3% MeOH/CH$_2$Cl$_2$, gave 3-(2,6-dichlorophenyl)-7-[2-(diethylamino)ethylamino]-1-methyl- 1H-[1,6]naphthyridin-2-one; (81 mg, 62%): mp (hexane/Et$_2$O) 100–102° C.

$^1$H NMR (CDCl$_3$) δ 8.34 (s, 1H, H-5), 7.52 (s, 1H, H-4), 7.39 (d, J=8.1 Hz, 2H, H-3',5'), 7.24 (dd, J=8.5, 7.7 Hz, 1H, H-4'), 6.07 (s, 1H, H-8), 5.67 (br s, 1H, NH), 3.65 (s, 3H, NCH$_3$), 3.38 (q, J=5.6 Hz, 2H, NHCH$_2$), 2.75 (t, J=6.0 Hz, 2H, NCH$_2$), 2.60 (q, J=7.1 Hz, 4H, N(CH$_2$)$_2$), 1.06 (t, J=7.1 Hz, 6H, 2CH$_3$).

$^{13}$C NMR δ 160.80, 159.93 (2 s, C-2,7), 150.77 (d, C-5), 147.16 (s, C-8a), 138.31 (d, C-4), 135.86 (s, 2C, C-2',6'), 134.91 (s, C-1'), 129.51 (d, C4'), 127.92 (d, 2 C, C-3',5'), 123.98 (s, C-3), 109.27 (s, C-4a), 87.23 (d, C-8), 51.16 (t, NCH$_2$), 46.53 (t, 2 C, N(CH$_2$)$_2$), 39.76 (t, NCH$_2$), 29.37 (q, NCH$_3$), 11.69 (q, 2 C, 2CH$_3$).

Analysis calculated for C$_{21}$H$_{24}$Cl$_2$N$_4$O requires:
C, 60.2; H, 5.8; N, 13.4%.
Found: C, 60.1; H, 5.6; N, 13.2%.

Example E

Preparation of 3-(2,6-dichlorophenyl)-7-[3-(diethylamino)propylamino]-1-methyl-1H-[1,6]naphthyridin-2-one A solution of (IX, where R$^2$ is methyl) (101 mg, 0.31 mmol) and 3-(diethylamino)propylamine (0.50 mL, 3.18mmol) in 2-pentanol (10 mL) was stirred at reflux for 17 hours. The solvent was removed under reduced pressure, then the residue was diluted with aqueous Na$_2$CO$_3$ (50 mL) and extracted with EtOAc (4×50 mL). The solvent was removed, then chromatography of the residue on silica gel, eluting with 2–4% MeOH/CH$_2$Cl$_2$ containing 0.3% Et$_3$N, gave a crude product, which was treated with aqueous Na$_2$CO$_3$ and extracted with CH$_2$Cl$_2$ (3×50mL) to give 3-(2,6-dichlorophenyl)-7-[3-(diethylamino)propylamino]-1-methyl-1H-[1,6]naphthyridin-2-one; (127 mg, 94%): mp (CH$_2$Cl$_2$/light petroleum) 118–120° C.

$^1$H NMR (CDCl$_3$) δ 8.33 (s, 1H, H-5), 7.51 (s, 1H, H-4), 7.39 (d, J=8.3 Hz 2H z, H-3',5'), 7.24 (dd, J=8.6, 7.7 Hz, 1H, H-4'), 6.36 (br s, 1H, NH), 6.01 (s, 1H, H-8), 3.64 (s, 3H, NCH$_3$), 3.43 (td, J=6.1, 5.3 Hz, 2H, NHCH$_2$), 2.60 (t, J=6.3 Hz, 2H, NCH$_2$), 2.57 (q, J=7.1 Hz, 4H, N(CH$_2$)$_2$),1.83 (pentet, J=6.3 Hz, 2H, CH$_2$), 1.07 (t, J=7.1 Hz, 6H, 2CH$_3$).

$^{13}$C NMR δ 160.82, 160.05 (2 s, C-2,7), 150.87 (d, C-5), 147.14 (s, C-8a), 138.36 (d, C-4), 135.88 (s, 2 C, C-2',6'), 134.96 (s, C-1'), 129.48 (d, C-4'), 127.91 (d, 2 C, C-3',5'), 123.72 (s, C-3), 109.11 (s, C-4a), 86.65 (d, C-8), 51.87 (t, NCH$_2$), 47.01 (t, 2 C, N(CH$_2$)$_2$), 42.34 (t, NCH$_2$), 29.32 (q, NCH$_3$), 25.95 (t, CH$_2$), 11.81 (q, 2 C, 2 CH$_3$).

Analysis calculated for C$_{22}$H$_{26}$Cl$_2$N$_4$O requires:
C, 61.0; H, 6.1; N, 12.9%.
Found: C, 61.0; H, 5.9; N, 12.8%.

Example F

Preparation of 3-(2,6-dichlorophenyl)-7-[4-(diethylamino)butylamino]-1-methyl-1H-[1,6]naphthyridin-2-one A solution of (IX, where R$^2$ is methyl) (104 mg, 0.32 mmol) and 4-(diethylamino)butylamine (0.51 g, 3.54 mmnol) in 2-pentanol (10 mL) was stirred at reflux for 1 day. The solvent was removed under reduced pressure, then the residue was diluted with aqueous Na$_2$ CO$_3$ (50 mL) and extracted with EtOAc (3×50 mL). The solvent was removed, then chromatography of the residue on silica gel, eluting with 2–5% MeOH/CH$_2$ Cl$_2$ containing 0.3% Et$_3$N, gave a crude product, which was treated with aqueous Na$_2$ CO$_3$ and extracted with CH$_2$ Cl$_2$ (4×50 mL). The solvent was removed, then chromatography of the residue on alumina, eluting with 0.5–1% MeOH/CH$_2$Cl$_2$, gave 3-(2,6-dichlorophenyl)-7-[4-(diethylamino)butylamino]-1-methyl-1H-[1,6]naphthyridin-2-one; (125 mg, 87%): mp (pentane) 123–124.5° C.

$^1$H NMR (CDCl$_3$) δ 8.32 (s, 1H, H-5), 7.52 (s, 1H, H-4), 7.39 (d, J=8.4 Hz, 2H, H-3',5'), 7.24 (dd, J=8.5, 7.6 Hz, 1H, H-4'), 6.03 (s, 1H, H-8), 5.59 (br s, 1H, NH), 3.64 (s, 3H, NCH$_3$), 3.35 (td, J=6.5, 4.6 Hz, 2H, NHCH$_2$), 2.56 (q, J=7.2 Hz, 4H, N(CH$_2$)$_2$), 2.49 (t, J=7.1 Hz, 2H, NCH$_2$), 1.74 (pentet, J=7.0 Hz, 2H, CH$_2$), 1.62 (pentet, J=7.0 Hz, 2H, CH$_2$), 1.05 (t, J=7.1 Hz, 6H, 2CH$_3$).

$^{13}$C NMR δ 160.81, 159.92 (2 s, C-2,7), 150.80 (d, C-5), 147.17 (s, C-8a), 138.32 (d, C-4), 135.86 (s, 2 C, C-2',6'), 134.92 (s, C-1'), 129.51 (d, C-4'), 127.91 (d, 2 C, C-3',5'), 123.89 (s, C-3), 109.21 (s, C-4a), 86.72 (d, C-8), 52.57 (t, NCH$_2$), 46.69 (t, 2 C, N(CH$_2$)$_2$), 42.47 (t, NCH$_2$), 29.34 (q, NCH$_3$), 27.37, 24.91 (2 t, 2CH$_2$), 11.47 (q, 2 C, 2CH$_3$).

Analysis calculated for C$_{23}$H$_{28}$Cl$_2$N$_4$O requires:
C, 61.8; H, 6.3; N, 12.5%.
Found: C, 61.6; H, 6.5; N, 12.4%.

Example G

Preparation of 3-(2,6-dichlorophenyl)-7-[5-(diethylamino)pentylamino]-1-methyl-1H-[1,6]naphthyridin-2-one A solution of (IX, where R$^2$ is methyl) (94 mg, 0.29 mmol) and 5-(diethylamino)pentylamine (0.52 g of ca 90%, 2.96 mmol) in 2-pentanol (10 mL) was stirred at reflux for 18 hours. The solvent was removed under reduced pressure, then the residue was diluted with aqueous Na$_2$CO$_3$ (50 mL) and extracted with EtOAc (4×50 mL). The solvent was removed, then chromatography of the residue on silica gel, eluting with 1–2% MeOH/CH$_2$Cl$_2$ containing 0.3% Et$_3$N, gave a crude product, which was treated with aqueous Na$_2$CO$_3$ and extracted with CH$_2$Cl$_2$ (4×50 mL). The solvent was removed, then chromatography of the residue on alumina, eluting with 1% EtOH/CHCl$_3$, gave 3-(2,6-dichlorophenyl)-7-[5-(diethylamino)pentylamino]-1-methyl-1H-[1,6]naphthyridin-2-one; (125 mg, 93%): foam.

$^1$H NMR (CDCl$_3$) δ 8.32 (s, 1H, H-5), 7.52 (s, 1H, H-4), 7.40 (d, J=8.0 Hz, 2H, H-3',5'), 7.24 (dd, J=8.6, 7.7 Hz, 1H, H-4'), 6.04 (s, 1H, H-8), 5.06 (br t, J=5.4 Hz, 1H, NHCH$_2$), 3.65 (s, 3H, NCH$_3$), 3.34 (td, J=6.9, 5.7 Hz, 2H, NHCH$_2$), 2.53 (q, J=7.2 Hz, 4H, N(CH$_2$)$_2$), 2.44 (t, J=7.4 Hz, 2H, NCH$_2$), 1.73 (pentet, J=7.2 Hz, 2H, CH$_2$), 1.54, 1.46 (2 pentet, J=7.5 Hz, 2×2H, 2CH$_2$), 1.03 (t, J=7.2 Hz, 6H, 2CH$_3$).

$^{13}$C NMR δ 160.78, 159.86 (2 s, C-2,7), 150.76 (d, C-5), 147.25 (s, C-8a), 138.28 (d, C-4), 135.85 (s, 2 C, C-2',6'), 134.87 (s, C-1'), 129.53 (d, C4'), 127.92 (d, 2 C, C-3',5'), 124.05 (s, C-3), 109.30 (s, C-4a), 86.61 (d, C-8), 52.73 (t, NCH$_2$), 46.86 (t, 2 C, N(CH$_2$)$_2$), 42.47 (t, NCH$_2$), 29.38 (q, NCH$_3$), 29.15, 26.85, 25.07 (3 t, 3CH$_2$), 11.59 (q, 2 C, 2CH$_3$).

Analysis calculated for C$_{24}$H$_{30}$Cl$_2$N$_4$O requires:
C, 62,5; H, 6.6; N, 12.1%.
Found: C, 62.2; H, 6,7; N, 11.8%.

Example H

Preparation of 3-(2,6-dichlorophenyl)-1-methyl-7-[3-(4-methylpiperazin-1-yl)propylamino]-1H-[1,6]naphthyridin-2-one A solution of (IX, where R$^2$ is methyl) (80 mg, 0.25 mmol) and 1-(3-aminopropyl)4-methylpiperazine (0.42 g, 2.66 mmol) in 2-pentanol (10 mL) was stirred at reflux for 16 hours. The solvent was removed under reduced pressure, then the residue was diluted with aqueous Na$_2$CO$_3$ (50 mL) and extracted with EtOAc (3×50 mL). The solvent was removed, then chromatography of the residue on silica gel, eluting with 3–6% MeOH/CH$_2$Cl$_2$ containing 0.3% Et$_3$N, gave a crude product, which was treated with aqueous Na$_2$CO$_3$ and extracted with EtOAc (3×50 mL) to give 3-(2,6-dichlorophenyl)-1-methyl-7-[3-(4-methylpiperazin-1-yl)propylamino]-1H-[1,6]naphthyridin-2-one; (99 mg, 87%):

mp (CH$_2$Cl$_2$/hexane) 164–166° C.

$^1$H NMR [(CD$_3$)$_2$SO] δ 8.40 (s, 1H, H-5), 7.74 (s, 1H, H-4), 7.56 (d, J=7.9 Hz, 2H, H-3',5'), 7.43 (dd, J=8.7, 7.5 Hz, 1H, H4'), 7.21 (br t, J=5.6 Hz, 1H, NHCH$_2$), 6.24 (s, 1H, H-8), 3.50 (s, 3H, NCH$_3$), 3.34 (q, J=6.4 Hz, 2H, NHCH$_2$), 2.6–2.1 (br s, 8H, N(CH$_2$)$_4$N), 2.36 (t, J=7.1 Hz, 2H, NCH$_2$), 2.14 (s, 3H, NCH$_3$), 1.71 (pentet, J=6.9 Hz, 2H, CH$_2$).

$^{13}$C NMR δ 160.15, 159.80 (2 s, C-2,7), 150.73 (d, C-5), 146.07 (s, C-8a), 138.32 (d, C-4), 135.07 (s, 3C, C-1',2',6'), 130.23 (d, C4'), 127.97 (d, 2 C, C-3',5'), 122.04 (s, C-3), 108.10 (s, C-4a), 87.73 (br d, C-8), 55.53 (t, NCH$_2$), 54.70, 52.66 (2 t, 2×2 C, N(CH$_2$)$_4$N), 45.67 (q, NCH$_3$), 39.43 (t, NCH$_2$), 28.81 (q, NCH$_3$), 26.07 (t, CH$_2$).

Analysis calculated for C$_{23}$H$_{27}$Cl$_2$N$_5$O requires:
C, 60.0; H, 5.9; N, 15.2%.
Found: C, 59.8; H, 6.2; N, 15.0%.

Example I

Preparation of 3-(2,6-dichlorophenyl)-1-methyl-7-[4-(4-methylpiperazin-1-yl)butylamino]-1H-[1,6]naphthyridin-2-one A solution of (IX, where R$^2$ is methyl) (101 mg, 0.31 mmol) and 1-(4-aminobutyl)-4-methylpiperazine (0.55 g, 3.22 mmol) in 2-pentanol (10 mL) was stirred at reflux for 16 hours. The solvent was removed under reduced pressure, then the residue was diluted with aqueous Na$_2$CO$_3$ (50 mL) and extracted with EtOAc (3×50 mL). The solvent was removed, then chromatography of the residue on silica gel, eluting with 24% MeOH/CH$_2$Cl$_2$ containing 0.3% Et$_3$N, gave a crude product, which was treated with aqueous Na$_2$CO$_3$ and extracted with CH$_2$Cl$_2$ (4×50 mL). The solvent was removed, then chromatography of the residue on alumina, eluting with 1% EtOH/CHCl$_3$, gave 3-(2,6-dichlorophenyl)-1-methyl-7-[4-(4-methylpiperazin-1-yl)butylamino]-1H-[1,6]naphthyridin-2-one; (140 mg, 94%): foam.

$^1$H NMR (CDCl$_3$) δ 8.32 (s, 1H, H-5), 7.52 (s, 1H, H-4), 7.39 (d, J=8.1 Hz, 2H, H-3',5'), 7.23 (dd, J=8.6, 7.7 Hz, 1H, H-4'), 6.03 (s, 1H, H-8), 5.54 (br s, 1H, NHCH$_2$), 3.64 (s, 3H, NCH$_3$), 3.36 (td, J=6.2, 4.4 Hz, 2H, NHCH$_2$), 2.8–2.2 (br s, 8H, N(CH$_2$)$_4$N), 2.42 (t, J=7.1 Hz, 2H, NCH$_2$), 2.30 (s, 3H, NCH$_3$), 1.75 (pentet, J=6.7 Hz, 2H, CH$_2$), 1.66 (pentet, J=6.9 Hz, 2H, CH$_2$).

$^{13}$C NMR δ 160.75, 159.85 (2 s, C-2,7), 150.74 (d, C-5), 147.13 (s, C-8a), 138.27 (d, C-4), 135.81 (s, 2 C, C-2',6'), 134.85 (s, C-1'), 129.49 (d, C-4'), 127.88 (d, 2 C, C-3',5'), 123.88 (s, C-3), 109.19 (s, C-4a), 86.67 (d, C-8), 57.90 (t, NCH$_2$), 55.02, 53.11 (2 t, 2×2 C, N(CH$_2$)$_4$N), 46.00 (q, NCH$_3$), 42.35 (t, NCH$_2$), 29.34 (q, NCH$_3$), 27.08, 24.47 (2 t, 2CH$_2$).

Analysis calculated for C$_{24}$H$_{29}$Cl$_2$N$_5$O.0.5 H$_2$O requires:
C, 59.6; H, 6.3; N, 14.5%.
Found: C, 59.6; H, 5.9; N, 14.5%.

Example J

Preparation of 3-(2,6-dichlorophenyl)-1-methyl-7-[5-(4-methylpiperazin-1-yl)pentylamino]-1H-[1,6]naphthyridin-2-one A solution of (IX, where R$^2$ is methyl) (102 mg, 0.32 mmol) and 1-(5-aminopentyl)-4-methylpiperazine (0.56 g, 3.03 mmol) in 2-pentanol (10 mL) was stirred at reflux for 1 day. The solvent was removed under reduced pressure, then the residue was diluted with aqueous Na$_2$CO$_3$ (50 mL) and extracted with EtOAc (4×50 mL). The solvent was removed, then chromatography of the residue on silica gel, eluting with 2–4% MeOH/CH$_2$Cl$_2$ containing 0.3% Et$_3$N, gave a crude product, which was treated with aqueous Na$_2$CO$_3$ and extracted with CH$_2$Cl$_2$ (4×50 mL). The solvent was removed, then chromatography of the residue on alumina, eluting with 0.25–0.5% MeOH/CH$_2$Cl$_2$, gave 3-(2,6-dichlorophenyl)-1-methyl-7-[5-(4-methylpiperazin-1-yl)pentylamino]-1H-[1,6]naphthyridin-2-one; (109 mg, 71%): foam.

$^1$H NMR (CDCl$_3$) δ 8.32 (s, 1H, H-5), 7.52 (s, 1H, H-4), 7.40 (d, J=8.0 Hz, 2H, H-3',5'), 7.24 (dd, J=8.6, 7.8 Hz, 1H, H-4'), 6.03 (s, 1H, H-8), 5.01 (br t, J=5.4 Hz, 1H, NHCH$_2$), 3.65 (s, 3H, NCH$_3$), 3.34 (td, J=6.9, 5.8 Hz, 2H, NHCH$_2$), 2.8–2.1 (br s, 8H, N(CH$_2$)$_4$N), 2.37 (t, J=7.6 Hz, 2H, NCH$_2$), 2.29 (s, 3H, NCH$_3$), 1.73 (pentet, J=7.3 Hz, 2H, CH$_2$), 1.58 (pentet, J=7.5 Hz, 2H, CH$_2$), 1.47 (pentet, J=7.4 Hz, 2H, CH$_2$).

$^{13}$C NMR δ 160.78, 159.84 (2 s, C-2,7), 150.77 (d, C-5), 147.26 (s, C-8a), 138.27 (d, C-4), 135.85 (s, 2 C, C-2',6'), 134.86 (s, C-1'), 129.55 (d, C-4'), 127.93 (d, 2 C, C-3',5'), 124.10 (s, C-3), 109.33 (s, C-4a), 86.62 (d, C-8), 58.45 (t, NCH$_2$), 55.11, 53.26 (2 t, 2×2 C, N(CH$_2$)$_4$N), 46.04 (q, NCH$_3$), 42.43 (t, NCH$_2$), 29.40 (q, NCH$_3$), 29.11, 26.60, 24.98 (3 t, 3CH$_2$).

Analysis calculated for C$_{25}$H$_{31}$Cl$_2$N$_5$O.0.75 H$_2$O requires:
C, 59.8; H, 6.5; N, 14.0%.
Found: C, 59.7; H, 6.5; N, 13.8%.

Example K

Preparation of 3-(2,6-dichlorophenyl)-1-methyl-7-[3-(4-morpholino)propylamino]-1H-[1,6]naphthyridin-2-one A solution of (IX, where R$^2$ is methyl) (103 mg, 0.32 mmol) and 4-(3-aminopropyl)morpholine (0.47 mL, 3.22 mmol) in 2-pentanol (10 mL) was stirred at reflux for 16 hours. The solvent was removed under reduced pressure, then the residue was diluted with aqueous Na$_2$CO$_3$ (50 mL) and extracted with EtOAc (3×50 mL). The solvent was removed, then chromatography of the residue on silica gel, eluting with 3–5% MeOH/CH$_2$Cl$_2$, gave a crude product, which was treated with aqueous Na$_2$CO$_3$ and extracted with CH$_2$Cl$_2$ (3×50 mL) to give 3-(2,6-dichlorophenyl)-1-methyl-7-[3-(4-morpholino)propylamino]-1H-[1,6]naphthyridin-2-one; (133 mg, 93%): mp (CH$_2$Cl$_2$/light petroleum) 157–159° C.

$^1$H NMR (CDCl$_3$) δ 8.33 (s, 1H, H-5), 7.52 (s, 1H, H-4), 7.40 (d, J=7.9 Hz, 2H, H-3',5'), 7.24 (dd, J=8.6, 7.6 Hz, 1H, H-4'), 6.03 (s, 1H, H-8), 5.87 (br t, J=5.2 Hz, 1H, NHCH$_2$), 3.77 (t, J=4.7 Hz, 4H, O(CH$_2$)$_2$), 3.65 (s, 3H, NCH$_3$), 3.45 (q, J=6.1 Hz, 2H, NHCH$_2$), 2.54 (t, J=6.6 Hz, 2H, NCH$_2$), 2.50 (br m, 4H, N(CH$_2$)$_2$), 1.87 (pentet, J 6.5 Hz, 2H, CH$_2$).

$^{13}$C NMR δ 160.77, 159.95 (2 s, C-2,7), 150.82 (d, C-5), 147.18 (s, C-8a), 138.29 (d, C-4), 135.83 (s, 2 C, C-2',6'), 134.86 (s, C-1'), 129.53 (d, C-4'), 127.92 (d, 2 C, C-3',5'), 123.99 (s, C-3), 109.27 (s, C-4a), 86.73 (d, C-8), 67.02 (t, 2 C, O(CH$_2$)$_2$), 57.20 (t, NCH$_2$), 53.77 (t, 2 C, N(CH$_2$)$_2$), 41.61 (t, NCH$_2$), 29.36 (q, NCH$_3$), 25.29 (t, CH$_2$).

Analysis calculated for C$_{22}$H$_{24}$Cl$_2$N$_4$O$_2$ requires:
C, 59.1; H, 5.4; N, 12.5%.
Found: C, 59.1; H, 5.4; N, 12.5%.

Example L

Preparation of 3-(2,6-dichlorophenyl)-7-[3-(imidazol-1-yl)propylamino]-1-methyl-1H-[1,6]naphthyridin-2-one A solution of (IX, where R$^2$ is methyl) (107 mg, 0.33 mmol) and 1-(3-aminopropyl)imidazole (0.40 mL, 3.36 mmol) in 2-pentanol (10 mL) was stirred at reflux for 16 hours. The solvent was removed under reduced pressure, then the residue was diluted with aqueous Na$_2$CO$_3$ (50mL) and extracted with EtOAc (3×50 mL). The solvent was removed, then chromatography of the residue twice on silica gel, eluting with 3–6% MeOH(CH$_2$Cl$_2$, gave a crude product, which was treated with aqueous Na$_2$CO$_3$ and extracted with CH$_2$Cl$_2$ (3×50 mL) to give 3-(2,6-dichlorophenyl)-7-[3-(imidazol-1-yl)propylamino]-1-methyl-1H-[1,6]naphthyridin-2-one; (116 mg, 82%): mp (CH$_2$Cl$_2$/hexane/Et$_2$O) 175–178° C.

$^1$H NMR (CDCl$_3$) δ 8.34 (s, 1H, H-5), 7.54, 7.53 (2 s, 2H, H-4,2"), 7.39 (d, J=8.1 Hz, 2H, H-3',5'), 7.24 (dd, J=8.5, 7.6 Hz, 1H, H-4'), 7.11, 6.97 (2 s, 2H, H-4",5"), 6.03 (s, 1H, H-8), 5.09 (br t, J=5.8 Hz, 1H, NHCH$_2$), 4.11 (t, J=6.8 Hz, 2H, NCH$_2$), 3.61 (s, 3H, NCH$_3$), 3.41 (q, J=6.4 Hz, 2H, NHCH$_2$), 2.17 (pentet, J=6.7 Hz, 2H, CH$_2$).

$^{13}$C NMR δ 160.69, 159.52 (2 s, C-2,7), 150.61 (d, C-5), 147.10 (s, C-8a), 138.17 (d, C-4), 137.18 (d, C-2'), 135.77 (s, 2 C, C-2',6'), 134.72 (s, C-1), 129.83, 129.61 (2 d, C-4',4"), 127.93 (d, 2 C, C-3',5'), 124.65 (s, C-3), 118.76 (d, C-5"), 109.72 (s, C-4a), 87.76 (d, C-8), 44.32, 39.02 (2 t, 2NCH$_2$), 30.82 (t, CH$_2$), 29.39 (q, NCH$_3$).

Analysis calculated for C$_{21}$H$_{19}$Cl$_2$N$_5$O requires:
C, 58.9; H, 4.5; N, 16.4%.
Found: C, 58.5; H, 4.5; N, 16.0%.

Example M

Preparation of 3-(2,6-dichlorophenyl)-1-methyl-7-(phenylamino)-1H-[1,6]naphthyridin-2-one A mixture of (IX, where R$^2$ is methyl) (86 mg, 0.27 mmol) and aniline (1.0 mL, 11.0 mmol) was stirred at 175° C. for 100 minutes. The resulting mixture was diluted with aqueous Na$_2$CO$_3$ (50 mL) and extracted with CH$_2$Cl$_2$ (2×50 mL). The solvent was removed, then chromatography of the residue on silica gel, eluting with 1% MeOH/CH$_2$Cl$_2$, gave 3-(2,6-dichlorophenyl)-1-methyl-7-(phenylamino)-1H-[1,6]naphthyridin-2-one; (88 mg, 83%): mp (CH$_2$Cl$_2$/light petroleum) 237–239° C.

$^1$H NMR [(CD$_3$)$_2$SO] δ 9.52 (br s, 1H, NH), 8.59 (s, 1H, H-5), 7.89 (s, 1H, H-4), 7.68 (d, J=7.7 Hz, 2H, H-2",6"), 7.58 (d, J=8.2 Hz, 2H, H-3',5'), 7.45 (dd, J=8.8, 7.5 Hz, 1H, H-4'), 7.32 (t, J=7.9 Hz, 2H, H-3",5"), 6.98 (t, J=7.3 Hz, 1H, H-4"), 6.73 (s, 1H, H-8), 3.56 (s, 3H, NCH$_3$).

$^{13}$C NMR δ 159.60, 156.99 (2 s, C-2,7), 150.07 (d, C-5), 145.91 (s, C-8a), 140.77 (s, C-1"), 138.01 (d, C-4), 134.88 (s, 2 C, C-2',6'), 134.71 (s, C-1'), 130.38 (d, C-4'), 128.70 (d, 2 C, C-3",5"), 127.97 (d, 2 C, C-3',5'), 124.08 (s, C-3), 121.44 (d, C-4"), 118.94 (d, 2 C, C-2",6"), 109.84 (s, C4a), 91.30 (d, C-8), 28.83 (q, NCH$_3$).

Analysis calculated for C$_{21}$H$_{15}$Cl$_2$N$_3$O.0.75 H$_2$O requires:
C, 61.5; H, 4.0; N, 10.3%.
Found: C, 61.4; H, 3.6; N, 10.2%.

Example N

Preparation of 3-(2,6-dichlorophenyl)-1-methyl-7-(4-pyridylamino)-1H-[1,6]naphthyridin-2-one A stirred solution of (IX, where R$^2$ is methyl) (100 mg, 0.31 mmol) and 4-aminopyridine (87 mg, 0.93 mmol) in THF (5.0 mL) under nitrogen at −78° C. was treated with a solution of LDA in cyclohexane (1.2 mL of 1.5 M, 1.8 mmol), then the temperature was allowed to rise slowly to 20° C., and the mixture stirred at 20° C. for 2 days. The resulting solution was treated with aqueous Na$_2$CO$_3$ and extracted with EtOAc (4×50 mL), then insoluble material was collected by filtration and combined with the above extracts. The solvent was removed, then chromatography of the residue on silica gel, eluting with 0.5–5% MeOH/EtOAc gave 3-(2,6-dichlorophenyl)-1-methyl-7-(4-pyridylamino)-1H-[1,6]naphthyridin-2-one; (58 mg, 47%): mp (MeOH/CHCl$_3$/light petroleum) 275–277° C.

$^1$H NMR [(CD$_3$)$_2$SO] δ 9.99 (br s, 1H, NH), 8.70 (s, 1H, H-5), 8.36 (d, J=5.8 Hz, 2H, H-3",5"), 7.98 (s, 1H, H-4), 7.71 (d, J=5.6 Hz, 2H, H-2",6"), 7.59 (d, J=8.1 Hz, 2H, H-3',5'), 7.47 (dd, J=8.8, 7.4 Hz, 1H, H-4'), 6.86 (s, 1H, H-8), 3.60 (s, 3H, NCH$_3$).

$^{13}$C NMR δ 159.55, 156.01 (2 s, C-2,7), 149.93 (d, 2 C, C-3",5"), 149.78 (d, C-5), 147.44 (s, C-1"), 145.96 (s, C-8a), 137.97 (d, C-4), 134.80 (s, 2 C, C-2',6'), 134.51 (s, C-1'), 130.58 (d, C-4'), 128.05 (d, 2 C, C-3',5'), 125.58 (s, C-3), 112.25 (d, 2 C, C-2",6"), 110.87 (s, C-4a), 93.79 (d, C-8), 29.03 (q, NCH$_3$).

Analysis calculated for C$_{20}$H$_{14}$Cl$_2$N$_4$O.0.5CH$_3$OH requires:
C, 59.6; H, 3.9; N, 13.6%.
Found: C, 59.8; H, 3.8; N, 13.8% (MeOH detected by NMR)

Example O

Preparation of 3-(2,6-dichlorophenyl)-7-[(4-methoxyphenyl)amino]-1-methyl-1H-[1,6]naphthyridin-2-one A mixture of (IX, where R$^2$ is methyl) (200 mg, 0.62 mmol) and p-anisidine (1.46 g, 11.9 mmol) was stirred at 175° C. for 4 hours. The resulting mixture was diluted with aqueous Na$_2$CO$_3$ (50 mL) and extracted with CH$_2$Cl$_2$ (3×50 mL). The solvent was removed, then successive chromatography of the residue on silica gel (3×), eluting with 0–1% MeOH/CH$_2$Cl$_2$, gave 3-(2,6-dichlorophenyl)-7-[(4-methoxyphenyl)amino]-1-methyl-1H-[1,6]naphthyridin-2-one; (99 mg, 38%): mp (CH$_2$Cl$_2$/light petroleum) 173–175° C.

$^1$H NMR (CDCl$_3$) δ 8.39 (s, 1H, H-5), 7.55 (s, 1H, H-4), 7.40 (d, J=8.1 Hz 2H, H-3',5'), 7.30 (d, J=8.9 Hz, 2H, H-2",6"), 7.24 (dd, J=8.6, 7.7 Hz, 1H, H-4'), 6.97 (d, J=8.8 Hz, 2H, H-3",5"), 6.95 (br s, 1H, NH), 6.40 (s, 1H, H-8), 3.85 (s, 3H, OCH$_3$), 3.54 (s, 3H, NCH$_3$).

$^{13}$C NMR δ 160.67, 158.79 (2 s, C-2,7), 157.24 (s, C-4"), 150.74 (d, C-5), 147.23 (s, C-8a), 138.00 (d, C-4), 135.77 (s, 2 C, C-2',6'), 134.71 (s, C-1'), 131.88 (s, C-1"), 129.63 (d, C-4'), 127.94 (d, 2 C, C-3',5'), 125.24 (d, 2 C, C-2",6"), 125.03 (s, C-3), 114.95 (d, 2 C, C-3",5"), 110.25 (s, C-4a), 87.97 (d, C-8), 55.53 (q, OCH$_3$), 29.41 (q, NCH$_3$).

Analysis calculated for $C_{22}H_{17}Cl_2N_3O_2$ requires:
C, 62.0; H, 4.0; N, 9.9%.
Found: C, 61.8; H, 3.9; N, 10.1%

Example P

Preparation of 3-(2,6-dichlorophenyl)-7-[(4-(2-(diethylamino)ethoxy)phenyl)amino]-1-methyl-1H-[1,6]naphthyridin-2-one A mixture of (IX, where $R^2$ is methyl) (100 mg, 0.31 mmol) and 4-[2-(diethylamino)ethoxy]aniline (1.18 g, 5.67 mmol) was stirred at 170° C. for 2.5 hours. The resulting mixture was diluted with aqueous $Na_2CO_3$ (50 mL) and extracted with $CH_2Cl_2$ (4×50 mL). The solvent was removed, then chromatography of the residue twice on alumina, eluting with 0.25% $MeOR/CH_2Cl_2$, gave a crude oil. This was further purified by preparative reversed-phase (C-18) HPLC (56% $CH_3CN$/aqueous $HCO_2NH_4$ buffer, pH 4.5), then by chromatography on alumina (due to partial oxidation during previous purification), eluting with 1% $MeOH/CH_2Cl_2$, to give 3-(2,6-dichlorophenyl)-7-[(4-(2-(diethylamino)ethoxy)phenyl)amino]-1-methyl-1H-[1,6] naphthyridin-2-one; (31 mg, 20%): mp (hexane/$Et_2O$) 149–150° C.

$^1$H NMR ($CDCl_3$) δ 8.40 (s, 1H, H-5), 7.55 (s, 1H, H-4), 7.40 (d, J=8.0 Hz, 2H, H-3',5'), 7.28 (d, J=8.9 Hz, 2H, H-2",6"), 7.25 (dd, J=8.5, 7.6 Hz, 1H, H-4'), 6.97 (d, J=8.9 Hz, 2H, H-3",5"), 6.67 (br s, 1H, NH), 6.39 (s, 1 H, H-8), 4.09 (t, J=6.2 Hz, 2H, $OCH_2$), 3.54 (s, 3H, $NCH_3$), 2.91 (t, J=6.2 Hz, 2H, $NCH_2$), 2.67 (q, J=7.1 Hz, 4H, $N(CH_2)_2$), 1.09 (t, J=7.1 Hz, 6H, $2CH_3$).

$^{13}$C NMR δ 160.67, 158.79 (2 s, C-2,7), 156.55 (s, C-4"), 150.72 (d, C-5), 147.24 (s, C-8a), 138.00 (d, C-4), 135.77 (s, 2 C, C-2',6'), 134.72 (s, C-1'), 131.84 (s, C-1"), 129.63 (d, C-4'), 127.95 (d, 2 C, C-3',5'), 125.25 (d, 2 C, C-2",6"), 125.05 (s, C-3), 115.58 (d, 2 C, C-3",5"), 110.26 (s, C-4a), 87.99 (d, C-8), 66.84 (t, $OCH_2$), 51.72 (t, $NCH_2$), 47.83 (t, 2 C, $N(CH_2)_2$), 29.41 (q, $NCH_3$), 11.74 (q, 2 C, $2CH_3$).

Analysis calculated for $C_{27}H_{28}Cl_2N_4O_2$ requires:
C, 63.4; H, 5.5; N, 11.0%.
Found: C, 63.5; H, 5.8; N, 11.1%.

Example Q

Preparation of 3-(2,6-dichlorophenyl)-1-methyl-7-[4-(4-morpholino)butylamino]-1H-[1,6]naphthyridin-2-one A solution of (IX, where $R^2$ is methyl) (100 mg, 0.31 mmol) and 4-(4-aminobutyl)morpholine (0.50 g, 3.16 mmol) in 2-pentanol (10 mL) was stirred at reflux for 15 hours. The solvent was removed under reduced pressure, then the residue was diluted with aqueous $Na_2CO_3$ (50 mL) and extracted with EtOAc (5×50 mL). The solvent was removed, then chromatography of the residue three times on silica gel, eluting with 2.5–4% $MeOH/CH_2Cl_2$, gave a crude product, which was treated with aqueous $Na_2CO_3$ and extracted with $CH_2Cl_2$ (4×50 mL) to give 3-(2,6-dichlorophenyl)-1-methyl-7-[3-(4-morpholino)butylamino]-1H-[1,6]naphthyridin-2-one; (135 mg, 95%): foam.

$^1$H NMR ($CDCl_3$) δ 8.32 (s, 1H, H-5), 7.52 (s, 1H, H-4), 7.39 (d, J=8.1 Hz, 2H, H-3',5'), 7.24 (dd, J=8.6, 7.7 Hz, 1H, H-4'), 6.02 (s, 1H, H-8), 5.48 (br s, 1H, $NHCH_2$), 3.75 (t, J=4.6 Hz, 4H, $O(CH_2)_2$), 3.65 (s, 3H, $NCH_3$), 3.36 (br t, J=6.6 Hz, 2H, $NHCH_2$), 2.47 (br m, 4H, $N(CH_2)_2$), 2.41 (t, J=7.1 Hz, 2H, $NCH_2$), 1.76, 1.66 (2 pentet, J=7.0 Hz, 2×2H, $2CH_2$).

$^{13}$C NMR δ 160.76, 159.85 (2 s, C-2,7), 150.76 (d, C-5), 147.18 (s, C-8a), 138.27 (d, C-4), 135.81 (s, 2 C, C-2',6'), 134.84 (s, C-1'), 129.52 (d, C-4'), 127.89 (d, 2 C, C-3',5'), 123.97 (s, C-3), 109.23 (s, C-4a), 86.61 (d, C-8), 66.88 (t, 2 C, $O(CH_2)_2$), 58.37 (t, $NCH_2$), 53.66 (t, 2 C, $N(CH_2)_2$), 42.36 (t, $NCH_2$), 29.34 (q, $NCH_3$), 27.02, 24.11 (2 t, $2CH_2$).

Analysis calculated for $C_{23}H_{26}Cl_2N_4O_2 \cdot H_2O$ requires:
C, 57.6; H, 5.9; N, 11.7%.
Found: C, 57.3; H, 5.6; N, 11.5%.

Example R

Preparation of 3-(2,6-dichlorophenyl)-7-[(4-(3-(diethylamino)propoxy)phenyl)amino]-1-methyl-1H-[1,6]naphthyridin-2-one A stirred solution of (IX, where $R^2$ is methyl) (82 mg, 0.25 mmol) and 4-[3-(diethylamino)propoxy]aniline (0.17 g, 0.77 mmol) in THF (5.0 mL) under nitrogen at −78° C. was treated with a solution of LDA in cyclohexane (1.0 mL of 1.5 M, 1.5 mmol), then the temperature was allowed to rise slowly to 20° C., and the mixture stirred at 20° C. for 43 hours. The resulting solution was treated with aqueous $Na_2CO_3$ and extracted with EtOAc (4×50 mL). The solvent was removed, then chromatography of the residue on alumina, eluting with 0.25–0.5% $MeOH/CH_2Cl_2$, gave 3-(2, 6-dichlorophenyl)-7-[(4-(3-(diethylamino)propoxy)phenyl) amino]-1-methyl-1H-[1,6]naphthyridin-2-one; (67 mg, 50%): mp ($CH_2Cl_2$/hexane) 151–152° C.

$^1$H NMR ($CDCl_3$) δ 8.39 (s, 1H, H-5), 7.55 (s, 1H, H-4), 7.40 (d, J=8.3 Hz, 2H, H-3',5'), 7.27 (d, J=9.0 Hz, 2H, H-2",6"), 7.25 (dd, J=8.7, 7.7 Hz, 1H, H-4'), 6.97 (d, J=9.0 Hz, 2H, H-3",5"), 6.86 (br s, 1H, NH), 6.39 (s, 1H, H-8), 4.05 (t, J=6.4 Hz, 2H, $OCH_2$), 3.54 (s, 3H, $NCH_3$), 2.63 (t, J=7.3 Hz, 2H, $NCH_2$), 2.56 (q, J=7.2 Hz, 4H, $N(CH_2)_2$), 1.95 (pentet, J=6.8 Hz, 2H, $CH_2$), 1.05 (t, J=7.1 Hz, 6H, $2CH_3$).

$^{13}$C NMR δ 160.68, 158.84 (2 s, C-2,7), 156.81 (s, C-4"), 150.76 (d, C-5), 147.24 (s, C-8a), 138.01 (d, C-4), 135.78 (s, 2 C, C-2',6'), 134.73 (s, C-1'), 131.67 (s, C-1"), 129.63 (d, C-4'), 127.95 (d, 2 C, C-3',5'), 125.29 (d, 2 C, C-2",6"), 125.01 (s, C-3), 115.56 (d, 2 C, C-3",5"), 110.24 (s, C-4a), 87.92 (d, C-8), 66.71 (t, $OCH_2$), 49.38 (t, $NCH_2$), 47.00 (t, 2 C, $N(CH_2)_2$), 29.41 (q, $NCH_3$), 27.05 (t, $CH_2$), 11.77 (q, 2 C, $2CH_3$).

Analysis calculated for $C_{28}H_{30}Cl_2N_4O_2$ requires:
C, 64.0; H, 5.8; N, 10.7%.
Found: C, 63.9; H, 5.6; N, 11.0%.

Example S

Preparation of 3-(2,6-dichlorophenyl)-1-methyl-7-[(4-(2-(4-methylpiperazin-1-yl)ethoxy)phenyl)amino]-1H-[1,6]naphthyridin-2-one A stirred solution of (IX, where $R^2$ is methyl) (100 mg, 0.31 mmol) and 4-[2-(4-methylpiperazin-1-yl)ethoxy]aniline (0.26 g, 1.12 mmol) in THF (5.0 mL) under nitrogen at −78° C. was treated with a solution of LDA in cyclohexane (0.8 mL of 1.5 M, 1.2 mmol), then the temperature was allowed to rise slowly to 20° C., and the mixture stirred at 20° C. for 2.5 days. The resulting solution was cooled to −78° C. and treated with AcOH (0.5 mL), then treated at 20° C. with aqueous $Na_2CO_3$ and extracted with EtOAc (5×50 mL). The solvent was removed, then chromatography of the residue on alumina, eluting with $CH_2Cl_2$, gave firstly recovered IX, where $R^2$ is methyl (49 mg, 49%). Further elution with 0.25–0.5% $MeOH/CH_2Cl_2$ gave a crude oil, which was again chromatographed on alumina, eluting with 0.25–0.3% MeOH/CH$_2$Cl$_2$, to give 3-(2,6-dichlorophenyl)-1-methyl-7-[(4-(2-(4-methylpiperazin-1-yl)ethoxy)phenyl)amino]-1H-[1,6]naphthyridin-2-one; (27 mg, 16%): mp (CH$_2$Cl$_2$/hexane) 170–171.5° C.

$^1$H NMR (CDCl$_3$) δ 8.40 (s, 1H, H-5), 7.55 (s, 1H, H-4), 7.40 (d, J=8.4 Hz, 2H, H-3',5'), 7.28 (d, J=8.9 Hz, 2H, H-2",6"), 7.25 (dd, J=8.7, 7.7 Hz, 1H, H-4'), 6.97 (d, J=8.9 Hz, 2H, H-3",5"), 6.83 (br s, 1H, NH), 6.40 (s, 1H, H-8), 4.14 (t, J=5.8 Hz, 2H, OCH$_2$), 3.54 (s, 3H, NCH$_3$), 2.86 (t, J=5.8 Hz, 2H, NCH$_2$), 2.66, 2.50 (2 br s, 2×4H, N(CH$_2$)$_4$N), 2.31 (s, 3H, NCH$_3$).

$^{13}$C NMR δ 160.66, 158.71 (2 s, C-2,7), 156.43 (s, C-4"), 150.74 (d, C-5), 147.23 (s, C-8a), 137.99 (d, C-4), 135.77 (s, 2 C, C-2',6'), 134.71 (s, C-1'), 131.97 (s, C-1"), 129.64 (d, C-4'), 127.95 (d, 2 C, C-3',5'), 125.17 (d, 2 C, C-2",6"), 125.08 (s, C-3), 115.66 (d, 2 C, C-3",5"), 110.29 (s, C-4a), 88.02 (d, C-8), 66.25 (t, OCH$_2$), 57.15 (t, NCH$_2$), 55.02, 53.56 (2 t, 2×2 C, N(CH$_2$)$_4$N), 46.01 (q, NCH$_3$), 29.43 (q, NCH$_3$).

Analysis calculated for C$_{28}$H$_{29}$Cl$_2$N$_5$O$_2$ requires:
C, 62.5; H, 5.4; N, 13.0%.
Found: C, 62.5; H, 5.7; N, 13.1%.

Example T

Preparation of 3-(2,6-dichlorophenyl)-1-methyl-7-[(4-(3-(4-methylpiperazin-1-yl)propoxy)phenyl)amino]-1H-[1,6]naphthyridin-2-one A stirred solution of (IX, where R$^2$ is methyl) (103 mg, 0.32 mmol) and 4-[3-(4-methylpiperazin-1-yl)propoxy]aniline (0.31 g, 1.24 mmol) in THF (5.0 mL) under nitrogen at −78° C. was treated with a solution of LDA in cyclohexane (0.9 mL of 1.5 M, 1.35 mmol), then the temperature was allowed to rise slowly to 20° C., and the mixture stirred at 20° C. for 2.5 days. The resulting solution was treated with aqueous Na$_2$CO$_3$ and extracted with EtOAc (5×50 mL). The solvent was removed, then chromatography of the residue on alumina, eluting with 0.3–0.5% MeOH/CH$_2$Cl$_2$, gave 3-(2,6-dichlorophenyl)-1-methyl-7-[(4-(3-(4-methylpiperazin-1-yl)propoxy)phenyl)amino]-1H-[1,6]naphthyridin-2-one; (111 mg, 63%): mp (CH$_2$Cl$_2$/hexane) 159–160° C.

$^1$H NMR (CDCl$_3$) δ 8.39 (s, 1H, H-5), 7.55 (s, 1H, H-4), 7.40 (d, J=7.8 Hz, 2H, H-3',5'), 7.28 (d, J=8.8 Hz, 2H, H-2",6"), 7.25 (dd, J=8.7, 7.7 Hz, 1H, H-4'), 6.96 (d, J=8.8 Hz, 2H, H-3",5"), 6.90 (br s, 1H, NH), 6.40 (s, 1H, H-8), 4.05 (t, J=6.4 Hz, 2H, OCH$_2$), 3.54 (s, 3H, NCH$_3$), 2.8–2.2 (br s, 8H, N(CH$_2$)$_4$N), 2.56 (t, J=7.4 Hz, 2H, NCH$_2$), 2.30 (s, 3H, NCH$_3$), 2.00 (pentet, J=6.9 Hz, 2H, CH$_2$).

$^{13}$C NMR δ 160.66, 158.79 (2 s, C-2,7), 156.69 (s, C-4"), 150.74 (d, C-5), 147.23 (s, C-8a), 138.00 (d, C-4), 135.76 (s, 2 C, C-2',6'), 134.71 (s, C-1'), 131.76 (s, C-1"), 129.63 (d, C-4'), 127.94 (d, 2 C, C-3',5'), 125.23 (d, 2 C, C-2",6"), 125.01 (s, C-3), 115.55 (d, 2 C, C-3",5"), 110.24 (s, C-4a), 87.94 (d, C-8), 66.59 (t, OCH$_2$), 55.13 (t, 3C, NCH$_2$,N(CH$_2$)$_2$), 53.23 (t, 2 C, N(CH$_2$)$_2$, 46.04 (q, NCH$_3$), 29.41 (q, NCH$_3$), 26.79 (t, CH$_2$).

Analysis calculated for C$_{29}$H$_{31}$Cl$_2$N$_5$O$_2$ requires:
C, 63.0; H, 5.7; N, 12.7%.
Found: C, 62.9; H, 5.7; N, 13.0%.

Example U

Preparation of 3-(2,6-dichlorophenyl)-1-methyl-7-[(4-(4-methylpiperazin-1-yl)phenyl)amino]-1H-[1,6]naphthyridin-2-one A stirred solution of (IX, where R$^2$ is methyl) (100 mg, 0.31 mmol) and 4-(4-methylpiperazin-1-yl)aniline (177 mg, 0.93 mmol) in THF (5.0 mL) under nitrogen at −78° C. was treated with a solution of LDA in cyclohexane (1.2 mL of 1.5 M, 1.8 mmol), then the temperature was allowed to rise slowly to 20° C., and the mixture stirred at 20° C. for 40 hours. The resulting solution was treated with aqueous Na$_2$CO$_3$ and extracted with EtOAc (3×50 mL). The solvent was removed, then chromatography of the residue on alumina, eluting with 0.25–0.5% MeOH/CH$_2$Cl$_2$, then on silica gel, eluting with 2–3% MeOH/CH$_2$Cl$_2$, gave a crude product, which was treated with aqueous Na$_2$CO$_3$ and extracted with EtOAc (2×50 mL), to give 3-(2,6-dichlorophenyl)-1-methyl-7-[(4-(4-methylpiperazin-1-yl)phenyl)amino]-1H-[1,6]naphthyridin-2-one; (56 mg, 37%): mp (CH$_2$Cl$_2$/hexane) 153–161° C.

$^1$H NMR (CDCl$_3$) δ 8.40 (s, 1H, H-5), 7.55 (s, 1H, H-4), 7.40 (d, J=7.8 Hz, 2H, H-3',5'), 7.26 (d, J=9.0 Hz, 2H, H-2",6"), 7.25 (dd, J=8.6, 7.6 Hz, 1H, H-4'), 6.99 (d, J=9.0 Hz, 2H, H-3",5"), 6.68 (br s, 1H, NH), 6.43 (s, 1H, H-8), 3.54 (s, 3H, NCH$_3$), 3.25 (t, J=5.0 Hz, 4H, N(CH$_2$)$_2$), 2.62 (t, J=4.9 Hz, 4H, N(CH$_2$)$_2$), 2.38 (s, 3H, NCH$_3$).

$^{13}$C NMR δ 160.68, 158.69 (2 s, C-2,7), 150.75 (d, C-5), 148.86 (s, C-4"), 147.22 (s, C-8a), 138.01 (d, C-4), 135.78 (s, 2 C, C-2',6'), 134.74 (s, C-1'), 130.93 (s, C-1"), 129.61 (d, C-4'), 127.94 (d, 2 C, C-3',5'), 124.93 (s, C-3), 124.66 (d, 2 C, C-2",6"), 117.06 (d, 2 C, C-3",5"), 110.21 (s, C-4a), 87.95 (d, C-8), 55.03 (t, 2 C, N(CH$_2$)$_2$), 49.14 (t, 2 C, N(CH$_2$)$_2$), 46.05 (q, NCH$_3$), 29.44 NCH$_3$).

Analysis calculated for C$_{26}$H$_{25}$Cl$_2$N$_5$O.0.5 H$_2$O requires:
C, 62.0; H, 5.2; N, 13.9%.
Found: C, 61.8; H, 5.3; N, 13.5%

Example V

Preparation of 7-fluoro-1-ethyl-1H-[1,6]naphthyridin-2-one

A solution of (IV) (1.0 g, 7.3 mmol) in dioxane (10 mL) was treated with carbethoxymethylene triphenyl phosphorane (5.1 g, 14.7 mmol) and heated to a gentle reflux for 2.5 hours. The cooled reaction mixture was rapidly filtered through a pad of silica gel eluting with 0% to 5% methanol in ethyl acetate. Evaporation of the solvent and recrystallization (1:1 methylene chloride/ethyl acetate) of the resulting residue gave ethyl 3-(4,6-diamino-3-pyridyl) acrylate (XI) as a solid (0.72 g, 48%): mp 151–152° C.

$^1$H NMR [(CD$_3$)$_2$SO] δ 8.01 (s, 1H, H-2), 7.68 (d, 1H, J=15.9 Hz), 6.17 (d, 1H, J=15.9 Hz), 5.99, 5.87 (2 br s, 2×2H, 2NH$_2$), 5.62 (s, 1H, H-5), 4.13 (q, 2H, J=7.23 Hz, CH$_2$), 1.23 (t, 3H, J=7.23 Hz, CH$_3$).

Analysis calculated for C$_{10}$H$_{13}$N$_3$O$_2$ requires:
C, 57.96; H, 6.32; N, 20.28%.
Found: C, 57.90; H, 6.21; N, 20.34%.

A suspension of (XI) (4.7 g, 22.7 mmol) in 1,8-diazabicyclo[5.4.0]undec-7-ene (22 mL) was heated to 165° C. under nitrogen for 16 hours. The 1,8-diazabicyclo[5.4.0] undec-7-ene was distilled under vacuum to leave a residue that was triturated in hot hexanes (2×100 mL). The solid was then triturated in hot 5:1 ethyl acetate: methanol to provide an off-white solid that was filtered and washed with ethyl acetate. The filtrates were concentrated, purified by silica gel chromatography, and further processed as above to leave additional product. The crops were combined to give 7-amino-1H-[1,6]naphthyridin-2-one (XII) (2.55 g 70%): mp >275° C.

$^1$H NMR [(CD$_3$)2SO] δ 11.42 (bs, 1H, NHC=O), 8.24 (s, 1H, H-5), 7.68 (d, 1H, J=9.40 Hz), 6.37 (bs, 2H, NH$_2$), 6.13 (s, 1H, H-8), 6.06 (d, 1H, J=9.40 Hz).

MS (APCI) m/z 162 (M+H, 100%).

To a stirred solution of (XII) (2.1 g, 13 mmol) in dry DMF (65 mL) was added cesium carbonate (6.4 g, 19.6 mmol), followed by ethyl iodine (1.71 mL, 21.4 mmol), and the mixture was stirred at 60° C. for 4.5 hours. The cooled mixture was filtered, and the filtrate was diluted with ethyl acetate. The solution was washed with brine, dried, and concentrated to give an orange residue that was purified by silica gel chromatography, eluting with 1:1 ethyl acetate: hexanes and then ethyl acetate. Concentration of product fractions gave 7-amino-1-ethyl-1H-[1,6]naphthyridin-2-one (XIII) (1.3 g, 53%).

$^1$H NMR [(CD$_3$)$_2$SO] δ 8.23 (s, 1H, H-5), 7.64 (d, 1H, J=9.28 Hz), 6.40 (bs, 2H, NH$_2$), 6.26 (s, 1H, H-8), 6.11 (d, 1H, J=9.28 Hz), 3.98 (q, 2H, J=7.08 Hz, CH$_2$), 1.11 (t, 3H, J=7.08 Hz, CH$_3$).

A suspension of (XIII) (1.1 g, 5.8 mmol) in 48% aqueous HBF$_4$ (20 mL) at −10° C. was treated with NaNO$_2$ (0.44 g, 6.38 mmol, added in small portions over 3 hours). The resulting mixture was neutralized (pH 7) with solid Na$_2$CO$_3$ carefully, keeping the temperature below 0° C., and extracted with EtOAc (3×75 mL). The solvent was removed, then chromatography of the residue on silica gel, eluting with ethyl acetate, gave 7-fluoro-1-ethyl-1H-[1,6] naphthyridin-2-one (XV) (0.72 g, 64%).

$^1$H NMR [(CD$_3$)$_2$SO] δ 8.57 (s, 1H, H-5), 7.95 (d, 1H, J=9.52 Hz), 7.30 (s, 1H, H-8), 6.11 (d, 1H, J=9.52 Hz), 4.15 (q, 2H, J=7.08 Hz, CH$_2$.), 1.12 (t, 3H, J=7.08 Hz, CH$_3$).

MS (APCI) m/z 193 (M+H, 100%).

Example W

Preparation of 1-ethyl-7-phenylamino-1H-[1,6] naphthyridin-2-one

A stirred solution of (XV, where R$^2$ is ethyl) (100 mg, 0.52 mmol) and aniline (120 mg, 1.3 mmol) in THF (5.0 mL) under nitrogen at −78° C. was treated with a solution (1.2 mL, 1.8 mmol) of lithium diisopropylamide (1.5 M in cyclohexane), then the temperature was allowed to rise slowly to 20° C. overnight. The resulting solution was treated with 3 drops of glacial acetic acid and concentrated to a brown residue that was purified by silica gel chromatography eluting with EtOAc. The product fractions were pooled and concentrated to a solid that was crystallized to give 1-ethyl-7-phenylamino-1H -[1,6]naphthyridin-2-one (33 mg, 24%): mp (8:1 hexanes/dichloromethane) 174–175° C.

$^1$H NMR [(CD$_3$)$_2$SO] 67 9.37 (bs, 1H, NH), δ 8.52 (s, 1H, H-5), 7.81 (d, 1H, J=9.40 Hz), 7.66 (d, 2H, J=8.44 Hz,), 7.30 (t, 2H, J=7.47 Hz) 6.95 (t, 1H, J=7.47 Hz) 6.72 (s, 1H) 6.32 (d, 1H, J=9.40 Hz), 4.10 (q, 2H, J=7.23 Hz, CH$_2$), 1.23 (t, 3H, J=7.23 Hz, CH$_3$).

IR (KBR) 1624cm$^{-1}$.

MS (APCI) m/z 266.1.

Analysis calculated for C$_{16}$H$_{15}$N$_3$O.0.30 H$_2$O requires: C, 70.99; H, 5.81; N, 15.52%.

Found: C, 71.01; H, 5.62; N, 15.35%.

Example X

Preparation of 1-ethyl-7-(4-methoxyphenylamino)-1H-[1,6]naphthyridin-2-one

A stirred solution of (XV, where R$^2$ is ethyl) (100 mg, 0.52 mmol) and p-anisidine (160 mg, 1.3 mmol) in THF (5.0 mL) under nitrogen at −78° C. was treated with a solution (1.2 mL, 1.8 mmol) of lithium diisopropylamide (1.5 M in cyclohexane), then the temperature was allowed to rise slowly to 20° C. overnight. The resulting solution was treated with 3 drops of glacial acetic acid and concentrated to a brown residue that was purified by silica gel chromatography eluting with 1:1 EtOAc hexanes then EtOAc. The product fractions were pooled and concentrated to a solid that was crystallized to give 1-ethyl-7-(4-methoxyphenylamino)-1H -[1,6]naphthyridin-2-one (87 mg, 57%): mp (2-propanol) 165–166° C.

$^1$H NMR [(CD$_3$)$_2$SO] δ 9.17 (bs, 1H, NH), δ 8.46 (s, 1H, H-5), 7.77 (d, 1H, J=9.40 Hz), 7.52 (d, 2H, J=8.92 Hz,), 6.90 (d, 2H, J=8.92 Hz) 6.59 (s, 1H ) 6.28 (d, 1H, J=9.40 Hz), 4.07 (q, 2H, J=6.99 Hz, CH$_2$), 1.20 (t, 3H, J=6.99 Hz, CH$_3$).

IR(KBR) 1619 cm$^{-1}$.

MS (APCI) m/z 296.0.

Analysis calculated for C$_{17}$H$_{17}$N$_3$O$_2$ requires: C, 69.14; H, 5.80; N, 14.23%.

Found: C, 69.14; H, 5.84; N, 13.99%.

Example Y

Preparation of 1-ethyl-7-[4-(4-methylpiperazin-1-yl) phenylamino]-1H-[1,6]naphthyridin-2-one

A stirred solution of (XV, where R$^2$ is ethyl) (100 mg, 0.52 mmol), 4-(4-methyl-1-piperazinyl)aniline (0.26 g, 1.12 mmol) in THF (5.0 mL) under nitrogen at −78° C. was treated was treated with a solution (0.8 mL, 1.2 mmol) of lithium diisopropylamide (1.5 M in cyclohexane), then the temperature was allowed to rise slowly to 20° C. overnight. The resulting solution was treated with 3 drops of glacial acetic acid and concentrated to a dark residue that was purified by silica gel chromatography eluting with 90:9:1 EtOAc:MeOH:NH$_4$OH. The product fractions were pooled and concentrated to a solid that was triturated in boiling hexanes. The solid was collected and crystallized to give 1-ethyl-7-[4-(4-methylpiperazin-1-yl)phenylamino]-1H-[1, 6]naphthyridin-2-one (84 mg, 44%): mp (CH$_2$Cl$_2$/hexanes) 188–189° C.

$^1$H NMR [(CD$_3$)$_2$SO] δ 9.10 (bs, 1H, NH), δ 8.44 (s, 1H, H-5), 7.76 (d, 1H, J=9.40 Hz), 7.45 (d, 2H, J=8.92 Hz, ), 6.91 (d, 2H, J=9.16 Hz) 6.57 (s, 1H) 6.26 (d, 1H, J=9.40 Hz), 4.08 (q, 2H, J=6.99 Hz, CH$_2$), 3.05–3.08 (m, 4H, CH$_2$), 2.44–2.46 (m, 4H, CH$_2$), 2.22 (s, 3H, NCH$_3$), 1.20 (t, 3H, J=6.99 Hz, CH$_3$).

IR (KBR) 1619 cm$^{-1}$.

MS (APCI) m/z 364.2.

Analysis calculated for C$_{21}$H$_{25}$N$_5$O$_1$0.7 H$_2$O requires: C, 67.07; H, 7.08; N, 18.62%.

Found: C, 67.22; H, 6.70; N, 18.39%.

Example Z

Preparation of 1-ethyl-7-(4-(morpholin-4-yl) phenylamino)-1H-[1,6]naphthyridin-2-one

A stirred solution of (XV, where R$^2$ is ethyl) (100 mg, 0.52 mmol), 4-(4-morpholinyl)aniline (0.26 g, 1.1 mmol) in THF (5.0 mL) under nitrogen at −78° C. was treated with a solution (0.8 mL, 1.2 mmol) of lithium diisopropylamide (1.5 M in cyclohexane), then the temperature was allowed to rise slowly to 20° C. overnight. The resulting solution was treated with 3 drops of glacial acetic acid and concentrated to a dark residue that was purified that purified by silica gel chromatography eluting with EtOAc. The product fractions were pooled and concentrated to a solid that was crystallized to give 1-ethyl-7-(4-(morpholin-4-yl)phenylamino)-1H-[1, 6]naphthyridin-2-one (94 mg, 52%): mp (2-propanol/hexanes) 219–223° C.

$^1$H NMR [(CD$_3$)$_2$SO] δ 9.13 (bs, 1H, NH), δ 8.45 (s, 1H, H-5), 7.77 (d, 1H, J=9.40 Hz), 7.48 (d, 2H, J=8.92 Hz, ), 6.92 (d, 2H, J=8.92 Hz) 6.58 (s, 1H) 6.27 (d, 1H, J=9.40 Hz), 4.06 (q, 2H, J=6.99 Hz, CH$_2$), 3.68–3.78 (m, 4H, CH$_2$), 3.06–3.03 (m, 4H, CH$_2$), 1.20 (t, 3H, J=6.99 Hz, CH$_3$).

IR (KBR) 1619 cm$^{-1}$.

MS (APCI) m/z 351.2

Analysis calculated for C$_{20}$H$_{22}$N$_4$O$_2$.0.3 H$_2$O requires:

C, 67.44; H, 6.41; N, 15.73%.
Found: C, 67.45; H, 6.16; N, 15.35%.

Example AA

Preparation of 1-ethyl-7-(4-(piperidin-1-yl) phenylamino)-1H -[1,6]naphthyridin-2-one A stirred solution of (XV, where R$^2$ is ethyl) (100 mg, 0.52 mmol), 4-(1-piperidinyl)aniline (0.26 g, 1.12 mmol) in THF (5.0 mL) under nitrogen at −78° C. was treated with a solution (0.8 mL, 1.2 mmol) of lithium diisopropylamide (1.5 M in cyclohexane), then the temperature was allowed to rise slowly to 20° C. overnight. The resulting solution was treated with 3 drops of glacial acetic acid and concentrated to a dark residue that was purified that purified by silica gel chromatography eluting with EtOAc. The product fractions were pooled and concentrated to a foam that was crystallized to give ethyl-7-(4-(piperidin-1-yl)phenylamino)-1H -[1,6] naphthyridin-2-one (79 mg, 44%): mp (CH$_2$Cl$_2$/hexanes) 137–139° C.

$^1$H NMR [(CD$_3$)$_2$SO] δ 9.09 (bs, 1H, NH), δ 8.44 (s, 1H, H-5), 7.76 (d, 1H, J=9.40 Hz), 7.43 (d, 2H, J=8.92 Hz, ), 6.90 (d, 2H, J=9.16 Hz) 6.57 (s, 1H) 6.26 (d, 1H, J=9.16 Hz), 4.06 (q, 2H, J=6.99 Hz, CH$_2$), 3.03–3.06 (m, 4H, CH$_2$NCH$_2$), 1.66–1.60 (m, 4H, CH$_2$), 1.50–1.54 (m, 2H, CH$_2$), 1.20 (t, 3H, J=6.99 Hz, CH$_3$).

IR (KBR) 1620 cm$^{-1}$.

MS (APCI) m/z 349.2.

Analysis calculated for C$_{21}$H$_{24}$N$_4$O$_1$.0.2 H$_2$O requires:

C, 71.65; H, 6.99; N, 15.91%.
Found: C, 71.72; H, 6.81; N, 15.93%.

Example BB

Preparation of 1-ethyl-7-phenylamino-3,4-dihydro-1H -[1,6]naphthyridin-2-one

A suspension of 1-ethyl-7-phenylamino-1H-[1,6] naphthyridin-2-one from Example W (75 mg, 0.29 mmol), 0.6 g of Raney nickel, and 50 mL of ethanol was stirred under 50 psi of hydrogen at room temperature for 23 hours. The suspension was filtered and the filtrate was concentrated to a solid residue that was purified by preparative thin layer chromatography to give 1-ethyl-7-phenylamino-3,4-dihydro-1H-[1,6]naphthyridin-2-one (10 mg, 13% yield): mp 137–138° C.

$^1$H NMR [(CD$_3$)$_2$SO] δ 1.10 (t, 3H, J=7 Hz), 2.50 (t, 2H, J=7Hz), J=7 Hz), 3.76 (q, 2H, J=7 Hz), 6.47, (s, 1H ), 6.79 (t, 1H, J=7 Hz), 7.18 (t, 2H, J=8 Hz), 7.58 (d, 2H, J=8 Hz), 7.89 (s, 1H), 8.89 (s, 1H).

MS (APCI) m/z 268 (M+1)

Analysis calculated for C$_{16}$H$_{17}$N$_3$O.0.10 H$_2$O.0.15C$_4$H$_8$O$_2$ requires:

C, 70.62; H, 6.57; N, 14.88
Found: C, 70.90; H, 6.26; N, 14.56.

Purification of Tyrosine Kinases

Epidermal Growth Factor Receptor (EGFr). Human EGF receptor tyrosine kinase is isolated from A431 human epidermoid carcinoma cells by the following method. Cells were grown in roller bottles in 50% Dulbecco's Modified Eagle medium and 50% HAM F-12 nutrient media (Gibco) containing 10% fetal calf serum. Approximately 10$^9$ cells are lysed in two volumes of buffer containing 20 mM 2-(4N-[2-hydroxymethyl]piperazin-1-yl)ethanesulfonic acid (Hepes), pH 7.4, 5 mM ethylene glycol bis(2-aminoethyl ether) N,N,N',N'-tetraacetic acid (EGTA), 1% Triton X-100, 10% glycerol, 0.1 mM sodium orthovanadate, 5 mM sodium fluoride, 4 mM pyrophosphate, 4 mM benzamide, 1 mM dithiothreitol (DTT), 80 µg/mL aprotinin, 40 µg/mL leupeptin, and 1 mM phenylmethylsulfonyl fluoride (PMSF). After centrifugation at 25,000×g for 10 minutes, the supernatant is applied to a fast Q sepharose column (Pharmacia) and eluted with a linear gradient from 0.1 M NaCl to 0.4 M NaCl in 50 mM Hepes, 10% glycerol, pH 7.4. Enzyme active fractions are pooled, divided into aliquots, and stored at −100° C.

Platelet Derived Growth Factor Receptor (PDGFr) and Fibroblast Growth Factor Receptor (FGFr). Full length cDNAs for the mouse PDGF-β and human FGF-1 (flg) receptor tyrosine kinases were obtained from J. Escobedo and are prepared as described in *J. Biol. Chem.*, 1991;262:1482–1487. PCR primers are designed to amplify a fragment of DNA that codes for the intracellular tyrosine kinase domain. The fragment is melded into a baculovirus vector, cotransfected with AcMNPV DNA, and the recombinant virus isolated. SF9 insect cells are infected with the virus to overexpress the protein, and the cell lysate is used for the assay.

Other Kinases. c-Src kinase is purified from baculovirus infected insect cell lysates using an antipeptide monoclonal antibody directed against the N-terminal 2–17 amino acids as described previously by Fry, et al., *Anticancer Drug Design*, 1994;9:331–351. Protein kinase C (PKC.) is obtained as a rat brain preparation from Promega.

Kinase Assays

EGFr. Enzyme assays for IC$_{50}$ determinations are performed in 96-well filter plates (Millipore MADVN6550). The total volume is 0.1 mL containing 20 mM Hepes, pH 7.4, 50 µM sodium vanadate, 40 mM magnesium chloride, 10 µM ATP containing 0.5 µCi of [$^{32}$P]ATP, 20 µg of polyglutamic acid/tyrosine (Sigma Chemical Co., St. Louis, Mo.), 10 ng of EGF receptor tyrosine kinase and appropriate dilutions of inhibitor. All components except the ATP are added to the well, and the plate is incubated with shaking for 10 minutes at 25° C. The reaction is started by adding [$^{32}$P]ATP, and the plate is incubated at 25° C. for 10 minutes. The reaction is terminated by addition of 0.1 mL of 20% trichloroacetic acid (TCA). The plate is kept at 4° C. for at least 15 minutes to allow the substrate to precipitate. The wells are then washed five times with 0.2 mL of 10% TCA, and $^{32}$P incorporation is determined with a Wallac beta plate counter.

PDGFr and FGFr. The assay is performed in 96-well plates (100 µL/incubation/well), and conditions are optimized to measure the incorporation of $^{32}$P from [γ$^{32}$P]ATP into a glutamate-tyrosine copolymer substrate. Briefly, to each well is added 82.5 µL of incubation buffer containing 25 mM Hepes (pH 7.0), 150 mM NaCl, 0.1% Triton X-100, 0.2 mM PMSF, 0.2 mM sodium vanadate, 10 mM manganese chloride, and 750 μg/mL of poly (4:1) glutamate-tyrosine followed by 2.5 μL of inhibitor and 5 μL of enzyme lysate (7.5 μg/μL FGFR-TK or 6.0 μg/μL PDGFR-TK) to initiate the reaction. Following a 10 minute incubation at 25° C., 10 μL of [γ$^{32}$P]ATP (0.4 μCi plus 50 μM ATP) is added to each well, and samples are incubated for an additional 10 minutes at 25° C. The reaction is terminated by the addition of 100 μL of 30% trichloroacetic acid (TCA) containing 20 mM sodium pyrophosphate and precipitation of material onto glass fiber filter mats (Wallac). Filters are washed three times with 15% TCA containing 100 mM sodium pyrophosphate and the radioactivity retained on the filters counted in a Wallac 1250 Betaplate reader. Nonspecific activity is defined as radioactivity retained on the filters following incubation of samples with buffer alone; (no enzyme). Specific enzymatic activity is defined as total activity (enzyme plus buffer) minus nonspecific activity. The concentration of a compound that inhibited specific activity by 50% ($IC_{50}$) is determined based on the inhibition curve.

c-Src. The antibody, covalently linked to 0.65-μm latex beads, is added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 μg/mL each of leupeptin, pepstatin, and aprotinin. Insect cell lysate containing the c-Src protein is incubated with these beads for 3 to 4 hours at 4° C. with rotation. At the end of the lysate incubation, the beads are rinsed three times in lysis buffer, resuspended in lysis buffer containing 10% glycerol, and frozen. These latex beads are thawed, rinsed three times in assay buffer which is comprised of 40 mM tris pH 7.5, 5 mM magnesium chloride, and suspended in the same buffer. In a Millipore 96-well plate with a 0.65 μm polyvinylidine membrane bottom are added the reaction components: 10-μL c-Src beads, 10 μL of 2.5 mg/mL polyglutamate-tyrosine substrate, 5 μM ATP containing 0.2 μCi labeled $^{32}$P-ATP, 5 μL DMSO containing inhibitors or as a solvent control, and buffer to make the final volume 125 μL. The reaction is started at room temperature by addition of the ATP and quenched 10 minutes later by the addition of 125 μL of 30% TCA, 0.1 M sodium pyrophosphate for 15 minutes on ice. The plate is then filtered and the wells washed with two 250-μL aliquots of 15% TCA, 0.1 M pyrophosphate. The filters are punched, counted in a liquid scintillation counter, and the data examined for inhibitory activity in comparison to a known inhibitor such as erbstatin. The method is described more fully in *J. Med. Chem.*, 1994;37:598–609.

Cascade Assay for Inhibitors of the MAP Kinase Pathway (APK Assay)

Incorporation of $^{32}$P into myelin basic protein (MBP) is assayed in the presence of a glutathione; S-transferase fusion protein containing p44MAP kinase (GST-MAPK) and a glutathione; S-transferase fusion protein containing p45MEK (GST-MEK). The assay solution contains 20 mM HEPES, pH 7.4, 10 mM magnesium chloride, 1 mM manganese chloride, 1 mM EGTA, 50 μM [γ$^{32}$P]ATP, 10 μg GST-MEK, 0.5 μg GST-MAPK and 40 μg MBP in a final volume of 100 μL. Reactions are stopped after 20 minutes by addition of trichloroacetic acid and filtered through a GF/C filter mat. $^{32}$P retained on the filter mat is determined using a 1205 betaplate. Compounds are assessed at 10 μM for ability to inhibit incorporation of $^{32}$P.

To ascertain whether compounds are inhibiting GST-MEK or GST MAPK, two additional protocols are employed. In the first protocol, compounds are added to tubes containing GST-MEK, followed by addition of GST-MAPK, MBP and [γ$^{32}$P]ATP. In the second protocol, compounds are added to tubes containing both GST-MEK and GST-MAPK, followed by MBP and [γ$^{32}$P]ATP.

Compounds that show activity in both protocols are scored as MAPK inhibitors, while compounds showing activity in only the first protocol are scored as MEK inhibitors.

Other Kinases. An assay using the intracellular kinase domains of insulin receptor (INSr) is performed as described for the EGF receptor except that 10 mM manganese chloride is included in the reaction. The PKC assay is performed as previously described by Martiny-Baron, et al., *J. Biol. Chem.*, 1993;268:9194–9197.

TABLE 1

Inhibition of Protein Kinases

| Example | c-Src | FGFr | PDGFr | EGFr | INSr | APK | PKC |
|---|---|---|---|---|---|---|---|
| A | 0.35 | 0.28 | 2.5 | ~50 | ND | ND | 50 |
| B | 0.42 | 0.34 | 3.6 | ND | ND | ND | ND |
| C | >50 | >50 | >50 | ND | >50 | ND | ND |
| D | 13 | 3.7 | 16 | ND | ND | ND | ND |
| E | 0.30 | 0.22 | 4.0 | ND | ND | ND | ND |
| F | 0.04 | 0.07 | 0.42 | 3.8 | >50 | >10 | >50 |
| G | 0.02 | 0.07 | 0.69 | ND | ND | ND | ND |
| H | 0.06 | 0.05 | 0.89 | 3.2 | >50 | 10 | <50 |
| I | 0.04 | 0.10 | 0.95 | ND | ND | ND | ND |
| J | 0.03 | 0.09 | 0.85 | ND | ND | ND | ND |
| K | 0.36 | 0.31 | 4.7 | <50 | ND | ND | >50 |
| L | 0.54 | 0.35 | 1.7 | ND | ND | ND | ND |
| M | 0.79 | 1.3 | 1.0 | <50 | ND | ND | >50 |
| N | 0.55 | 3.3 | 9.6 | ND | ND | ND | ND |
| O | 1.7 | 1.2 | 1.7 | ND | ND | ND | ND |
| P | 0.08 | 0.06 | 0.09 | 0.59 | >50 | ND | >50 |
| Q | 0.05 | 0.32 | 3.1 | ND | ND | ND | ND |
| R | 0.03 | 0.18 | 0.37 | ND | ND | ND | ND |
| S | 0.02 | 0.15 | 0.34 | ND | ND | ND | ND |
| T | 0.03 | 0.19 | 0.37 | ND | ND | ND | ND |
| U | 0.02 | 0.06 | 0.26 | ND | ND | ND | ND |
| W | >50 | 17 | >50 | ND | ND | ND | ND |
| X | >50 | 10.4 | 5 to 50 | ND | ND | ND | ND |
| Y | 11.41 | 1.4 | 5.6 | ND | ND | ND | ND |
| Z | 31 | 5.7 | >50 | ND | ND | ND | ND |
| AA | <50 | 12.4 | >50 | ND | ND | ND | ND |

ND = Not determined.

Cell Culture

PDGF Receptor Autophosphorylation Assay. Rat aorta smooth muscle cells (RASMC.) are isolated from the thoracic aorta of rats and explanted according to the method of Ross, *J. Cell. Biol.*, 1971;30:172–186. Cells are grown in Dulbecco's modified Eagle's medium (DMEM, Gibco) containing 10% fetal calf serum (FBS, Hyclone, Logan, Utah), 1% glutamine (Gibco), and 1% penicillin/streptomycin (Gibco). Cells are identified as smooth muscle cells by their "hill and valley" growth pattern and by fluorescent staining with a monoclonal antibody specific for SMC μ-actin (Sigma). RASMC are used between passages 5 and 20 for all experiments. Test compounds are prepared in dimethylsulfoxide (DMSO) in order to achieve consistency in the vehicle and to ensure compound solubility. Appropriate DMSO controls are simultaneously evaluated with the test compounds.

Rat aortic smooth muscle cells are grown to confluency in 100 mm dishes. Growth medium is removed and replaced with serum-free medium, and cells are incubated at 37° C. for an additional 24 hours. Test compounds are then added directly to the medium and cells incubated for an additional 2 hours. After 2 hours, PDGF-BB is added at a final concentration of 30 ng/mL for 5 minutes at 37° C. to stimulate autophosphorylation of PDGF receptors. Following growth factor treatment, the medium is removed, and cells are washed with cold phosphate-buffered saline and immediately lysed with 1 mL of lysis buffer (50 mM Hepes, pH 7.5, 150 mM NaCl, 10% glycerol, 1% Triton-X 100, 1 mM EDTA, 1 mM EGTA, 50 mM NaF, 1 mM sodium orthovanadate, 30 mM p-nitrophenyl phosphate, 10 mM sodium pyrophosphate, 1 mM phenylmethyl sulfonyl fluoride, 10 μg/mL aprotinin, and 10 μg/mL leupeptin). Lysates are centrifuged at 10,000×g for 10 minutes. Supernatants are incubated with 10 μL of rabbit anti-human PDGF type AB receptor antibody (1:1000) for 2 hours. Following the incubation, protein-A-sepharose beads are added for 2 hours with continuous mixing, and immune complexes bound to the beads washed four times with 1 mL lysis wash buffer. Immune complexes are solubilized in 40 μL of Laemmli sample buffer and electrophoresed in 8% to 16% SDS polyacrylamide gels. Following electrophoresis, separated proteins are transferred to nitrocellulose and immunoblotted with a 1:1000 dilution of anti-phosphotyrosine monoclonal antibody (UBI clone; 4G10; #05–321). Following extensive washing with PBS-0.2% tween-20, the blots are incubated with horseradish peroxidase labeled goat anti-mouse IgG (1:5000; Bio-Rad Inc., Hercules, Calif.), and protein levels are detected by enhanced chemiluminescence (ECL) detection system according to the instructions of the supplier (Amersham Inc., Arlington Heights, Ill.). The density of the protein bands are determined using NIH Image software (v. 1.56) and $IC_{50}$ values are generated from the densitometric data.

TABLE 2

Inhibition of PDGF-Stimulated Receptor Autophosphorylation

| Example | $IC_{50}$ (μM) |
|---------|----------------|
| F | 0.49 |
| H | >10 |
| P | 0.23 |
| S | 0.81 |

Human Colon Carcinoma Growth Delay Assay. Human colon carcinoma cells are seeded into 96-well tissue culture plates in a final volume of 180 μL of 10% fetal bovine serum containing growth media and allowed to incubate overnight (37° C., 5% $CO_2$, 95% air). Cells of the SW-620 cell line are seeded at $1.0$–$1.5 \times 10^4$ cells per well. Cells of the HCT-8 and HT-29 cell lines are seeded at $2$–$4 \times 10^3$ cells per well. Serially diluted drug solutions are prepared in growth medium at 10 times concentration; 20 μL of these solutions are added to duplicate wells and incubated with the cells for 3 days in a cell culture incubator. At the end of the incubation period, cells are fixed with 100 μL per well of 10% trichloroacetic acid after removing the drug/culture medium. The plates are washed five times with tap water and stained with 100 μL per well of 0.075% sulfrhodamine B in 1% acetic acid for 10 minutes. The plates are rinsed four times and allowed to air dry. The stain in the wells are solubilized by the addition of 10 mM unbuffered Tris base and the absorbance read using a microtiter plate optical reader. Inhibition of cell growth is calculated from absorbance data of the treated cells compared to untreated control cells.

Human Colon Carcinoma Clonozenic Assay. Human colon carcinoma cells are seeded into 6 well plates in volumes of 3 mL and allowed to incubate overnight (37° C., 5% $CO_2$, 95% air). SW-620 cells are seeded at $7 \times 10^5$ per well; HCT-8 cells are seeded at $5 \times 10^5$ per well; HT-29 cells are seeded at $4 \times 10^5$ cells per well. Serially diluted drugs are prepared at 200 times the final concentration, and 15 μL are added to each of duplicate wells. Cells are incubated with drug for 2 days, rinsed once with 1 mL of trypsin+EDTA, and then trypsinized with the same trypsin solution. After trituration and centrifugation at 750×g for 3 minutes, the cells are suspended in serum-free growth medium and counted using an electronic particle counter. An agarose mixture appropriate for the cloning of each cell line is made using 10% fetal bovine serum in growth medium (SW-620–0.35% agarose, HCT-8 and HT-29–0.4% agarose). An appropriate volume of medium containing the drug treated cells is suspended into the agarose-serum mixture to give final cell concentrations in 2.5 mL of $1.75 \times 10^4$ SW-620, $1.25 \times 10^4$ HCT-8, and $7.5 \times 10^3$ HT-29. One; milliliter of each of these cell suspensions is added to duplicate wells of 6 well plates previously prepared with 10% serum/growth medium/1% agarose plugs. The cells in these plates are incubated for approximately 2 weeks in the incubator and stained with 1 mL per well of 1 mg/mL iodonitrotetrazolium violet stain. The visible colonies are counted with an electronic optical colony counter and the clonogenicity of treated cells calculated in comparison to untreated control cells.

TABLE 3

Inhibition of Human Colon Carcinoma Cell Line Growth

| | $IC_{50}$ (μM) | | | | | |
|---------|----------------|----------------|---------------|------------------|------------------|-----------------|
| Example | HCT-8 Growth Delay | SW-620 Growth Delay | HT-29 Growth Delay | HCT-8 Clonogenic | SW-620 Clonogenic | HT-29 Clonogenic |
| F | 2.3 | 7.2 | 1.5 | >5 | >5 | >5 |
| H | 2.8 | 5.2 | 2.2 | >5 | ND | >5 |
| P | 2.8 | 6.7 | 0.8 | >5 | ND | >5 |
| S | 5.2 | 6.8 | 0.9 | ND | 2.8 | ND |

ND = Not determined.

The compounds of this invention are inhibitors of cyclin-dependent kinases, and accordingly, are useful in treating and preventing atherosclerosis, and other cell proliferative disorders like cancer. The compounds have exhibited inhibitory activity against a wide variety of cyclin-dependent kinases, all in assay systems routinely utilized to measure such activity.

Cyclin-Dependent Kinase 4 (cdk4/cyclinD) Assay

Enzyme assays for $IC_{50}$ determinations and kinetic evaluation were performed in 96-well filter plates (Millipore MADVN6550). The total volume was 0.1 mL containing a final concentration of 20 mM TRIS (tris[hydroxymethyl] aminomethane), at pH 7.4, 50 mM NaCl, 1 mM dithiothreitol, 10 mM $MgCl_2$, 25 μM ATP containing 0.25 μCi of [$^{32}$P]ATP, 20 ng of cdk4/cyclinD, 1 μg of retinoblastoma, and appropriate dilutions of a compound of the present invention. All components except the ATP were added to the wells, and the plate was placed on a plate mixer for 2 minutes. The reaction was started by adding [$^{32}$P]ATP and the plate was incubated at 25° C. for 15 minutes. The reaction was terminated by addition of 0.1 mL of 20% trichloroacetic acid (TCA). The plate was kept at 4° C. for at least 1 hour to allow the substrate to precipitate. The wells were then washed 5 times with 0.2 mL of 10% TCA and $^{32}$P incorporation was determined with a beta plate counter (Wallace Inc., Gaithersburg, Md.).

Cyclin-Dependent Kinase Assays (cdk2/cyclinE, cdk2/cyclinA, cdkl/cyclinB)

Enzyme assays for $IC_{50}$ determinations and kinetic evaluation were performed in a 96-well filter plate (Millipore MADVN6550) in a total volume of 0.1 mL of 20 mM TRIS (tris[hydroxymethyl]aminomethane), at pH 7.4, 50 mM NaCl, 1 mM dithiothreitol, 10 mM MgCl$_2$, 12 mM ATP containing 0.25 μCi of [$^{32}$P]ATP, 20 ng of enzyme (either cdk2/cyclinE, cdk2/cyclinA, or cdk1/cyclinB), 1 μg retinoblastoma, and appropriate dilutions of the particular invention compound. All components except the ATP were added to the wells, and the plate was placed on a plate mixer for 2 minutes. The reaction was begun by addition of [$^{32}$P]ATP, and the plate was incubated at 25° C. for 15 minutes. The reaction was terminated by addition of 0.1 mL of 20% TCA. The plate was kept at 4° C. for least 1 hour to allow the substrate to precipitate. The wells were then washed 5 times with 0.2 mL of 10% TCA and $^{32}$P incorporation determined with a beta plate counter (Wallace Inc., Gaithersburg, Md.).

The results of these cell cycle (CDK) assays are shown in Table 4 below.

TABLE 4

| Example | CDK4/cyclinD IC$_{50}$ μM | CDK2/cyclinE IC$_{50}$ μM | CDK2/cyclinA IC$_{50}$ μM | CDK1/cyclinB IC$_{50}$ μM |
|---|---|---|---|---|
| W | 4.2 | 1.1 | 0.88 | 1.9 |
| X | 2.6 | 1.3 | 0.83 | 1.5 |
| Y | 0.35 | 5.8 | 3.5 | 7.4 |
| Z | 1.35 | 3.0 | 1.4 | 4.0 |
| AA | 1.5 | 5.0 | ND | ND |

ND = Not determined.

What is claimed is:

1. A compound having the Formula I

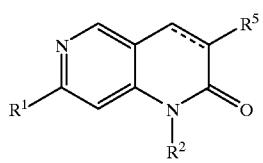

I wherein

— — — is absent or bond;

R$^1$ is

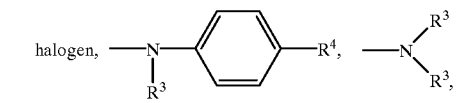

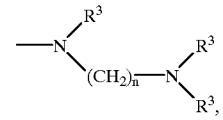, 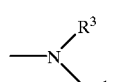

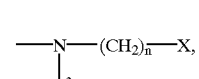

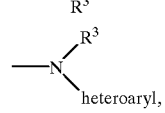 or 

R$^2$ is C$_1$–C$_6$ alkyl, C$_3$–C$_8$ cycloalkyl, or C$_5$–C$_{12}$ bicycloalkyl;

each R$^3$ is independently hydrogen or C$_1$–C$_6$ alkyl;

each n is independently 0 to 7;

R$^4$ is

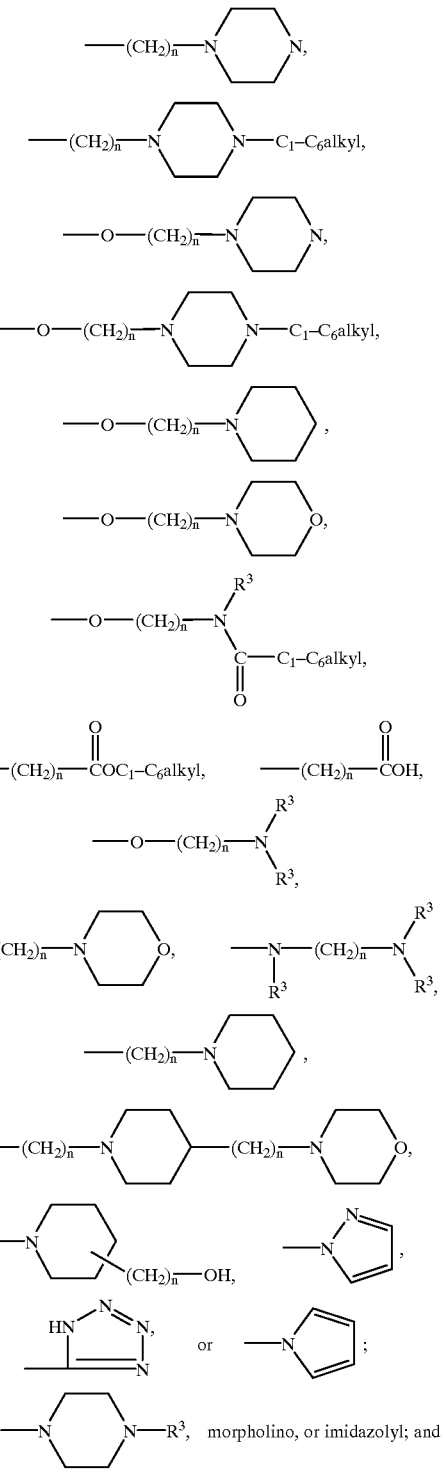

X is —N(piperazinyl)—R$^3$, morpholino, or imidazolyl; and

R$^5$ is hydrogen, aryl, substituted aryl, heteroaryl, or substituted heteroaryl, and the pharmaceutically accepted salts thereof.

2. A compound according to claim 1 wherein

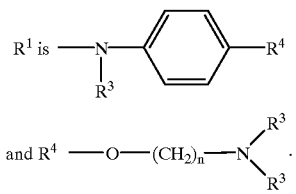

3. A compound according to claim 1 wherein

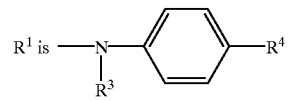

and $R^4$ is —O(CH$_2$)$_n$—X.

4. A compound according to claim 1 wherein

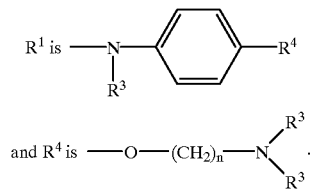

5. A compound according to claim 1 wherein

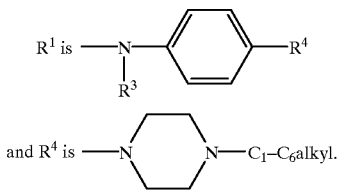

6. A compound according to claim 1 wherein $R^1$ is

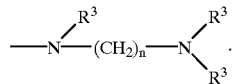

7. A compound according to claim 1 wherein $R^1$ is —NH—(CH$_2$)$_n$—N(CH$_2$CH$_3$)$_2$.

8. A compound according to claim 1 wherein $R^5$ is phenyl or substituted phenyl.

9. A compound according to claim 1 wherein $R^5$ is 2,6-dichlorophenyl.

10. A compound according to claim 1 wherein $R^2$ is methyl.

11. A compound according to claim 1 wherein $R^5$ is 2,6-dichlorophenyl and $R^2$ is methyl.

12. The compounds:
7-amino-3-(2,6-dichlorophenyl)-1-methyl-1H-[1,6]naphthyridin-2-one;
3-(2,6-dichlorophenyl)-1-methyl-7-methylamino-1H-[1,6]naphthyridin-2-one;
3-(2,6-dichlorophenyl)-7-dimethylamino-1-methyl-1H-[1,6]naphthyridin-2-one;
3-(2,6-dichlorophenyl)-7-[2-(diethylamino)ethylamino]-1-methyl-1H-[1,6]naphthyridin-2-one;
3-(2,6-dichlorophenyl)-7-[3-(diethylamino)propylamino]-1-methyl-1H-[1,6]naphthyridin-2-one;
3-(2,6-dichlorophenyl)-7-[4-(diethylamino)butylamino]-1-methyl-1H-[1,6]naphthyridin-2-one;
3-(2,6-dichlorophenyl)-7-[5-(diethylamino)pentylamino]-1-methyl-1H-[1,6]naphthyridin-2-one;
3-(2,6-dichlorophenyl)-1-methyl-7-[3-(4-methylpiperazin-1-yl)propylamino]-1H-[1,6]naphthyridin-2-one;
3-(2,6-dichlorophenyl)-1-methyl-7-[4-(4-methylpiperazin-1-yl)butylamino]-1H-[1,6]naphthyridin-2-one; and
3-(2,6-dichlorophenyl)-1-methyl-7-[5-(4-methylpiperazin-1-yl)pentylamino]-1H-[1,6]naphthyridin-2-one.

13. The compounds:
3-(2,6-dichlorophenyl)-1-methyl-7-[3-(4-morpholino)propylamino]-1H-[1,6]naphthyridin-2-one;
3-(2,6-dichlorophenyl)-7-[3-(imidazol-1-yl)propylamino]-1-methyl-1H-[1,6]naphthyridin-2-one;
3-(2,6-dichlorophenyl)-1-methyl-7-(phenylamino)-1H-[1,6]naphthyridin-2-one;
3-(2,6-dichlorophenyl)-1-methyl-7-(4-pyridylamino)-1H-[1,6]naphthyridin-2-one;
3-(2,6-dichlorophenyl)-7-[(4-methoxyphenyl)amino]-1-methyl-1H-[1,6]naphthyridin-2-one;
3-(2,6-dichlorophenyl)-7-[(4-(2-(diethylamino)ethoxy)phenyl)amino]-1-methyl-1H-[1,6]naphthyridin-2-one;
3-(2,6-dichlorophenyl)-1-methyl-7-[4-(4-morpholino)butylamino]-1H-[1,6]naphthyridin-2-one;
3-(2,6-dichlorophenyl)-7-[(4-(3-(diethylamino)propoxy)phenyl)amino]-1-methyl-1H-[1,6]naphthyridin-2-one;
3-(2,6-dichlorophenyl)-1-methyl-7-[(4-(2-(4-methylpiperazin-1-yl)ethoxy)phenyl)amino]-1H-[1,6]naphthyridin-2-one;
3-(2,6-dichlorophenyl)-1-methyl-7-[(4-(3-(4-methylpiperazin-1-yl)propoxy)phenyl)amino]-1H-[1,6]naphthyridin-2-one; and
3-(2,6-dichlorophenyl)-1-methyl-7-[(4-(4-methylpiperazin-1-yl)phenyl)amino]-1H-[1,6]naphthyridin-2-one.

14. The compounds:
7-Amino-1H-[1,6]naphthyridin-2-one;
7-Amino-1-ethyl-1H-[1,6]naphthyridin-2-one;
7-Fluoro-1-ethyl-1H-[1,6]naphthyridin-2-one;
1-Ethyl-7-phenylamino-1H-[1,6]naphthyridin-2-one;
1-Ethyl-7-(4-methoxyphenylamino)-1H-[1,6]naphthyridin-2-one;
1-Ethyl-7-[4-(4-methylpiperazin-1-yl)phenylamino]-1H-[1,6]naphthyridin-2-one;
1-Ethyl-7-(4-(morpholin-4-yl)phenylamino)-1H-[1,6]naphthyridin-2-one;
1-Ethyl-7-(4-(piperidin-1-yl)phenylamino)-1H-[1,6]naphthyridin-2-one; and
1-Ethyl-7-phenylamino-3,4-dihydro-1H-[1,6]naphthyridin-2-one.

15. The compounds:
7-[4-(2-(Diethylamino)ethoxy)phenylamino]-1-ethyl-1H-[1,6]naphthyridin-2-one;
7-[4-(3-(Diethylamino)propoxy)phenylamino]-1-ethyl-1,6-naphthyridin-2-one;
1-Ethyl-7-[4-(2-(4-methylpiperazin-1-yl)ethoxy)phenylamino]-1,6-naphthyridin-2-one;

1-Ethyl-7-[4-(3-(4-methylpiperazin-1-yl)propoxy) phenylamino]-1,6-naphthyridin-2-one;

1-Ethyl-7-(4-pyridylamino)-1H-[1,6]naphthyridin-2-one;

1-Methyl-7-[4-(4-methylpiperazin-1-yl)phenylamino]-1H-[1,6]naphthyridin-2-one;

1-Isopropyl-7-[4-(4-methylpiperazin-1-yl)phenylamino]-1H-[1,6]naphthyridin-2-one;

1-Isopentyl-7-[4-(4-methylpiperazin-1-yl)phenylamino]-1H-[1,6]naphthyridin-2-one;

1-Cyclopentyl-7-[4-(4-methylpiperazin-1-yl) phenylamino]-1H-[1,6]naphthyridin-2-one; and 1-Cyclohexyl-7-[4-(4-methylpiperazin-1-yl) phenylamino]-1H-[1,6]naphthyridin-2-one.

16. The compounds:

1-Cycloheptyl-7-[4-(4-methylpiperazin-1-yl) phenylamino]-1H-[1,6]naphthyridin-2-one;

1-Bicyclo[2.2.1]hept-2-yl-7-[4-(4-methylpiperazin-1-yl) phenylamino]-1H-[1,6]naphthyridin-2-one;

1-Methyl-7-{4-[4-(3-(morpholin-4-yl)propyl)piperidin-1-yl]phenylamino}-1H-[1,6]naphthyridin-2-one;

1-Ethyl-7-{4-[4-(3-(morpholin-4-yl)propyl)piperidin-1-yl]phenylamino}-1H-[1,6]naphthyridin-2-one;

1-Isopropyl-7-{4-[4-(3-(morpholin-4-yl)propyl) piperidin-1-yl]phenylamino}-1H-[1,6]naphthyridin-2-one;

1-Isopentyl-7-{4-[4-(3-(morpholin-4-yl)propyl) piperidin-1-yl]phenylamino}-1H-[1,6]naphthyridin-2-one;

1-Cyclopentyl-7-{4-[4-(3-(morpholin-4-yl)propyl) piperidin-1-yl]phenylamino}-1H-[1,6]naphthyridin-2-one;

1-Cyclohexyl-7-{4-[4-(3-(morpholin-4-yl)propyl) piperidin-1-yl]phenylamino}-1H-[1,6]naphthyridin-2-one;

1-Cycloheptyl-7-{4-[4-(3-(morpholin-4-yl)propyl) piperidin-1-yl]phenylamino}-1H-[1,6]naphthyridin-2-one; and 1-Bicyclo[2.2.1]hept-2-yl-7-{4-[4-(3-(morpholin-4-yl) propyl)piperidin-1-yl]phenylamino}-1H-[1,6] naphthyridin-2-one.

17. The compounds:

1-Methyl-7-{4-[4-(3-(hydroxy)propyl)piperidin-1-yl] phenylamino}-1H-[1,6]naphthyridin-2-one;

1-Ethyl-7-{4-[4-(3-(hydroxy)propyl)piperidin-1-yl] phenylamino}-1H-[1,6]naphthyridin-2-one;

7-{4-[4-(3-(Hydroxy)propyl)piperidin-1-yl] phenylamino}-1-isopropyl-1H-[1,6]naphthyridin-2-one;

7-{4-[4-(3-(Hydroxy)propyl)piperidin-1-yl] phenylamino}-1-isopentyl-1H-[1,6]naphthyridin-2-one;

1-Cyclopentyl-7-{4-[4-(3-(hydroxy)propyl)piperidin-1-yl]phenylamino}-1H-[1,6]naphthyridin-2-one;

1-Cyclohexyl-7-{4-[4-(3-(hydroxy)propyl)piperidin-1-yl]phenylamino}-1H-[1,6]naphthyridin-2-one;

1-Cycloheptyl-7-{4-[4-(3-(hydroxy)propyl)piperidin-1-yl]phenylamino}-1H-[1,6]naphthyridin-2-one;

1-Bicyclo[2.2.1]hept-2-yl-7-{4-[4-(3-(hydroxy)propyl) piperidin-1-yl]phenylamino}-1H-[1,6]naphthyridin-2-one;

1-Methyl-7-(4-(pyrazol-1-yl)phenylamino)-1H-[1,6] naphthyridin-2-one; and

1-Ethyl-7-(4-(pyrazol-1-yl)phenylamino)-1H-[1,6] naphthyridin-2-one.

18. The compounds:

1-Isopropyl-7-(4-(pyrazol-1-yl)phenylamino)-1H-[1,6] naphthyridin-2-one;

1-Isopentyl-7-(4-(pyrazol-1-yl)phenylamino)-1H-[1,6] naphthyridin-2-one;

1-Cyclopentyl-7-(4-(pyrazol-1-yl)phenylamino)-1H-[1,6]naphthyridin-2-one;

1-Cyclohexyl-7-(4-(pyrazol-1-yl)phenylamino)-1H-[1,6] naphthyridin-2-one;

1-Cycloheptyl-7-(4-(pyrazol-1-yl)phenylamino)-1H-[1,6]naphthyridin-2-one;

1-Bicyclo[2.2.1]hept-2-yl-7-(4-(pyrazol-1-yl) phenylamino)-1H-[1,6]naphthyridin-2-one;

7-(4-Fluorophenylamino)-1-methyl-1H-[1,6] naphthyridin-2-one;

1-Ethyl-7-(4-fluorophenylamino)-1H-[1,6]naphthyridin-2-one;

7-(4-Fluorophenylamino)-1-isopropyl-1H-[1,6] naphthyridin-2-one; and 7-(4-Fluorophenylamino)-1-isopentyl-1H-[1,6] naphthyridin-2-one.

19. The compounds:

1-Cyclopentyl-7-(4-fluorophenylamino)-1H-[1,6] naphthyridin-2-one;

1-Cyclohexyl-7-fluorophenylamino-1H-[1,6] naphthyridin-2-one;

1-Cycloheptyl-7-(4-fluorophenylamino)-1H-[1,6] naphthyridin-2-one;

1-Bicyclo[2.2.1]hept-2-yl-7-(4-fluorophenylamino)-1H-[1,6]naphthyridin-2-one;

7-[4-(4-(Hydroxy)piperidin-1-yl)phenylamino]-1-methyl-1H-[1,6]naphthyridin-2-one;

1-Ethyl-7-[4-(4-(hydroxy)piperidin-1-yl)phenylamino]-1H-[1,6]naphthyridin-2-one;

7-[4-(4-(Hydroxy)piperidin-1-yl)phenylamino]-1-isopropyl-1H-[1,6]naphthyridin-2-one;

7-[4-(4-(Hydroxy)piperidin-1-yl)phenylamino]-1-isopentyl-1H-[1,6]naphthyridin-2-one;

1-Cyclopentyl-7-[4-(4-(hydroxy)piperidin-1-yl) phenylamino]-1H-[1,6]naphthyridin-2-one; and 1-Cyclohexyl-7-[4-(4-(hydroxy)piperidin-1-yl) phenylamino]-1H-[1,6]naphthyridin-2-one.

20. The compounds:

1-Cycloheptyl-7-[4-(4-(hydroxy)piperidin-1-yl) phenylamino]-1H-[1,6]naphthyridin-2-one;

1-Bicyclo[2.2.1]hept-2-yl-7-[4-(4-(hydroxy)piperidin-1-yl)phenylamino]-1H-[1,6]naphthyridin-2-one;

7-[4-(3-(Hydroxymethyl)piperidin-1-yl)phenylamino]-1-methyl-1H-[1,6]naphthyridin-2-one;

1-Ethyl-7-[4-(3-(hydroxymethyl)piperidin-1-yl) phenylamino]-1H-[1,6]naphthyridin-2-one;

7-[4-(3-(Hydroxymethyl)piperidin-1-yl)phenylamino]-1-isopropyl-1H-[1,6]naphthyridin-2-one;

7-[4-(3-(Hydroxymethyl)piperidin-1-yl)phenylamino]-1-isopentyl-1H-[1,6]naphthyridin-2-one;

1-Cyclopentyl-7-[4-(3-(hydroxymethyl)piperidin-1-yl) phenylamino]-1H-[1,6]naphthyridin-2-one;

1-Cyclohexyl-7-[4-(3-(hydroxymethyl)piperidin-1-yl) phenylamino]-1H-[1,6]naphthyridin-2-one;

1-Cycloheptyl-7-[4-(3-(hydroxymethyl)piperidin-1-yl) phenylamino]-1H-[1,6]naphthyridin-2-one; and p1

1-Bicyclo[2.2.1]hept-2-yl-7-[4-(3-(hydroxymethyl)piperidin-1-yl)phenylamino]-1H-[1,6]naphthyridin-2-one.

21. The compounds:
1-Methyl-7-[4-(2H-tetrazol-5-yl)phenylamino]-1H-[1,6]naphthyridin-2-one;
1-Ethyl-7-[4-(2H-tetrazol-5-yl)phenylamino]-1H-[1,6]naphthyridin-2-one;
1-Isopropyl-7-[4-(2H-tetrazol-5-yl)phenylamino]-1H-[1,6]naphthyridin-2-one;
1-Isopentyl-7-[4-(2H-tetrazol-5-yl)phenylamino]-1H-[1,6]naphthyridin-2-one;
1-Cyclopentyl-7-[4-(2H-tetrazol-5-yl)phenylamino]-1H-[1,6]naphthyridin-2-one;
1-Cyclohexyl-7-[4-(2H-tetrazol-5-yl)phenylamino]-1H-[1,6]naphthyridin-2-one;
1-Cycloheptyl-7-[4-(2H-tetrazol-5-yl)phenylamino]-1H-[1,6]naphthyridin-2-one;
1-Bicyclo[2.2.1]hept-2-yl-7-[4-(2H-tetrazol-5-yl)phenylamino]-1H-[1,6]naphthyridin-2-one;
1-Methyl-7-(4-(piperidin-1-yl)phenylamino)-1H-[1,6]naphthyridin-2-one; and
1-Isopropyl-7-(4-(piperidin-1-yl)phenylamino)-1H-[1,6]naphthyridin-2-one.

22. The compounds:
1-Isopentyl-7-(4-(piperidin-1-yl)phenylamino)-1H-[1,6]naphthyridin-2-one;
1-Cyclopentyl-7-(4-(piperidin-1-yl)phenylamino)-1H-[1,6]naphthyridin-2-one;
1-Cyclohexyl-7-(4-(piperidin-1-yl)phenylamino)-1H-[1,6]naphthyridin-2-one;
1-Cycloheptyl-7-(4-(piperidin-1-yl)phenylamino)-1H-[1,6]naphthyridin-2-one;
1-Bicyclo[2.2.1]hept-2-yl-7-(4-(piperidin-1-yl)phenylamino)-1H-[1,6]naphthyridin-2-one;
1-Methyl-7-(4-(pyrrolidin-1-yl)phenylamino)-1H-[1,6]naphthyridin-2-one;
1-Ethyl-7-(4-(pyrrolidin-1-yl)phenylamino)-1H-[1,6]naphthyridin-2-one;
1-Isopropyl-7-(4-(pyrrolidin-1-yl)phenylamino)-1H-[1,6]naphthyridin-2-one;
1-Isopentyl-7-(4-(pyrrolidin-1-yl)phenylamino)-1H-[1,6]naphthyridin-2-one; and
1-Cyclopentyl-7-(4-(pyrrolidin-1-yl)phenylamino)-1H-[1,6]naphthyridin-2-one.

23. The compounds:
1-Cyclohexyl-7-(4-(pyrrolidin-1-yl)phenylamino)-1H-[1,6]naphthyridin-2-one;
1-Cycloheptyl-7-(4-(pyrrolidin-1-yl)phenylamino)-1H-[1,6]naphthyridin-2-one;
1-Bicyclo[2.2.1]hept-2-yl-7-(4-(pyrrolidin-1-yl)phenylamino)-1H-[1,6]naphthyridin-2-one;
1-Methyl-7-[4-(4-methylpiperazin-1-yl)phenylamino]-3,4-dihydro-1H-[1,6]naphthyridin-2-one;
1-Ethyl-7-[4-(4-methylpiperazin-1-yl)phenylamino]-3,4-dihydro-1H-[1,6]naphthyridin-2-one;
1-Isopropyl-7-[4-(4-methylpiperazin-1-yl)phenylamino]-3,4-dihydro-1H-[1,6]naphthyridin-2-one;
1-Isopentyl-7-[4-(4-methylpiperazin-1-yl)phenylamino]-3,4-dihydro-1H-[1,6]naphthyridin-2-one;
1-Cyclopentyl-7-[4-(4-methylpiperazin-1-yl)phenylamino]-3,4dihydro-1H-[1,6]naphthyridin-2-one;
1-Cyclohexyl-7-[4-(4-methylpiperazin-1-yl)phenylamino]-3,4-dihydro-1H-[1,6]naphthyridin-2-one; and
1-Cycloheptyl-7-[4-(4-methylpiperazin-1-yl)phenylamino]-3,4-dihydro-1H-[1,6]naphthyridin-2-one.

24. The compounds:
1-Bicyclo[2.2.1]hept-2-yl-7-[4-(4-methylpiperazin-1-yl)phenylamino]-3,4-dihydro-1H-[1,6]naphthyridin-2-one;
1-Methyl-7-{4-[4-(3-(morpholin-4-yl)propyl)piperidin-1-yl]-phenylamino}-3,4-dihydro-1H-[1,6]naphthyridin-2-one;
1-Ethyl-7-{4-[4-(3-(morpholin-4-yl)propyl)piperidin-1-yl]phenylamino}-3,4-dihydro-1H-[1,6]naphthyridin-2-one;
1-Isopropyl-7-{4-[4-(3-(morpholin-4-yl)propyl)piperidin-1-yl]phenylamino}-3,4-dihydro-1H-[1,6]naphthyridin-2-one;
1-Isopentyl-7-{4-[4-(3-(morpholin-4-yl)propyl)piperidin-1-yl]phenylamino}-3,4-dihydro-1H-[1,6]naphthyridin-2-one;
1-Cyclopentyl-7-{4-[4-(3-(morpholin-4-yl)propyl)piperidin-1-yl]phenylamino}-3,4-dihydro-1H-[1,6]naphthyridin-2-one;
1-Cyclohexyl-7-{4-[4-(3-(morpholin-4-yl)propyl)piperidin-1-yl]phenylamino}-3,4-dihydro-1H-[1,6]naphthyridin-2-one;
1-Cycloheptyl-7-{4-[4-(3-(morpholin-4-yl)propyl)piperidin-1-yl]phenylamino}-3,4-dihydro-1H-[1,6]naphthyridin-2-one;
1-Bicyclo[2.2.1]hept-2-yl-7-{4-[4-(3-(morpholin-4-yl)propyl)piperidin-1-yl]phenylamino}-3,4-dihydro-1H-[1,6]naphthyridin-2-one; and
1-Methyl-7-{4-[4-(3-(hydroxy)propyl)piperidin-1-yl]phenylamino}-3,4-dihydro-1H-[1,6]naphthyridin-2-one.

25. The compounds:
1-Ethyl-7-{4-[4-(3-(hydroxy)propyl)piperidin-1-yl]phenylamino}-3,4-dihydro-1H-[1,6]naphthyridin-2-one;
7-{4-[4-(3-(Hydroxy)propyl)piperidin-1-yl]phenylamino}-1-isopropyl-3,4-dihydro-1H-[1,6]naphthyridin-2-one;
7-{4-[4-(3-(Hydroxy)propyl)piperidin-1-yl]phenylamino}-1-isopentyl-3,4-dihydro-1H-[1,6]naphthyridin-2-one;
1-Cyclopentyl-7-{4-[4-(3-(hydroxy)propyl)piperidin-1-yl]phenylamino}-3,4-dihydro-1H-[1,6]naphthyridin-2-one;
1-Cyclohexyl-7-{4-[4-(3-(hydroxy)propyl)piperidin-1-yl]phenylamino}-3,4-dihydro-1H-[1,6]naphthyridin-2-one;
1-Cycloheptyl-7-{4-[4-(3-hydroxy)propyl)piperidin-1-yl]phenylamino}-3,4-dihydro-1H-[1,6]naphthyridin-2-one;
1-Bicyclo[2.2.1]hept-2-yl-7-{4-[4-(3-(hydroxy)propyl)piperidin-1-yl]phenylamino}-3,4-dihydro-1H-[1,6]naphthyridin-2-one;
1-Methyl-7-(4-(pyrazol-1-yl)phenylamino)-3,4-dihydro-1H-[1,6]naphthyridin-2-one;
1-Ethyl-7-(4-(pyrazol-1-yl)phenylamino)-3,4-dihydro-1H-[1,6]naphthyridin-2-one; and 1-Isopropyl-7-(4-(pyrazol-1-yl)phenylamino)-3,4-dihydro-1H-[1,6]naphthyridin-2-one.

26. The compounds:

1-Isopentyl-7-(4-(pyrazol-1-yl)phenylamino)-3,4-dihydro-1H-[1,6]naphthyridin-2-one;

1-Cyclopentyl-7-(4-(pyrazol-1-yl)phenylamino)-3,4-dihydro-1H-[1,6]naphthyridin-2-one;

1-Cyclohexyl-7-(4-(pyrazol-1-yl)phenylamino)-3,4-dihydro-1H-[1,6]naphthyridin-2-one;

1-Cycloheptyl-7-(4-(pyrazol-1-yl)phenylamino)-3,4-dihydro-1H-[1,6]naphthyridin-2-one;

1-Bicyclo[2.2.1]hept-2-yl-7-(4-(pyrazol-1-yl)phenylamino)-3,4-dihydro-1H-[1,6]naphthyridin-2-one;

7-(4-Fluorophenylamino)-1-methyl-3,4-dihydro-1H-[1,6]naphthyridin-2-one;

1-Ethyl-7-(4-fluorophenylamino)-3,4-dihydro-1H-[1,6]naphthyridin-2-one;

7-(4-Fluorophenylamino)-1-isopropyl-3,4-dihydro-1H-[1,6]naphthyridin-2-one;

7-(4-Fluorophenylamino)-1-isopentyl-3,4-dihydro-1H-[1,6]naphthyridin-2-one; and

1-Cyclopentyl-7-(4-fluorophenylamino)-3,4-dihydro-1H-[1,6]naphthyridin-2-one.

27. The compounds:

1-Cyclohexyl-7-(4-fluorophenylamino)-3,4-dihydro-1H-[1,6]naphthyridin-2-one;

1-Cycloheptyl-7-(4-fluorophenylamino)-3,4-dihydro-1H-[1,6]naphthyridin-2-one;

1- Bicyclo[2.2.1]hept-2-yl-7-(4-fluorophenylamino)-3,4-dihydro-1H-[1,6]naphthyridin-2-one;

7-[4-(4-(Hydroxy)piperidin-1-yl)phenylamino]-1-methyl-3,4-dihydro-1H-[1,6]naphthyridin-2-one;

1-Ethyl-7-[4-(4-(hydroxy)piperidin-1-yl)phenylamino]-3,4-dihydro-1H-[1,6]naphthyridin-2-one;

7-[4-(4-(Hydroxy)piperidin-1-yl)phenylamino]-1-isopropyl-3,4-dihydro-1H-[1,6]naphthyridin-2-one;

7-[4-(4-(Hydroxy)piperidin-1-yl)phenylamino]-1-isopentyl-3,4-dihydro-1H-[1,6]naphthyridin-2-one;

1-Cyclopentyl-7-[4-(4-(hydroxy)piperidin-1-yl)phenylamino]-3,4-dihydro-1H-[1,6]naphthyridin-2-one;

1-Cyclohexyl-7-[4-(4-(hydroxy)piperidin-1-yl)phenylamino]-3,4-dihydro-1H-[1,6]naphthyridin-2-one; and 1-Cycloheptyl-7-[4-(4-(hydroxy)piperidin-1-yl)phenylamino]-3,4dihydro-1H-[1,6]naphthyridin-2-one.

28. The compounds:

1-Bicyclo[2.2.1]hept-2-yl-7-[4-(4-(hydroxy)piperidin-1-yl)phenylamino]-3,4-dihydro-1H-[1,6]naphthyridin-2-one;

7-[4-(3-(Hydroxymethyl)piperidin-1-yl)phenylamino]-1-methyl-3,4-dihydro-1H-[1,6]naphthyridin-2-one;

1-Ethyl-7-[4-(3-(hydroxymethyl)piperidin-1-yl)phenylamino]-3,4-dihydro-1H-[1,6]naphthyridin-2-one;

7-[4-(3-(Hydroxymethyl)piperidin-1-yl)phenylamino]-1-isopropyl-3,4-dihydro-1H-[1,6]naphthyridin-2-one;

7-[4-(3-(Hydroxymethyl)piperidin-1-yl)phenylamino]-1-isopentyl-3,4-dihydro-1H-[1,6]naphthyridin-2-one;

1-Cyclopentyl-7-[4-(3-(hydroxymethyl)piperidin-1-yl)phenylamino]-3,4-dihydro-1H-[1,6]naphthyridin-2-one;

1-Cyclohexyl-7-[4-(3-(hydroxymethyl)piperidin-1-yl)phenylamino]-3,4-dihydro-1H-[1,6]naphthyridin-2-one;

1-Cycloheptyl-7-[4-(3-(hydroxymethyl)piperidin-1-yl)phenylamino]-3,4-dihydro-1H-[1,6]naphthyridin-2-one;

1-Bicyclo[2.2.1]hept-2-yl-7-[4-(3-(hydroxymethyl)piperidin-1-yl)phenylamino]-3,4-dihydro-1H-[1,6]naphthyridin-2-one; and 1-Methyl-7-[4-(2H-tetrazol-5-yl)phenylamino]-3,4-dihydro-1H-[1,6]naphthyridin-2-one.

29. The compounds:

1-Ethyl-7-[4-(2H-tetrazol-5-yl)phenylamino]-3,4-dihydro-1H-[1,6]naphthyridin-2-one;

1-Isopropyl-7-[4-(2H-tetrazol-5-yl)phenylamino]-3,4-dihydro-1H-[1,6]naphthyridin-2-one;

1-Isopentyl-7-[4-(2H-tetrazol-5-yl)phenylamino]-3,4-dihydro-1H-[1,6]naphthyridin-2-one;

1-Cyclopentyl-7-[4-(2H-tetrazol-5-yl)phenylamino]-3,4-dihydro-1H-[1,6]naphthyridin-2-one;

1-Cyclohexyl-7-[4-(2H-tetrazol-5-yl)phenylamino]-3,4dihydro-1H-[1,6]naphthyridin-2-one;

1-Cycloheptyl-7-[4-(2H-tetrazol-5-yl)phenylamino]-3,4-dihydro-1H-[1,6]naphthyridin-2-one;

1-Bicyclo[2.2.1]hept-2-yl-7-[4-(2H-tetrazol-5-yl)phenylamino]-3,4-dihydro-1H-[1,6]naphthyridin-2-one;

1-Methyl-7-(4-(piperidin-1-yl)phenylamino)-3,4-dihydro-1H-[1,6]naphthyridin-2-one;

1-Ethyl-7-(4-(piperidin-1-yl)phenylamino)-3,4-dihydro-1H-[1,6]naphthyridin-2-one; and 1-Isopropyl-7-(4-(piperidin-1-yl)phenylamino)-3,4-dihydro-1H-[1,6]naphthyridin-2-one.

30. The compounds:

1-Isopentyl-7-(4-(piperidin-1-yl)phenylamino)-3,4-dihydro-1H-[1,6]naphthyridin-2-one;

1-Cyclopentyl-7-(4-(piperidin-1-yl)phenylamino)-3,4-dihydro-1H-[1,6]naphthyridin-2-one;

1-Cyclohexyl-7-(4-(piperidin-1-yl)phenylamino)-3,4-dihydro-1H-[1,6]naphthyridin-2-one;

1-Cycloheptyl-7-(4-(piperidin-1-yl)phenylamino)-3,4-dihydro-1H-[1,6]naphthyridin-2-one;

1-Bicyclo[2.2.1]hept-2-yl-7-(4-(piperidin-1-yl)phenylamino)-3,4-dihydro-1H-[1,6]naphthyridin-2-one;

1-Methyl-7-(4-(pyrrolidin-1-yl)phenylamino)-3,4-dihydro-1H-[1,6]naphthyridin-2-one;

1-Ethyl-7-(4-(pyrrolidin-1-yl)phenylamino)-3,4-dihydro-1H-[1,6]naphthyridin-2-one;

1-Isopropyl-7-(4-(pyrrolidin-1-yl)phenylamino)-3,4-dihydro-1H-[1,6]naphthyridin-2-one;

1-Isopentyl-7-(4-(pyrrolidin-1-yl)phenylamino)-3,4-dihydro-1H-[1,6]naphthyridin-2-one; and 1-Cyclopentyl-7-(4-(pyrrolidin-1-yl)phenylamino)-3,4-dihydro-1H-[1,6]naphthyridin-2-one.

31. The compounds:

1-Cyclohexyl-7-(4-(pyrrolidin-1-yl)phenylamino)-3,4-dihydro-1H-[1,6]naphthyridin-2-one;

1-Cycloheptyl-7-(4-(pyrrolidin-1-yl)phenylamino)-3,4-dihydro-1H-[1,6]naphthyridin-2-one;

1-Bicyclo[2.2.1]hept-2-yl-7-(4-(pyrrolidin-1-yl)phenylamino)-3,4-dihydro-1H-[1,6]naphthyridin-2-one;

3-Fluoro-1-methyl-7-[4-(4-methylpiperazin-1-yl)phenylamino]-1H-[1,6]naphthyridin-2-one;
1-Ethyl-3-fluoro-7-[4-(4-methylpiperazin-1-yl)phenylamino]-1H-[1,6]naphthyridin-2-one;
3-Fluoro-1-isopropyl-7-[4-(4-methylpiperazin-1-yl)phenylamino]-1H-[1,6]naphthyridin-2-one;
3-Fluoro-1-isopentyl-7-[4-(4-methylpiperazin-1-yl)phenylamino]-1H-[1,6]naphthyridin-2-one;
1-Cyclopentyl-3-fluoro-7-[4-(4-methylpiperazin-1-yl)phenylamino]-1H-[1,6]naphthyridin-2-one;
1-Cyclohexyl-3-fluoro-7-[4-(4-methylpiperazin-1-yl)phenylamino]-1H-[1,6]naphthyridin-2-one; and
1-Cycloheptyl-3-fluoro-7-[4-(4-methylpiperazin-1-yl)phenylamino]-1H-[1,6]naphthyridin-2-one.

32. The compounds:
1-Bicyclo[2.2.1]hept-2-yl-3-fluoro-7-[4-(4-methylpiperazin-1-yl)phenylamino]-1H-[1,6]naphthyridin-2-one;
3-Fluoro-1-methyl-7-{4-[4-(3-(morpholin-4-yl)propyl)piperidin-1-yl]phenylamino}-1H-[1,6]naphthyridin-2-one;
1-Ethyl-3-fluoro-7-{4-[4-(3-(morpholin-4-yl)propyl)piperidin-1-yl]phenylamino}-1H-[1,6]naphthyridin-2-one;
3-Fluoro-1-isopropyl-7-{4-[4-(3-(morpholin-4-yl)propyl)piperidin-1-yl]phenylamino}-1H-[1,6]naphthyridin-2-one;
3-Fluoro-1-isopentyl-7-{4-[4-(3-(morpholin-4-yl)propyl)piperidin-1-yl]phenylamino}-1H-[1,6]naphthyridin-2-one;
1-Cyclopentyl-3-fluoro-7-{4-[4-(3-(morpholin-4-yl)propyl)piperidin-1-yl]phenylamino}-1H-[1,6]naphthyridin-2-one;
1-Cyclohexyl-3-fluoro-7-{4-[4-(3-(morpholin-4-yl)propyl)piperidin-1-yl]phenylamino}-1H-[1,6]naphthyridin-2-one;
1-Cycloheptyl-3-fluoro-7-{4-[4-(3-(morpholin-4-yl)propyl)piperidin-1-yl]phenylamino}-1H-[1,6]naphthyridin-2-one;
1-Bicyclo[2.2.1]hept-2-yl-3-fluoro-7-{4-[4-(3-(morpholin-4-yl)propyl)piperidin-1-yl]phenylamino}-1H-[1,6]naphthyridin-2-one; and
3-Fluoro-1-methyl-7-{4-[4-(3-(hydroxy)propyl)piperidin-1-yl]phenylamino}-1H-[1,6]naphthyridin-2-one.

33. The compounds:
1-Ethyl-3-fluoro-7-{4-[4-(3-(hydroxy)propyl)piperidin-1-yl]phenylamino}-1H-[1,6]naphthyridin-2-one;
3-Fluoro-7-{4-[4-(3-(hydroxy)propyl)piperidin-1-yl]phenylamino}-1-isopropyl-1H-[1,6]naphthyridin-2-one;
3-Fluoro-7-{4-[4-(3-(hydroxy)propyl)piperidin-1-yl]phenylamino}-1-isopentyl-1H-[1,6]naphthyridin-2-one;
1-Cyclopentyl-3-fluoro-7-{4-[4-(3-(hydroxy)propyl)piperidin-1-yl]phenylamino}-1H-[1,6]naphthyridin-2-one;
1-Cyclohexyl-3-fluoro-7-{4-[4-(3-(hydroxy)propyl)piperidin-1-yl]phenylamino}-1H-[1,6]naphthyridin-2-one;
1-Cycloheptyl-3-fluoro-7-{4-[4-(3-(hydroxy)propyl)piperidin-1-yl]phenylamino}-1H-[1,6]naphthyridin-2-one;
1-Bicyclo[2.2.1]hept-2-yl-3-fluoro-7-{4-[4-(3-(hydroxy)propyl)piperidin-1-yl]phenylamino}-1H-[1,6]naphthyridin-2-one;
3-Fluoro-1-methyl-7-(4-(pyrazol-1-yl)phenylamino)-1H-[1,6]naphthyridin-2-one;
1-Ethyl-3-fluoro-7-(4-(pyrazol-1-yl)phenylamino)-1H-[1,6]naphthyridin-2-one; and
3-Fluoro-1-isopropyl-7-(4-(pyrazol-1-yl)phenylamino)-1H-[1,6]naphthyridin-2-one.

34. The compounds:
3-Fluoro-1-isopentyl-7-(4-(pyrazol-1-yl)phenylamino)-1H-[1,6]naphthyridin-2-one;
1-Cyclopentyl-3-fluoro-7-(4-(pyrazol-1-yl)phenylamino)-1H-[1,6]naphthyridin-2-one;
1-Cyclohexyl-3-fluoro-7-(4-(pyrazol-1-yl)phenylamino)-1H-[1,6]naphthyridin-2-one;
1-Cycloheptyl-3-fluoro-7-(4-(pyrazol-1-yl)phenylamino)-1H-[1,6]naphthyridin-2-one;
1-Bicyclo[2.2.1]hept-2-yl-3-fluoro-7-(4-(pyrazol-1-yl)phenylamino)-1H-[1,6]naphthyridin-2-one;
3-Fluoro-7-(4-fluorophenylamino)-1-methyl-1H-[1,6]naphthyridin-2-one;
1-Ethyl-3-fluoro-7-(4-fluorophenylamino)-1H-[1,6]naphthyridin-2-one;
3-Fluoro-7-(4-fluorophenylamino)-1-isopropyl-1H-[1,6]naphthyridin-2-one;
3-Fluoro-7-(4-fluorophenylamino)-1-isopentyl-1H-[1,6]naphthyridin-2-one; and
1-Cyclopentyl-3-fluoro-7-(4-fluorophenylamino-1H-[1,6]naphthyridin-2-one.

35. The compounds:
1-Cyclohexyl-3-fluoro-7-(4-fluorophenylamino)-1H-[1,6]naphthyridin-2-one;
1-Cycloheptyl-3-fluoro-7-(4-fluorophenylamino)-1H-[1,6]naphthyridin-2-one;
1-Bicyclo[2.2.1]hept-2-yl-3-fluoro-7-(4-fluorophenylamino)-1H-[1,6]naphthyridin-2-one;
3-Fluoro-7-[4-(4-(hydroxy)piperidin-1-yl)phenylamino]-1-methyl-1H-[1,6]naphthyridin-2-one;
1-Ethyl-3-fluoro-7-[4-(4-(hydroxy)piperidin-1-yl)phenylamino]-1H-[1,6]naphthyridin-2-one;
3-Fluoro-7-[4-(4-(hydroxy)piperidin-1-yl)phenylamino]-1-isopropyl-1H-[1,6]naphthyridin-2-one;
3-Fluoro-7-[4-(4-(hydroxy)piperidin-1-yl)phenylamino]-1-isopentyl-1H-[1,6]naphthyridin-2-one;
1-Cyclopentyl-3-fluoro-7-[4-(4-(hydroxy)piperidin-1-yl)phenylamino]-1H-[1,6]naphthyridin-2-one;
1-Cyclohexyl-3-fluoro-7-[4-(4-(hydroxy)piperidin-1-yl)phenylamino]-1H-[1,6]naphthyridin-2-one; and
1-Cycloheptyl-3-fluoro-7-[4-(4-(hydroxy)piperidin-1-yl)phenylamino]-1H-[1,6]naphthyridin-2-one.

36. The compounds:
1-Bicyclo[2.2.1]hept-2-yl-3-fluoro-7-[4-(4-(hydroxy)piperidin-1-yl)phenylamino]-1H-[1,6]naphthyridin-2-one;
3-Fluoro-7-[4-(3-(hydroxymethyl)piperidin-1-yl)phenylamino]-1-methyl-1H-[1,6]naphthyridin-2-one;
1-Ethyl-3-fluoro-7-[4-(3-(hydroxymethyl)piperidin-1-yl)phenylamino]-1H-[1,6]naphthyridin-2-one;
3-Fluoro-7-[4-(3-(hydroxymethyl)piperidin-1-yl)phenylamino]-1-isopropyl-1H-[1,6]naphthyridin-2-one;

3-Fluoro-7-[4-(3-(hydroxymethyl)piperidin-1-yl)phenylamino]-1-isopentyl-1H-[1,6]naphthyridin-2-one;

1-Cyclopentyl-3-fluoro-7-[4-(3-(hydroxymethyl)piperidin-1-yl)phenylamino]-1H-[1,6]naphthyridin-2-one;

1-Cyclohexyl-3-fluoro-7-[4-(3-(hydroxymethyl)piperidin-1-yl)phenylamino]-1H-[1,6]naphthyridin-2-one;

1-Cycloheptyl-3-fluoro-7-[4-(3-(hydroxymethyl)piperidin-1-yl)phenylamino]-1H-[1,6]naphthyridin-2-one;

1-Bicyclo[2.2.1]hept-2-yl-3-fluoro-7-[4-(3-(hydroxymethyl)piperidin-1-yl)phenylamino]-1H-[1,6]naphthyridin-2-one; and 3-Fluoro-1-methyl-7-[4-(2H-tetrazol-5-yl)phenylamino]-1H-[1,6]naphthyridin-2-one.

37. The compounds:

1-Ethyl-3-fluoro-7-[4-(2H-tetrazol-5-yl)phenylamino]-1H-[1,6]naphthyridin-2-one;

3-Fluoro-1-isopropyl-7-[4-(2H-tetrazol-5-yl)phenylamino]-1H-[1,6]naphthyridin-2-one;

3-Fluoro-1-isopentyl-7-[4-(2H-tetrazol-5-yl)phenylamino]-1H-[1,6]naphthyridin-2-one;

1-Cyclopentyl-3-fluoro-7-[4-(2H-tetrazol-5-yl)phenylamino]-1H-[1,6]naphthyridin-2-one;

1-Cyclohexyl-3-fluoro-7-[4-(2H-tetrazol-5-yl)phenylamino]-1H-[1,6]naphthyridin-2-one;

1-Cycloheptyl-3-fluoro-7-[4-(2H-tetrazol-5-yl)phenylamino]-1H-[1,6]naphthyridin-2-one;

1-Bicyclo[2.2.1]hept-2-yl-3-fluoro-7-[4-(2H-tetrazol-5-yl)phenylamino]-1H-[1,6]naphthyridin-2-one;

3-Fluoro-1-methyl-7-(4-(piperidin-1-yl)phenylamino)-1H-[1,6]naphthyridin-2-one;

1-Ethyl-3-fluoro-7-(4-(piperidin-1-yl)phenylamino)-1H-[1,6]naphthyridin-2-one; and 3-Fluoro-1-isopropyl-7-(4-(piperidin-1-yl)phenylamino)-1H-[1,6]naphthyridin-2-one.

38. The compounds:

3-Fluoro-1-isopentyl-7-(4-(piperidin-1-yl)phenylamino)-1H-[1,6]naphthyridin-2-one;

1-Cyclopentyl-3-fluoro-7-(4-(piperidin-1-yl)phenylamino)-1H-[1,6]naphthyridin-2-one;

1-Cyclohexyl-3-fluoro-7-(4-(piperidin-1-yl)phenylamino)-1H-[1,6]naphthyridin-2-one;

1-Cycloheptyl-3-fluoro-7-(4-(piperidin-1-yl)phenylamino)-1H-[1,6]naphthyridin-2-one;

1-Bicyclo[2.2.1]hept-2-yl-3-fluoro-7-(4-(piperidin-1-yl)phenylamino)-1H-[1,6]naphthyridin-2-one;

3-Fluoro-1-methyl-7-(4-(pyrrolidin-1-yl)phenylamino)-1H-[1,6]naphthyridin-2-one;

1-Ethyl-3-fluoro-7-(4-(pyrrolidin-1-yl)phenylamino)-1H-[1,6]naphthyridin-2-one;

3-Fluoro-1-isopropyl-7-(4-(pyrrolidin-1-yl)phenylamino)-1H-[1,6]naphthyridin-2-one;

3-Fluoro-1-isopentyl-7-(4-(pyrrolidin-1-yl)phenylamino)-1H-[1,6]naphthyridin-2-one; and 1-Cyclopentyl-3-fluoro-7-(4-(pyrrolidin-1-yl)phenylamino)-1H-[1,6]naphthyridin-2-one.

39. The compounds:

1-Cyclohexyl-3-fluoro-7-(4-(pyrrolidin-1-yl)phenylamino)-1H-[1,6]naphthyridin-2-one;

1-Cycloheptyl-3-fluoro-7-(4-(pyrrolidin-1-yl)phenylamino)-1H-[1,6]naphthyridin-2-one;

1-Bicyclo[2.2.1]hept-2-yl-3-fluoro-7-(4-(pyrrolidin-1-yl)phenylamino)-1H-[1,6]naphthyridin-2-one;

3-(2,6-Dichlorophenyl)-7-(4-fluoro-3-methylphenylamino)-1-methyl-1H-[1,6]naphthyridin-2-one;

3-(2,6-Dichlorophenyl)-7-(4-ethoxyphenylamino)-1-methyl-1H-[1,6]naphthyridin-2-one;

3-(2,6-Dichlorophenyl)-7-(3-(hydroxymethyl)phenylamino)-1-methyl-1H-[1,6]naphthyridin-2-one;

3-(2,6-Dichlorophenyl)-1-methyl-7-(4-(morpholin-4-yl)phenylamino)-1H-[1,6]naphthyridin-2-one;

3-(2,6-Dichlorophenyl)-1-methyl-7-[4-(2-(morpholin-4-yl)ethoxy)phenylamino]-1H-[1,6]naphthyridin-2-one;

3-(2,6-Dichlorophenyl)-1-methyl-7-[4-(2-(piperidin-1-yl)ethoxy)phenylamino]-1H-[1,6]naphthyridin-2-one; and 3-(2,6-Dichlorophenyl)-1-methyl-7-[4-(4-(methylpiperazin-1-yl)methyl)phenylamino]-1H-[1,6]naphthyridin-2-one.

40. The compounds:

3-(2,6-Dichlorophenyl)-7-[4-(2-(dimethylamino)ethoxy)phenylamino]-1-methyl-1H-[1,6]naphthyridin-2-one;

3-[3-(2,6-Dichlorophenyl)-1-methyl-2-oxo-1,2-dihydro-[1,6]naphthyridin-7-ylamino]-benzoic acid;

3-(2,6-Dichlorophenyl)-7-[3-(2-(diethylamino)ethoxy)phenylamino]-1-methyl-1H-[1,6]naphthyridin-2-one;

N-(2-{4-[3-(2,6-Dichlorophenyl)-1-methyl-2-oxo-1,2-dihydro-[1,6]naphthyridin-7-ylamino]phenoxy}ethyl)-N-ethyl-acetamide;

{4-[3-(2,6-Dichlorophenyl)-1-methyl-2-oxo-1,2-dihydro-[1,6]naphthyridin-7-ylamino]phenyl}-acetic acid; and 3-(2,6-Dichlorophenyl)-1-ethyl-7-(4-fluoro-3-methylphenylamino)-1H-[1,6]naphthyridin-2-one.

41. The compounds:

3-(2,6-Dichlorophenyl)-7-(4-ethoxyphenylamino)-1-ethyl-1H-[1,6]naphthyridin-2-one;

3-(2,6-Dichlorophenyl)-1-ethyl-7-(3-(hydroxymethyl)phenylamino)-1H-[1,6]naphthyridin-2-one;

3-(2,6-Dichlorophenyl)-1-ethyl-7-(4-(morpholin-4-yl)phenylamino)-1H-[1,6]naphthyridin-2-one;

3-(2,6-Dichlorophenyl)-7-[4-(2-(diethylamino)ethoxy)phenylamino]-1-ethyl-1H-[1,6]naphthyridin-2-one;

3-(2,6-Dichlorophenyl)-1-ethyl-7-[4-(2-(morpholin-4-yl)ethoxy)phenylamino]-1H-[1,6]naphthyridin-2-one;

3-(2,6-Dichlorophenyl)-1-ethyl-7-[4-(2-(piperidin-1-yl)ethoxy)phenylamino]-1H-[1,6]naphthyridin-2-one;

3-(2,6-Dichlorophenyl)-1-ethyl-7-[4-(4-(methylpiperazin-1-yl)methyl)phenylamino]-1H-[1,6]naphthyridin-2-one;

3-(2,6-Dichlorophenyl)-7-[4-(2-(dimethylamino)ethoxy)phenylamino]-1-ethyl-1H-[1,6]naphthyridin-2-one;

3-[3-(2,6-Dichlorophenyl)-1-ethyl-2-oxo-1,2-dihydro-[1,6]naphthyridin-7-ylamino]-benzoic acid;

3-(2,6-Dichlorophenyl)-7-[3-(2-(diethylamino)ethoxy)phenylamino]-1-ethyl-1H-[1,6]naphthyridin-2-one;

N-(2-{4-[3-(2,6-Dichlorophenyl)-1-ethyl-2-oxo-1,2-dihydro-[1,6]naphthyridin-7-ylamino]phenoxy}ethyl)-N-ethyl-acetamide;

3-(2,6-Dichlorophenyl)-1-ethyl-7-(4-pyridylamino)-1H-[1,6]naphthyridin-2-one;

3-(2,6-Dichlorophenyl)-1-ethyl-7-[4-(4-methylpiperazin-1-yl)phenylamino]-1H-[1,6]naphthyridin-2-one; and {4-[3-(2,6-Dichlorophenyl)-1-ethyl-2-oxo-1,2-dihydro-[1,6]naphthyridin-7-ylamino]phenyl}-acetic acid.

42. The compounds:

3-(3,5-Dimethoxyphenyl)-1-methyl-7-[3-(4-methylpiperazin-1-yl)propylamino]-1H-[1,6]naphthyridin-2-one;

3-(3,5-Dimethoxyphenyl)-1-ethyl-7-[3-(4-methylpiperazin-1-yl)propylamino]-1H-[1,6]naphthyridin-2-one;

7-(4-(Diethylamino)butylamino)-3-(3,5-dimethoxyphenyl)-1-methyl-1H-[1,6]naphthyridin-2-one;

7-(4-(Diethylamino)butylamino)-3-(3,5-dimethoxyphenyl)-1-ethyl-1H-[1,6]naphthyridin-2-one;

7-[4-(2-(Diethylamino)ethoxy)phenylamino]-3-(3,5-dimethoxyphenyl)-1-ethyl-1H-[1,6]naphthyridin-2-one;

7-[4-(2-(Diethylamino)ethoxy)phenylamino]-3-(3,5-dimethoxyphenyl)-1-methyl-1H-[1,6]naphthyridin-2-one;

3-(3,5-Dimethoxyphenyl)-1-ethyl-7-(4-pyridylamino)-1H-[1,6]naphthyridin-2-one;

3-(3,5-Dimethoxyphenyl)-1-methyl-7-(4-pyridylamino)-1H-[1,6]naphthyridin-2-one;

3-(2,6-Dichloro-3,5-dimethoxyphenyl)-1-methyl-7-[3-(4-methylpiperazin-1-yl)propylamino]-1H-[1,6]naphthyridin-2-one; and 3-(2-Chloro-3,5-dimethoxyphenyl)-1-methyl-7-[3-(4-methylpiperazin-1-yl)propylamino]-1H-[1,6]naphthyridin-2-one.

43. The compounds:

3-(2,6-Dimethyl-3,5-dimethoxyphenyl)-1-methyl-7-[3-(4-methylpiperazin-1-yl)propylamino]-1H-[1,6]naphthyridin-2-one;

1-Methyl-3-(2-methyl-3,5-dimethoxyphenyl)-7-[3-(4-methylpiperazin-1-yl)propylamino]-1H-[1,6]naphthyridin-2-one;

3-(2,6-Dichloro-3,5-dimethoxyphenyl)-1-ethyl-7-[3-(4-methylpiperazin-1-yl)propylamino]-1H-[1,6]naphthyridin-2-one;

3-(2-Chloro-3,5-dimethoxyphenyl)-1-ethyl-7-[3-(4-methylpiperazin-1-yl)propylamino]-1H-[1,6]naphthyridin-2-one;

3-(2,6-Dimethyl-3,5-dimethoxyphenyl)-1-ethyl-7-[3-(4-methylpiperazin-1-yl)propylamino]-1H-[1,6]naphthyridin-2-one;

1-Ethyl-3-(2-methyl-3,5-dimethoxyphenyl)-7-[3-(4-methylpiperazin-1-yl)propylamino]-1H-[1,6]naphthyridin-2-one;

3-(2,6-Dichloro-3,5-dimethoxyphenyl)-7-(4-(diethylamino)butylamino)-1-methyl-1H-[1,6]naphthyridin-2-one;

3-(2-Chloro-3,5-dimethoxyphenyl)-7-(4-(diethylamino)butylamino)-1-methyl-1H-[1,6]naphthyridin-2-one;

7-(4-(Diethylamino)butylamino)-1-methyl-3-(2-methyl-3,5-dimethoxyphenyl)-1H-[1,6]naphthyridin-2-one; and 3-(2,6-Dimethyl-3,5-dimethoxyphenyl)-7-(4-(diethylamino)butylamino)-1-methyl-1H-[1,6]naphthyridin-2-one.

44. The compounds:

3-(2,6-Dichloro-3,5-dimethoxyphenyl)-7-(4-(diethylamino)butylamino)-1-ethyl-1H-[1,6]naphthyridin-2-one;

3-(2-Chloro-3,5-dimethoxyphenyl)-7-(4-(diethylamino)butylamino)-1-ethyl-1H-[1,6]naphthyridin-2-one;

7-(4-(Diethylamino)butylamino)-1-ethyl-3-(2-methyl-3,5-dimethoxyphenyl)-1H-[1,6]naphthyrdin-2-one;

7-(4-(Diethylamino)butylamino)-3-(2,6-dimethyl-3,5-dimethoxyphenyl)-1-ethyl-1H-[1,6]naphthyridin-2-one;

3-(2,6-Dichloro-3,5-dimethoxyphenyl)-7-[4-(2-(diethylamino)ethoxy)phenylamino]-1-methyl-1H-[1,6]naphthyridin-2-one;

3-(2-Chloro-3,5-dimethoxyphenyl)-7-[4-(2-(diethylamino)ethoxy)phenylamino]-1-methyl-1H-[1,6]naphthyridin-2-one;

7-[4-(2-(Diethylamino)ethoxy)phenylamino]-1-methyl-3-(2-methyl-3,5-dimethoxyphenyl)-1H-[1,6]naphthyridin-2-one;

3-(2,6-Dimethyl-3,5-dimethoxyphenyl)-7-[4-(2-(diethylamino)ethoxy)phenylamino]-1-methyl-1H-[1,6]naphthyridin-2-one;

3-(2,6-Dichloro-3,5-dimethoxyphenyl)-7-[4-(2-(diethylamino)ethoxy)phenylamino]-1-ethyl-1H-[1,6]naphthyridin-2-one; and 3-(2-Chloro-3,5-dimethoxyphenyl)-7-[4-(2-(diethylamino)ethoxy)phenylamino]-1-ethyl-1H-[1,6]naphthyridin-2-one.

45. The compounds:

7-[4-(2-(Diethylamino)ethoxy)phenylamino]-1-ethyl-3-(2-methyl-3,5-dimethoxyphenyl)-1H-[1,6]naphthyridin-2-one;

7-[4-(2-(Diethylamino)ethoxy)phenylamino]-3-(2,6-dimethyl-3,5-dimethoxyphenyl)-1-ethyl-1H-[1,6]naphthyridin-2-one;

1-Methyl-7-[3-(4-methylpiperazin-1-yl)propylamino]-3-(2,3,5,6-tetramethylphenyl)-1H-[1,6]naphthyridin-2-one;

1-Ethyl-7-[3-(4-methylpiperazin-1-yl)propylamino]-3-(2,3,5,6-tetramethylphenyl)-1H-[1,6]naphthyridin-2-one;

7-(4-(Diethylamino)butylamino)-1-methyl-3-(2,3,5,6-tetramethylphenyl)-1H-[1,6]naphthyridin-2-one;

7-(4-(Diethylamino)butylamino)-1-ethyl-3-(2,3,5,6-tetramethylphenyl)-1H-[1,6]naphthyridin-2-one;

7-[4-(2-(Diethylamino)ethoxy)phenylamino]-1-ethyl-3-(2,3,5,6-tetramethylphenyl)-1H-[1,6]naphthyridin-2-one;

7-[4-(2-(Diethylamino)ethoxy)phenylamino]-1-methyl-3-(2,3,5,6-tetramethylphenyl)-1H-[1,6]naphthyridin-2-one;

1-Methyl-7-[3-(4-methylpiperazin-1-yl)propylamino]-3-phenyl-1H-[1,6]naphthyridin-2-one; and 1-Ethyl-7-[3-(4-methylpiperazin-1-yl)propylamino]-3-phenyl-1H-[1,6]naphthyridin-2-one.

46. The compounds:

7-(4-(Diethylamino)butylamino)-1-methyl-3-phenyl-1H-[1,6]naphthyridin-2-one;

7-(4-(Diethylamino)butylamino)-1-ethyl-3-phenyl-1H-[1,6]naphthyridin-2-one;

7-[4-(2-(Diethylamino)ethoxy)phenylamino]-1-ethyl-3-phenyl-1H-[1,6]naphthyridin-2-one;

7-[4-(2-(Diethylamino)ethoxy)phenylamino]-1-methyl-3-phenyl-1H-[1,6]naphthyridin-2-one;

7-[4-(2-(Diethylamino)ethoxy)phenylamino]-1-methyl-3-(thiophen-3-yl)-1H-[1,6]naphthyridin-2-one;

7-[4-(2-(Diethylamino)ethoxy)phenylamino]-1-ethyl-3-(thiophen-3-yl)-1H-[1,6]naphthyridin-2-one;

7-[4-(2-(Diethylamino)ethoxy)phenylamino]-1-methyl-3-(thiophen-2-yl)-1H-[1,6]naphthyridin-2-one; and 7-[4-(2-(Diethylamino)ethoxy)phenylamino]-1-ethyl-3-(thiophen-2-yl)-1H-[1,6]naphthyridin-2-one.

47. A compound according to claim 1 wherein — — — is absent.

48. A compound according to claim 1 wherein — — — is a bond.

49. A compound according to claim 1 wherein $R^2$ is —$CH_2CH_3$.

50. A compound according to claim 1 wherein $R^1$ is

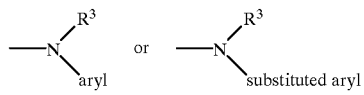

wherein aryl is phenyl and substituted aryl is substituted phenyl.

51. A compound according to claim 1 wherein $R^2$ is —$CH_3$, —$CH_2CH_3$,

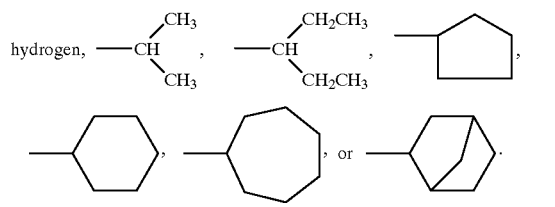

52. A compound according to claim 1 wherein $R^5$ is hydrogen

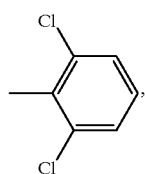

fluorine,

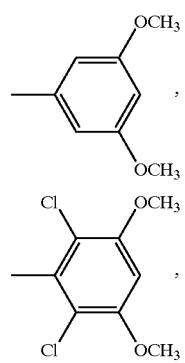

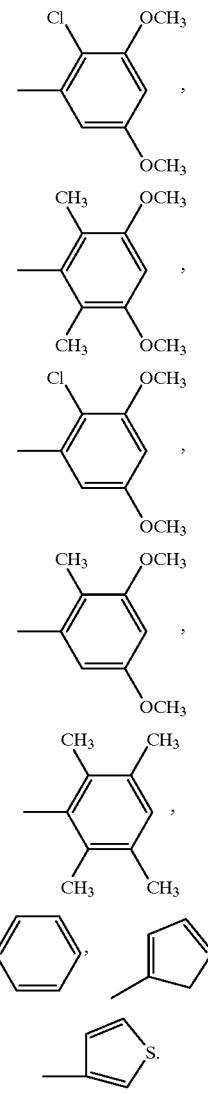

53. A compound according to claim 1 wherein $R^1$ is

—$NH_2$,

—F,

—NH-phenyl,

—NH-substituted phenyl,

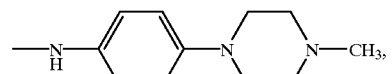

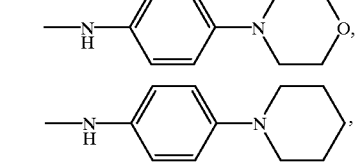

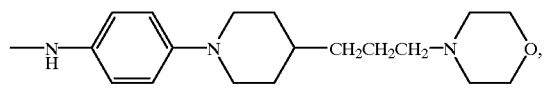

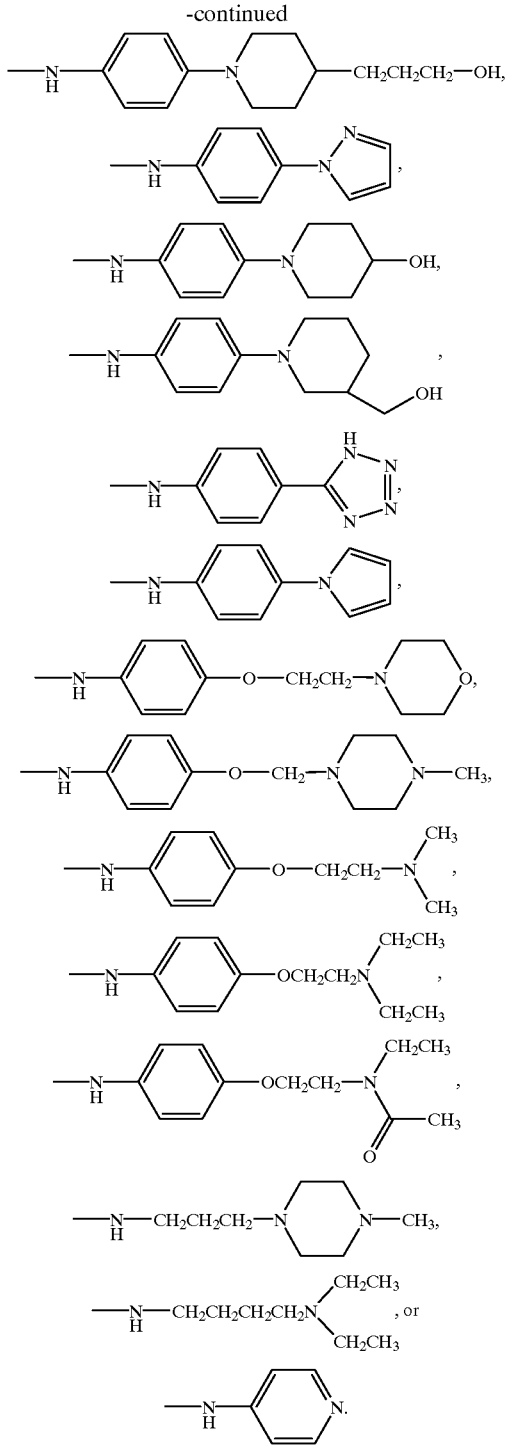
54. A compound having the Formula I
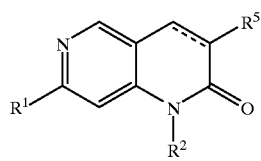
wherein
— — — is a bond or absent;
R[1] is
  —NH$_2$,
  —F,
  —NH-phenyl,
  —NH-substituted phenyl,
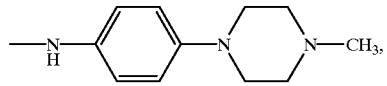
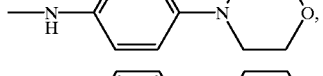
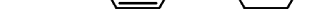
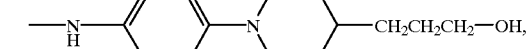
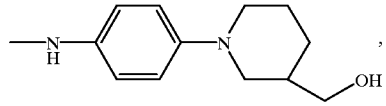
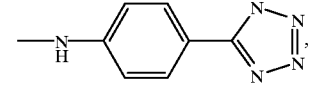
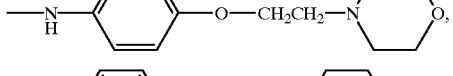
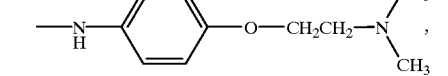
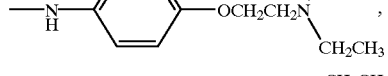
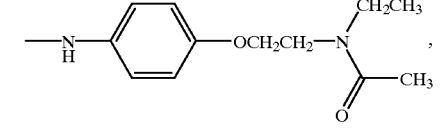

-continued

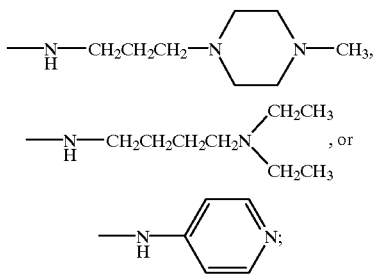

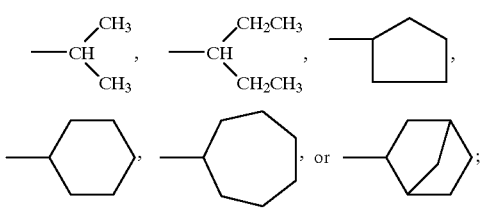

R² is
—CH₃, —CH₂CH₃, hydrogen,

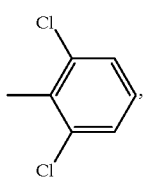

R⁵ is
hydrogen

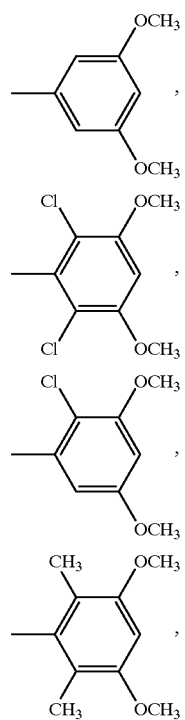

fluorine,

-continued

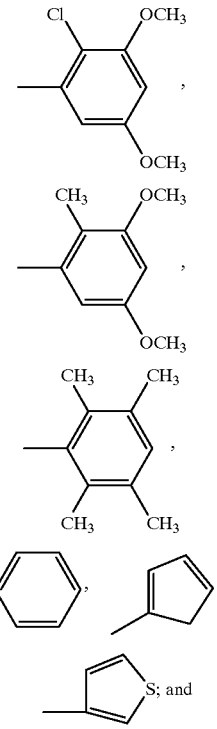

the pharmaceutically acceptable salts thereof.

55. A method of treating cancer, the method comprising administering to a patient having cancer a therapeutically effective amount of a compound of claim 1.

56. A method of treating or preventing atherosclerosis, the method comprising administering to a patient having atherosclerosis or at risk of having atherosclerosis a therapeutically effective amount of a compound of claim 1.

57. A method of treating or preventing restenosis, the method comprising administering to a patient having restenosis or at risk of having restenosis a therapeutically effective amount of a compound of claim 1.

58. A method of treating psoriasis, the method comprising administering to a patient having psoriasis a therapeutically effective amount of a compound of claim 1.

59. A method of inhibiting protein tyrosine kinases, the method comprising administering to a patient in need of protein tyrosine kinase inhibition a protein tyrosine kinase inhibiting amount of a compound of claim 1.

60. The method of claim 59 wherein the protein tyrosine kinase is c-Src.

61. The method of claim 60 wherein the protein tyrosine kinase in PDGFr.

62. The method of claim 60 wherein the protein tyrosine kinase is FGFr.

63. A method of inhibiting all cycle kinases, the method comprising administering to a patient in need of cell cycle kinase inhibition a cell cycle kinase inhibiting amount of a compound of claim 1.

64. The method of claim 63 wherein the cell cycle kinase is CDK4, CDK2, or CDK1.

65. A pharmaceutical composition that comprises a compound of claim 1.

\* \* \* \* \*